(12) United States Patent
Curran et al.

(10) Patent No.: US 12,134,648 B2
(45) Date of Patent: Nov. 5, 2024

(54) DUAL SPECIFICITY ANTIBODIES TO HUMAN PD-L1 AND PD-L2 AND METHODS OF USE THEREFOR

(71) Applicant: Board of Regents, The University of Texas System, Austin, TX (US)

(72) Inventors: Michael A. Curran, Houston, TX (US); Ashvin R. Jaiswal, Houston, TX (US); Dongxing Zha, Houston, TX (US); Carlo Toniatti, Houston, TX (US); Bianka Prinz, Lebanon, NH (US); Nadthakarn Boland, Lebanon, NH (US); Eric Krauland, Lebanon, NH (US)

(73) Assignee: Board of Regents, The University of Texas System, Austin, TX (US)

( * ) Notice: Subject to any disclaimer, the term of this patent is extended or adjusted under 35 U.S.C. 154(b) by 824 days.

(21) Appl. No.: 17/040,240

(22) PCT Filed: Mar. 14, 2019

(86) PCT No.: PCT/US2019/022295
§ 371 (c)(1),
(2) Date: Sep. 22, 2020

(87) PCT Pub. No.: WO2019/182867
PCT Pub. Date: Sep. 26, 2019

(65) Prior Publication Data
US 2021/0139591 A1 May 13, 2021

Related U.S. Application Data

(60) Provisional application No. 62/755,408, filed on Nov. 2, 2018, provisional application No. 62/647,407, filed on Mar. 23, 2018.

(51) Int. Cl.
*C07K 16/28* (2006.01)
*A61K 39/00* (2006.01)
*G01N 33/569* (2006.01)
*G01N 33/68* (2006.01)

(52) U.S. Cl.
CPC ... *C07K 16/2827* (2013.01); *G01N 33/56966* (2013.01); *G01N 33/6872* (2013.01); *A61K 2039/505* (2013.01); *C07K 2317/24* (2013.01); *C07K 2317/31* (2013.01); *C07K 2317/565* (2013.01)

(58) Field of Classification Search
CPC ............ C07K 16/2827; C07K 2317/24; C07K 2317/31; C07K 2317/565; G01N 33/56966; G01N 33/6872; A61K 2039/505
See application file for complete search history.

(56) References Cited

U.S. PATENT DOCUMENTS

| 5,595,756 A * | 1/1997 | Bally ............... A61K 9/1272 264/4.1 |
| 9,567,399 B1 | 2/2017 | Campbell et al. |
| 10,101,333 B2 * | 10/2018 | Smider ............... A61P 31/12 |
| 2003/0194704 A1 | 10/2003 | Penn et al. |
| 2004/0131613 A1 | 7/2004 | Watkins et al. |
| 2005/0059113 A1 | 3/2005 | Bedian et al. |
| 2008/0213251 A1 | 9/2008 | Sexton et al. |
| 2008/0262203 A1 | 10/2008 | Clegg et al. |
| 2011/0110956 A1 | 5/2011 | Rothe et al. |
| 2013/0156781 A1 | 6/2013 | Dmitrov et al. |
| 2015/0329642 A1 | 11/2015 | Neijssen et al. |
| 2016/0311903 A1 | 10/2016 | West et al. |
| 2017/0007693 A1 | 1/2017 | Weiner et al. |
| 2017/0088620 A1 | 3/2017 | Nioi et al. |
| 2017/0137522 A1 | 5/2017 | Queva et al. |
| 2017/0158767 A1 | 6/2017 | Korman et al. |
| 2017/0306028 A1 | 10/2017 | Knopf et al. |
| 2017/0355757 A1 | 12/2017 | Hu et al. |
| 2021/0198360 A1 | 7/2021 | Curran et al. |
| 2021/0214445 A1 | 7/2021 | Curran et al. |

FOREIGN PATENT DOCUMENTS

| WO | WO 2005-023177 A2 | 3/2005 |
| WO | WO 2007-030642 A2 | 3/2007 |
| WO | WO 2007-097923 A2 | 8/2007 |
| WO | WO 2011-066342 A2 | 6/2011 |
| WO | WO 2011-066389 A1 | 6/2011 |
| WO | WO 2013-079174 A1 | 6/2013 |
| WO | WO 2014-022758 A1 | 2/2014 |
| WO | WO 2016-081639 A1 | 5/2016 |
| WO | WO 2016-111645 A1 | 7/2016 |
| WO | WO 2016-144728 A2 | 9/2016 |
| WO | WO 2016-160792 A1 | 10/2016 |
| WO | WO 2017-053250 A1 | 3/2017 |
| WO | WO 2017-070170 A1 | 4/2017 |

(Continued)

OTHER PUBLICATIONS

Heppner et al., 1983, Cancer Metastasis Reviews 2: 5-23 (Year: 1983).*
Lazar et al., Mol. Cell. Biol., 8:1247-1252, 1988 (Year: 1988).*
Bowie et al., Science, 1990, 247:1306-1310 (Year: 1990).*
Burgess et al., J. Cell Biol. 111: 2129-2138, 1990 (Year: 1990).*
Jain, Jul. 1994, Scientific American, pp. 58-65 (Year: 1994).*
MacCallum et al., 1996, J. Mol. Biol. 262: 732-745 (Year: 1996).*
Gura, 1997, Science 278(5340): 1041-1042 (Year: 1997).*
Greenspan et al., 1999, Nature Biotechnology, 17:936-937 (Year: 1999).*
Bork. Genome Research, 2000, 10:398-400 (Year: 2000).*
Auerbach et al., 2000, Cancer and Metastasis Reviews 19:167-172 (Year: 2000).*

(Continued)

*Primary Examiner* — Vanessa L. Ford
*Assistant Examiner* — Danaya L Middleton
(74) *Attorney, Agent, or Firm* — Parker Highlander PLLC

(57) ABSTRACT

The present disclosure is directed to bispecific antibodies which bind to both PD-L1 and PD-L2, and methods of using such antibodies to treat cancers, such as those that express or overexpress PD-L1, PD-L2, or both.

16 Claims, 24 Drawing Sheets

Figure 1B:
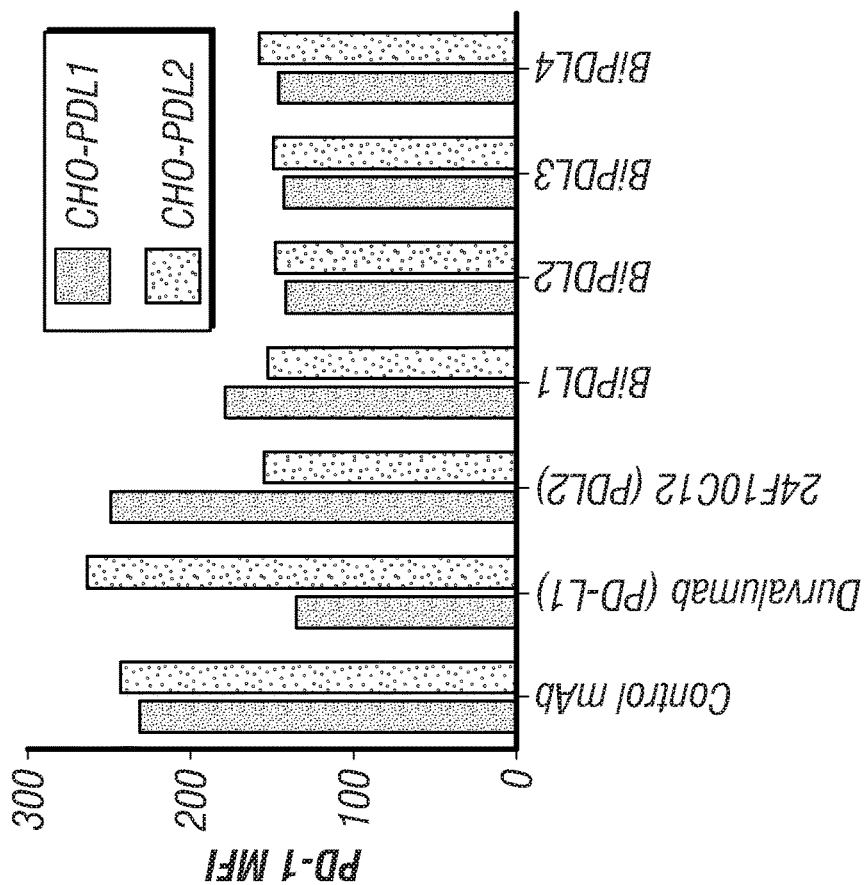

Specification includes a Sequence Listing.

(56) References Cited

FOREIGN PATENT DOCUMENTS

| WO | WO 2017-106453 A1 | 6/2017 |
|---|---|---|
| WO | WO 2017-118321 A1 | 7/2017 |
| WO | WO 2017-156479 A1 | 9/2017 |
| WO | WO 2017-172517 A1 | 10/2017 |
| WO | WO 2017-200796 A1 | 11/2017 |
| WO | WO 2019-182867 A1 | 9/2019 |
| WO | WO 2019-182888 A1 | 9/2019 |

OTHER PUBLICATIONS

Sporn et al., Carcinogenesis, vol. 21 (2000), 525-530 (Year: 2000).*
Vajdos et al., 2002, J. Mol. Biol. 320: 415-428 (Year: 2002).*
Paul, Fundamental Immunology, 2003, 5th Edition, Raven Press, New York, Chapter 3, pp. 109-147 (Year: 2003).*
Casset et al., 2003, Biochemical and Biophysical Research Communications 307:198-205 (Year: 2003).*
Hait, 2010, Nature Reviews|Drug Discovery 9: 253-254 (Year: 2010).*
Sela-Culang et al., 2013, Frontiers in Immunology 4(302): 1-13 (Year: 2013).*
Gravanis et al., 2014, Chin Clin Oncol 3(2):22, pp. 1-5 (Year: 2014).*
Beans, 2018, PNAS 115(5): 12539-12543 (Year: 2018).*
Office Action issued in Singapore Application No. 11202009258R, dated Jun. 29, 2022.
Office Action issued in Japanese Application No. 2020-550644, dated Jan. 30, 2023, and English translation thereof.
Almagro et al., "Humanization of antibodies," *Frontiers in Bioscience*, 13:1619-1633, 2008.
Boussiotis, "Molecular and Biochemical Aspects of the PD-1 Checkpoint Pathway," *N Engl J Med*, 375(18):1767-1778, 2016.
Boyerinas et al., "Antibody-Dependent Cellular Cytotoxicity Activity of a Novel Anti-PD-L1 Antibody Avelumab (MSB0010718C) on Human Tumor Cells," *Cancer Immunol. Res.*, 3(10):1148-1157, 2015.
Brahmer et al., "Phase I Study of Single-Agent Anti-Programmed Death-1 (MDX-1106) in Refractory Solid Tumors: Safety, Clinical Activity, Pharmacodynamics, and Immunologic Correlates," *J. Clin. Oncolo.*, 28:3167-3175, 2010.
Brahmer et al., "Safety and Activity of Anti-PD-L1 Antibody in Patients with Advanced Cancer," *N. Eng. J. Med*, 366:2455-2465, 2012.
Brown et al., "Blockade of programmed dealth-1 ligands on dendritic cells enhances T cell activation and cytokine production," *The Journal of Immunology*, 170(3):1257-1266, 2003.
Cheng et al., "Structure and interactions of the human programmed cell death 1 receptor," *J. Biol. Chem.*, 288(17):11771-11785, 2013.
Extended European Search Report issued in European Application No. 18866472.6, mailed Oct. 28, 2021.
Extended European Search Report issued in European Application No. 19771524.6, mailed Nov. 10, 2021.
Extended European Search Report issued in European Application No. 19771183.1, mailed Nov. 25, 2021.
Extended European Search Report issued in European Application No. 19772548.4, mailed Nov. 22, 2021.
Latchman et al., "PD-L2 is a second ligand for PD-1 and inhibits T cell activation," *Nat. Immunol.*, 2(3):261-268, 2001.
Lee et al., "Magneto-nanosensor platform for probing low-affinity protein-protein interactions and identification of a low-affinity PD-L1/PD-L2 interaction," *Nat. Commun.*, 7: 12220, 2016.
Office Action issued in U.S. Appl. No. 16/754,852, mailed Jan. 11, 2022.
PCT International Search Report and Written Opinion issued in International Application No. PCT/US2018/055261, mailed Jan. 29, 2019.
PCT International Search Report and Written Opinion issued in International Application No. PCT/US2019/022444, mailed Aug. 9, 2019.
PCT International Search Report and Written Opinion issued in International Application No. PCT/US2019/022295, mailed Jul. 29, 2019.
PCT International Search Report and Written Opinion issued in International Application No. PCT/US2019/022491, mailed Jul. 17, 2019.
Radhakrishnan et al., "Blockade of allergic airway inflammation following systemic treatment with a B7-dendritic cell (PD-L2) cross-linking human antibody," *The Journal of Immunology*, 173(2):1360-1365, 2004.
Radhakrishnan et al., "Naturally occurring human IgM antibody that binds B7-DC and potentiates T cell stimulation by dendritic cells," *The Journal of Immunology*, 170(4):1830-1838, 2003.
Sun et al., "Regulation and fuction of the PD-L1 checkpoint," *Immunity*, 48(3):434-452, 2018.
Yearley et al., "PD-L2 expression in human tumors: relevance to Anti-PD-1 therapy in cancer," *Clinical Cancer Research*, 23(12):3158-3167, 2017.
Couillault, C. et al., "Dual-specific antibodies blocking both PD-L1 and PD-L2 engagement of PD-1 restore anti-tumor immunity," *J Immunother Cancer*, 9.2 (2021): abstract.

* cited by examiner

| | BiPDL3-1$_1$ | BiPDL3-1$_3$ | BiPDL4-1$_1$ | BiPDL4-1$_2$ | BiPDL4-2$_2$ | BiPDL4-1$_3$ |
|---|---|---|---|---|---|---|
| Ec50 (nM, 10^9) | P.F. | 0.08 | 0.038 | 0.014 | 0.43 | 0.014 |
| % Killing | 20% | 33% | 36% | 35% | 40% | 40% |

Figure 6:
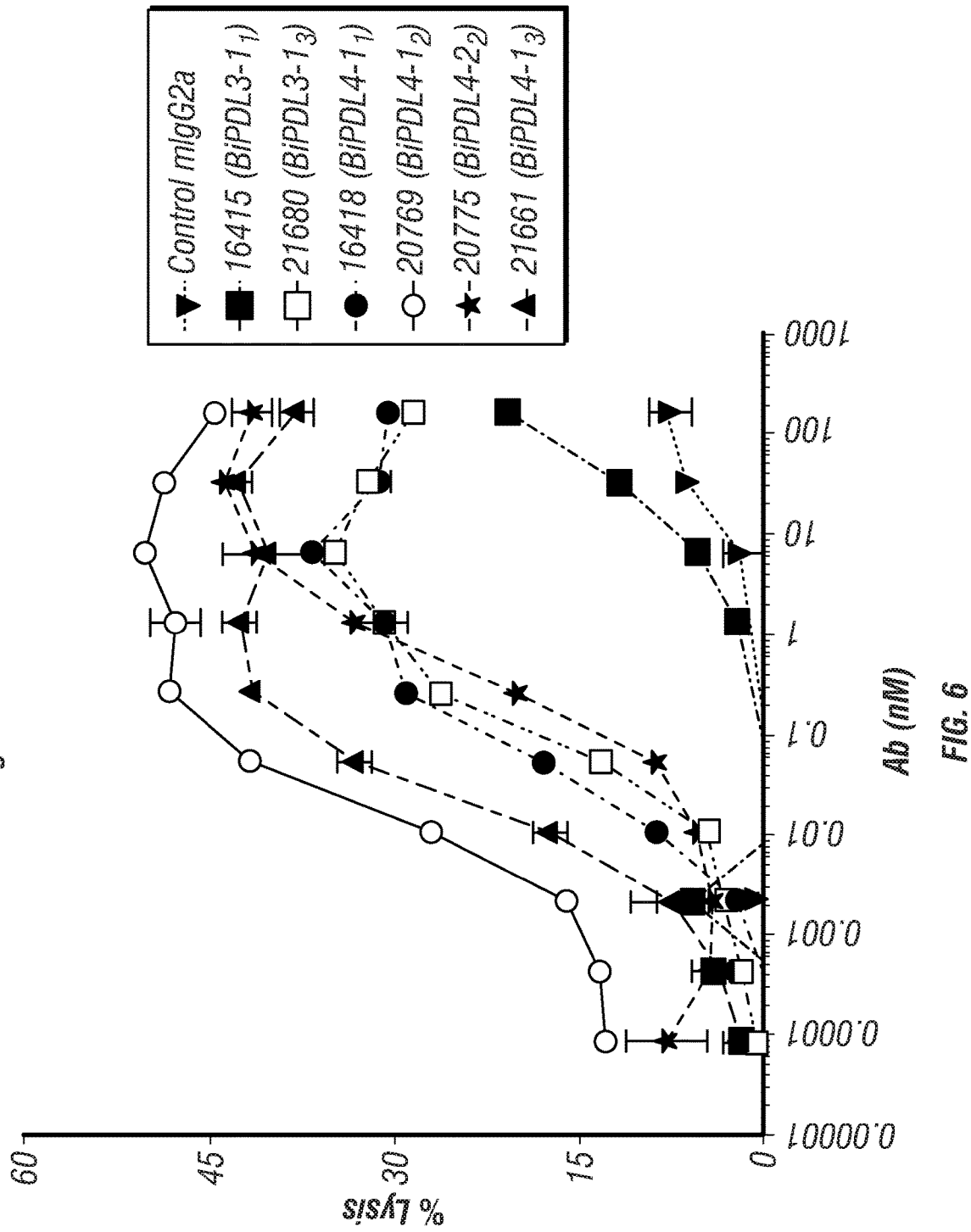

FIG. 6
(Cont'd)

SEQUENCE LISTING

<160> NUMBER OF SEQ ID NOS: 101

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 273
<212> TYPE: PRT
<213> ORGANISM: Homo sapiens

<400> SEQUENCE: 2

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile

```
            20                  25                  30
Glu His Gly Ser Asn Val Thr Leu Glu Cys Asn Phe Asp Thr Gly Ser
                35                  40                  45

His Val Asn Leu Gly Ala Ile Thr Ala Ser Leu Gln Lys Val Glu Asn
 50                  55                  60

Asp Thr Ser Pro His Arg Glu Arg Ala Thr Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
                115                 120                 125

His Ile Leu Lys Val Pro Glu Thr Asp Glu Val Glu Leu Thr Cys Gln
                130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
                180                 185                 190

Val Phe Trp Asn Thr His Val Arg Glu Leu Thr Leu Ala Ser Ile Asp
                195                 200                 205

Leu Gln Ser Gln Met Glu Pro Arg Thr His Pro Thr Trp Leu Leu His
                210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
                260                 265                 270

Ile

<210> SEQ ID NO 3
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 3
caggtgcagc tggtggagtc tgggggaggc gtggtccagc ctggaggtc cctgagactc      60 tcctgtgcag cgtctggatt caccttcgat gagtatggca tgcactgggt ccgccaggct     120
ccaggcaagg gctggagtg gtggcagtt atagggtatg atggactgaa taaatactat      180
gcagactccg tgaagggccg attcaccatc tccagagaca attccaagaa cacgctgtat    240
ctgcaaatga acagcctgag agccgaggac acggcggtgt actactgcgc cagagctgga    300
atagaataca gctacgccta tactgattac tggggacagg gtacattggt caccgtctcc    360
tca                                                                  363

<210> SEQ ID NO 4
<211> LENGTH: 327
<212> TYPE: DNA
<213> ORGANISM: Artificial sequence
<220> FEATURE:
```

<223> OTHER INFORMATION: Synthetic oligonucleotide

<400> SEQUENCE: 4

```
gaaattgtgt tgacgcagtc tccaggcacc ctgtctttgt ctccagggga aagagccacc      60
ctctcctgca gggccagtca gttcgtttac agcagcgact tagcctggta ccagcagaaa     120
cctggccagg ctcccaggct cctcatctat ggtgcatcca ccaggaaaac tggcatccca     180
gacaggttca gtggcagtgg gtctgggaca gacttcactc tcaccatcag cagactggag     240
cctgaagatt ttgcagtgta ttactgtctg cagttcggat ggtggcctcc taggactttc     300
ggcggaggga ccaaggtgga gatcaaa                                          327
```

<210> SEQ ID NO 5
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 5

```
caggtgcagc tggtggagtc tgggggaggc gtggtccagc ctgggaggtc cctgagactc      60
tcctgtgcag cgtctggatt caccttcgat gagtatggca tgcactgggt ccgccaggct     120
ccagcaaggg gctggagtg gtggcagtt atagggtatg atggactgaa taaatactat       180
gcagactccg tgaagggccg attcaccatc tccagagaca attccaagaa cacgctgtat     240
ctgcaaatga acagcctgag agccgaggac acggcggtgt actactgcgc cagagctgga     300
atagaataca gctacgccta tactgattac tggggacagg gtacattggt caccgtctcc     360
tca                                                                    363
```

<210> SEQ ID NO 6
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 6

```
gaaattgtgt tgacgcagtc tccaggcacc ctgtctttgt ctccagggga aagagccacc      60
ctctcctgca gggccagtaa cagtgttgtc agcagctact agcctggta ccagcagaaa      120
cctggccagg ctcccaggct cctcatctat ggtgcagcca gagggccaa cggcatccca     180
gacaggttca gtggcagtgg gtctgggaca gacttcactc tcaccatcag cagactggag     240
cctgaagatt ttgcagtgta ttactgtgtt cagttcggat ggtggcctcc taggactttc     300
ggcggaggga ccaaggtgga gatcaaa                                          327
```

<210> SEQ ID NO 7
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagc tggtggagtc tgggggaggc gtgatccagc ctgggaggtc cctgagactc      60
tcctgtgcag cgtctggatt caccttcagt gcgtatctta tgcactgggt ccgccaggct     120
ccaggcaagg gctggagtg gtggcagct ataggttatg atggaatgaa taaatactat       180
gcagactccg tgaagggccg attcaccatc tccagagaca attccaagaa cacgctgtat     240
```
ctgcaaatga acagcctgag agccgaggac acggcggtgt actactgcgc cagagctgga   300
atagaataca gctacgccta tactgattac tggggacagg gtacattggt caccgtctcc   360
tca                                                                 363

```
<210> SEQ ID NO 8
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 8
```
gaaattgtgt tgacgcagtc tccaggcacc ctgtctttgt ctccagggga aagagccacc    60
ctctcctgca gggccagtca gttcgtttac agcagcgact tagcctggta ccagcagaaa   120
cctggccagg ctcccaggct cctcatctat ggtgcatccg ccaggccgc cggcatccca    180 gacaggttca gtggcagtgg gtctgggaca gacttcactc tcaccatcag cagactggag   240
cctgaagatt ttgcagtgta ttactgtatg cagttcggat ggtggcctcc taggactttc   300
ggcggaggga ccaaggttga gatcaaa                                       327

```
<210> SEQ ID NO 9
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 9
```
caggtgcagc tggtggagtc tgggggaggc gtgatccagc ctgggaggtc cctgagactc    60
tcctgtgcag cgtctggatt caccttcagt gcgtatctta tgcactgggt ccgccaggct   120
ccaggcaagg ggctggagtg ggtggcagct ataggttatg atggaatgaa taaatactat   180
gcagactccg tgaagggccg attcaccatc tccagagaca attccaagaa cacgctgtat   240
ctgcaaatga acagcctgag agccgaggac acggcggtgt actactgcgc cagagctgga   300
atagaataca gctacgccta tactgattac tggggacagg gtacattggt caccgtctcc   360
tca                                                                 363

```
<210> SEQ ID NO 10
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 10
```
gaaattgtgt tgacgcagtc tccaggcacc ctgtctttgt ctccagggga aagagccacc    60
ctctcctgca gggccagtca cagtgttgtc agcagctact agcctggta ccagcagaaa    120 cctggccagg ctcccaggct cctcatctat ggtgcatcca gcaggaaga cggcatccca    180 gacaggttca gtggcagtgg gtctgggaca gacttcactc tcaccatcag cagactggag   240
cctgaagatt ttgcagtgta ttactgtgtg cagttcggat ggtggcctcc taggactttc   300
ggcggaggga ccaaggtgga gatcaaa                                       327

```
<210> SEQ ID NO 11
<211> LENGTH: 360
<212> TYPE: DNA
```

<213> ORGANISM: Artificial sequence
<220> FEATURE:
<223> OTHER INFORMATION: Synthetic oligonucleotide

<400> SEQUENCE: 11

```
caagtacaat tacaacagtg gggagctggt ttattaaagc cttcagaaac tttaagtttg     60
acctgtgctg tttacggtgg atcattatct ggttatcctt ggtcttggat tcgtcaacca    120
ccaggcaaag gattggagtg gatcggtgag acagacgtgt caggctggac tgactacaat    180
ccaagtttaa aatccagggt tactatctcc gtagacacgt ccaagaacca gttctccctg    240
aagctgagtt ctgtgaccgc cgcagacacg gcggtgtact actgcgccag agacggcaga    300
aggatgggta cccttcatt cgacatatgg ggccaggtca atggtcac cgtctcctca       360
```

<210> SEQ ID NO 12
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 12

```
gacatccagt tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatcaagtt tgcaaagtgg ggtcccatca    180
aggttcagcg gcagtggatc tgggacagat ttcactctca ccatcagcag cctgcagcct    240
gaagattttg caacttatta ctgtcagcag tacgtctact cccctcctac ttttggcgga    300
gggaccaagg ttgagatcaa a                                              321
```

<210> SEQ ID NO 13
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 13

```
caggtgcagc tggtgcagtc tggggctgag gtgaagaagc ctgggtcctc ggtgaaggtc     60
tcctgcaagg cttctggagg cacctttcagc agctggttga tcagctgggt gcgacaggcc   120
cctggacaag gcttgagtg gatgggaggg atcatcccta tcctgggtac agcacggtac     180
gcacagaagt tccagggcag agtcacgatt accgcggacg aatccacgag cacagcctac    240
atggagctga gcagcctgag atctgaggac acggcggtgt actactgcgc cagagtgtac    300
agagctgctt cttggtttga tccctgggga caggtacat tggtcaccgt ctcctca        357
```

<210> SEQ ID NO 14
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 14

```
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg gaagtggatc tgggacagat tttacttca ccatcagcag cctgcagcct     240
```

```
gaagatattg caacatatta ctgtcagcag cccttccacc tcatcacttt tggcggaggg    300
accaaggttg agatcaaa                                                  318
```

<210> SEQ ID NO 15
<211> LENGTH: 121
<212> TYPE: PRT
<213> ORGANISM: Artificial sequence
<220> FEATURE:
<223> OTHER INFORMATION: Synthetic amino acid

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ala Val Ile Gly Tyr Asp Gly Leu Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Ile Glu Tyr Ser Tyr Ala Tyr Thr Asp Tyr Trp Gly
            100                 105                 110

Gln Gly Thr Leu Val Thr Val Ser Ser
        115                 120

<210> SEQ ID NO 16
<211> LENGTH: 109
<212> TYPE: PRT
<213> ORGANISM: Artificial sequence
<220> FEATURE:
<223> OTHER INFORMATION: Synthetic amino acid

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Phe Val Tyr Ser Ser
            20                  25                  30

Asp Leu Ala Trp Tyr Gln Gln Lys Pro Gly Gln Ala Pro Arg Leu Leu
        35                  40                  45

Ile Tyr Gly Ala Ser Thr Arg Lys Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Leu Gln Phe Gly Trp Trp Pro
                85                  90                  95

Pro Arg Thr Phe Gly Gly Gly Thr Lys Val Glu Ile Lys
            100                 105

<210> SEQ ID NO 17
<211> LENGTH: 121
<212> TYPE: PRT
<213> ORGANISM: Artificial sequence
<220> FEATURE:
<223> OTHER INFORMATION: Synthetic amino acid

<400> SEQUENCE: 17

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ala Val Ile Gly Tyr Asp Gly Leu Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Ile Glu Tyr Ser Tyr Ala Tyr Thr Asp Tyr Trp Gly
            100                 105                 110

Gln Gly Thr Leu Val Thr Val Ser Ser
        115                 120
```

<210> SEQ ID NO 18
<211> LENGTH: 109
<212> TYPE: PRT
<213> ORGANISM: Artificial sequence
<220> FEATURE:
<223> OTHER INFORMATION: Synthetic amino acid

<400> SEQUENCE: 18

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Asn Ser Val Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ala Ser Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Val Gln Phe Gly Trp Trp Pro
                85                  90                  95

Pro Arg Thr Phe Gly Gly Gly Thr Lys Val Glu Ile Lys
            100                 105
```

<210> SEQ ID NO 19
<211> LENGTH: 121
<212> TYPE: PRT
<213> ORGANISM: Artificial sequence
<220> FEATURE:
<223> OTHER INFORMATION: Synthetic amino acid

<400> SEQUENCE: 19

```
Gln Val Gln Leu Val Glu Ser Gly Gly Val Ile Gln Pro Gly Arg
1               5                   10                  15

Ser Leu Arg Leu Ser Cys Ala Ala Ser Gly Phe Thr Phe Ser Ala Tyr
            20                  25                  30

Leu Met His Trp Val Arg Gln Ala Pro Gly Lys Gly Leu Glu Trp Val
        35                  40                  45

Ala Ala Ile Gly Tyr Asp Gly Met Asn Lys Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Ala Gly Ile Glu Tyr Ser Tyr Ala Tyr Thr Asp Tyr Trp Gly
                100                 105                 110

Gln Gly Thr Leu Val Thr Val Ser Ser
            115                 120

<210> SEQ ID NO 20
<211> LENGTH: 109
<212> TYPE: PRT
<213> ORGANISM: Artificial sequence
<220> FEATURE:
<223> OTHER INFORMATION: Synthetic amino acid

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Phe Val Tyr Ser Ser
                20                  25                  30

Asp Leu Ala Trp Tyr Gln Gln Lys Pro Gly Gln Ala Pro Arg Leu Leu
            35                  40                  45

Ile Tyr Gly Ala Ser Ala Arg Ala Ala Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Met Gln Phe Gly Trp Trp Pro
                85                  90                  95

Pro Arg Thr Phe Gly Gly Gly Thr Lys Val Glu Ile Lys
                100                 105

<210> SEQ ID NO 21
<211> LENGTH: 121
<212> TYPE: PRT
<213> ORGANISM: Artificial sequence
<220> FEATURE:
<223> OTHER INFORMATION: Synthetic amino acid

<400> SEQUENCE: 21

Gln Val Gln Leu Val Glu Ser Gly Gly Val Ile Gln Pro Gly Arg
1               5                   10                  15

Ser Leu Arg Leu Ser Cys Ala Ala Ser Gly Phe Thr Phe Ser Ala Tyr
                20                  25                  30

Leu Met His Trp Val Arg Gln Ala Pro Gly Lys Gly Leu Glu Trp Val
            35                  40                  45

Ala Ala Ile Gly Tyr Asp Gly Met Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Ile Glu Tyr Ser Tyr Ala Tyr Thr Asp Tyr Trp Gly
                100                 105                 110

Gln Gly Thr Leu Val Thr Val Ser Ser
            115                 120

<210> SEQ ID NO 22
<211> LENGTH: 109
```

```
<212> TYPE: PRT
<213> ORGANISM: Artificial sequence
<220> FEATURE:
<223> OTHER INFORMATION: Synthetic amino acid

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser His Ser Val Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Glu Asp Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Val Gln Phe Gly Trp Trp Pro
                85                  90                  95

Pro Arg Thr Phe Gly Gly Gly Thr Lys Val Glu Ile Lys
            100                 105

<210> SEQ ID NO 23
<211> LENGTH: 120
<212> TYPE: PRT
<213> ORGANISM: Artificial sequence
<220> FEATURE:
<223> OTHER INFORMATION: Synthetic amino acid

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Pro Trp Ser Trp Ile Arg Gln Pro Pro Gly Lys Gly Leu Glu Trp Ile
        35                  40                  45

Gly Glu Thr Asp Val Ser Gly Trp Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Arg Arg Met Gly Thr Pro Ser Phe Asp Ile Trp Gly Gln
            100                 105                 110

Gly Thr Met Val Thr Val Ser Ser
        115                 120

<210> SEQ ID NO 24
<211> LENGTH: 107
<212> TYPE: PRT
<213> ORGANISM: Artificial sequence
<220> FEATURE:
<223> OTHER INFORMATION: Synthetic amino acid

<400> SEQUENCE: 24

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
```

```
                35                  40                  45
Tyr Ala Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Val Tyr Phe Pro Pro
                 85                  90                  95
Thr Phe Gly Gly Gly Thr Lys Val Glu Ile Lys
            100                 105

<210> SEQ ID NO 25
<211> LENGTH: 119
<212> TYPE: PRT
<213> ORGANISM: Artificial sequence
<220> FEATURE:
<223> OTHER INFORMATION: Synthetic amino acid

<400> SEQUENCE: 25

Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Ser Trp
             20                  25                  30
Leu Ile Ser Trp Val Arg Gln Ala Pro Gly Gln Gly Leu Glu Trp Met
         35                  40                  45
Gly Gly Ile Ile Pro Ile Leu Gly Thr Ala Arg Tyr Ala Gln Lys Phe
     50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Val Tyr Arg Ala Ala Ser Trp Phe Asp Pro Trp Gly Gln Gly
            100                 105                 110
Thr Leu Val Thr Val Ser Ser
        115

<210> SEQ ID NO 26
<211> LENGTH: 106
<212> TYPE: PRT
<213> ORGANISM: Artificial sequence
<220> FEATURE:
<223> OTHER INFORMATION: Synthetic amino acid

<400> SEQUENCE: 26

Asp Ile Gln Met Thr Gln Ser Pro Ser Ser Leu Ser Ala Ser Val Gly
 1               5                  10                  15
Asp Arg Val Thr Ile Thr Cys Gln Ala Ser Gln Asp Ile Ser Asn Tyr
             20                  25                  30
Leu Asn Trp Tyr Gln Gln Lys Pro Gly Lys Ala Pro Lys Leu Leu Ile
         35                  40                  45
Tyr Asp Ala Ser Asn Leu Glu Thr Gly Val Pro Ser Arg Phe Ser Gly
     50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Gln Gln Pro Phe His Leu Ile Thr
                 85                  90                  95
Phe Gly Gly Gly Thr Lys Val Glu Ile Lys
            100                 105
```

<210> SEQ ID NO 27
<211> LENGTH: 9
<212> TYPE: PRT
<213> ORGANISM: Artificial sequence
<220> FEATURE:
<223> OTHER INFORMATION: Synthetic amino acid

<400> SEQUENCE: 27

Phe Thr Phe Asp Glu Tyr Gly Met His
1               5

<210> SEQ ID NO 28
<211> LENGTH: 17
<212> TYPE: PRT
<213> ORGANISM: Artificial sequence
<220> FEATURE:
<223> OTHER INFORMATION: Synthetic amino acid

<400> SEQUENCE: 28

Val Ile Gly Tyr Asp Gly Leu Asn Lys Tyr Tyr Ala Asp Ser Val Lys
1               5                   10                  15

Gly

<210> SEQ ID NO 29
<211> LENGTH: 14
<212> TYPE: PRT
<213> ORGANISM: Artificial sequence
<220> FEATURE:
<223> OTHER INFORMATION: Synthetic amino acid

<400> SEQUENCE: 29

Ala Arg Ala Gly Ile Glu Tyr Ser Tyr Ala Tyr Thr Asp Tyr
1               5                   10

<210> SEQ ID NO 30
<211> LENGTH: 9
<212> TYPE: PRT
<213> ORGANISM: Artificial sequence
<220> FEATURE:
<223> OTHER INFORMATION: Synthetic amino acid

<400> SEQUENCE: 30

Phe Thr Phe Asp Glu Tyr Gly Met His
1               5

<210> SEQ ID NO 31
<211> LENGTH: 17
<212> TYPE: PRT
<213> ORGANISM: Artificial sequence
<220> FEATURE:
<223> OTHER INFORMATION: Synthetic amino acid

<400> SEQUENCE: 31

Val Ile Gly Tyr Asp Gly Leu Asn Lys Tyr Tyr Ala Asp Ser Val Lys
1               5                   10                  15

Gly

<210> SEQ ID NO 32
<211> LENGTH: 14
<212> TYPE: PRT
<213> ORGANISM: Artificial sequence
<220> FEATURE:
<223> OTHER INFORMATION: Synthetic amino acid

<400> SEQUENCE: 32

```
Ala Arg Ala Gly Ile Glu Tyr Ser Tyr Ala Tyr Thr Asp Tyr
1               5                   10
```

<210> SEQ ID NO 33
<211> LENGTH: 9
<212> TYPE: PRT
<213> ORGANISM: Artificial sequence
<220> FEATURE:
<223> OTHER INFORMATION: Synthetic amino acid

<400> SEQUENCE: 33

```
Phe Thr Phe Ser Ala Tyr Leu Met His
1               5
```

<210> SEQ ID NO 34
<211> LENGTH: 17
<212> TYPE: PRT
<213> ORGANISM: Artificial sequence
<220> FEATURE:
<223> OTHER INFORMATION: Synthetic amino acid

<400> SEQUENCE: 34

```
Ala Ile Gly Tyr Asp Gly Met Asn Lys Tyr Tyr Ala Asp Ser Val Lys
1               5                   10                  15

Gly
```

<210> SEQ ID NO 35
<211> LENGTH: 14
<212> TYPE: PRT
<213> ORGANISM: Artificial sequence
<220> FEATURE:
<223> OTHER INFORMATION: Synthetic amino acid

<400> SEQUENCE: 35

```
Ala Arg Ala Gly Ile Glu Tyr Ser Tyr Ala Tyr Thr Asp Tyr
1               5                   10
```

<210> SEQ ID NO 36
<211> LENGTH: 9
<212> TYPE: PRT
<213> ORGANISM: Artificial sequence
<220> FEATURE:
<223> OTHER INFORMATION: Synthetic amino acid

<400> SEQUENCE: 36

```
Phe Thr Phe Ser Ala Tyr Leu Met His
1               5
```

<210> SEQ ID NO 37
<211> LENGTH: 17
<212> TYPE: PRT
<213> ORGANISM: Artificial sequence
<220> FEATURE:
<223> OTHER INFORMATION: Synthetic amino acid

<400> SEQUENCE: 37

```
Ala Ile Gly Tyr Asp Gly Met Asn Lys Tyr Tyr Ala Asp Ser Val Lys
1               5                   10                  15

Gly
```

<210> SEQ ID NO 38
<211> LENGTH: 14
<212> TYPE: PRT
<213> ORGANISM: Artificial sequence
<220> FEATURE:
<223> OTHER INFORMATION: Synthetic amino acid

```
<400> SEQUENCE: 38

Ala Arg Ala Gly Ile Glu Tyr Ser Tyr Ala Tyr Thr Asp Tyr
1               5                   10

<210> SEQ ID NO 39
<211> LENGTH: 9
<212> TYPE: PRT
<213> ORGANISM: Artificial sequence
<220> FEATURE:
<223> OTHER INFORMATION: Synthetic amino acid

<400> SEQUENCE: 39

Gly Ser Leu Ser Gly Tyr Pro Trp Ser
1               5

<210> SEQ ID NO 40
<211> LENGTH: 16
<212> TYPE: PRT
<213> ORGANISM: Artificial sequence
<220> FEATURE:
<223> OTHER INFORMATION: Synthetic amino acid

<400> SEQUENCE: 40

Glu Thr Asp Val Ser Gly Trp Thr Asp Tyr Asn Pro Ser Leu Lys Ser
1               5                   10                  15

<210> SEQ ID NO 41
<211> LENGTH: 14
<212> TYPE: PRT
<213> ORGANISM: Artificial sequence
<220> FEATURE:
<223> OTHER INFORMATION: Synthetic amino acid

<400> SEQUENCE: 41

Ala Arg Asp Gly Arg Arg Met Gly Thr Pro Ser Phe Asp Ile
1               5                   10

<210> SEQ ID NO 42
<211> LENGTH: 9
<212> TYPE: PRT
<213> ORGANISM: Artificial sequence
<220> FEATURE:
<223> OTHER INFORMATION: Synthetic amino acid

<400> SEQUENCE: 42

Gly Thr Phe Ser Ser Trp Leu Ile Ser
1               5

<210> SEQ ID NO 43
<211> LENGTH: 17
<212> TYPE: PRT
<213> ORGANISM: Artificial sequence
<220> FEATURE:
<223> OTHER INFORMATION: Synthetic amino acid

<400> SEQUENCE: 43

Gly Ile Ile Pro Ile Leu Gly Thr Ala Arg Tyr Ala Gln Lys Phe Gln
1               5                   10                  15

Gly

<210> SEQ ID NO 44
<211> LENGTH: 12
<212> TYPE: PRT
<213> ORGANISM: Artificial sequence
<220> FEATURE:
```

```
<223> OTHER INFORMATION: Synthetic amino acid

<400> SEQUENCE: 44

Ala Arg Val Tyr Arg Ala Ala Ser Trp Phe Asp Pro
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthetic amino acid

<400> SEQUENCE: 45

Arg Ala Ser Gln Phe Val Tyr Ser Ser Asp Leu Ala
1               5                   10

<210> SEQ ID NO 46
<211> LENGTH: 7
<212> TYPE: PRT
<213> ORGANISM: Artificial sequence
<220> FEATURE:
<223> OTHER INFORMATION: Synthetic amino acid

<400> SEQUENCE: 46

Gly Ala Ser Thr Arg Lys Thr
1               5

<210> SEQ ID NO 47
<211> LENGTH: 10
<212> TYPE: PRT
<213> ORGANISM: Artificial sequence
<220> FEATURE:
<223> OTHER INFORMATION: Synthetic amino acid

<400> SEQUENCE: 47

Leu Gln Phe Gly Trp Trp Pro Pro Arg Thr
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic amino acid

<400> SEQUENCE: 48

Arg Ala Ser Asn Ser Val Val Ser Ser Tyr Leu Ala
1               5                   10

<210> SEQ ID NO 49
<211> LENGTH: 7
<212> TYPE: PRT
<213> ORGANISM: Artificial sequence
<220> FEATURE:
<223> OTHER INFORMATION: Synthetic amino acid

<400> SEQUENCE: 49

Gly Ala Ala Ser Arg Ala Asn
1               5

<210> SEQ ID NO 50
<211> LENGTH: 10
<212> TYPE: PRT
<213> ORGANISM: Artificial sequence
<220> FEATURE:
<223> OTHER INFORMATION: Synthetic amino acid
```

```
<400> SEQUENCE: 50

Val Gln Phe Gly Trp Trp Pro Pro Arg Thr
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic amino acid

<400> SEQUENCE: 51

Arg Ala Ser Gln Phe Val Tyr Ser Ser Asp Leu Ala
1               5                   10

<210> SEQ ID NO 52
<211> LENGTH: 7
<212> TYPE: PRT
<213> ORGANISM: Artificial sequence
<220> FEATURE:
<223> OTHER INFORMATION: Synthetic amino acid

<400> SEQUENCE: 52

Gly Ala Ser Ala Arg Ala Ala
1               5

<210> SEQ ID NO 53
<211> LENGTH: 10
<212> TYPE: PRT
<213> ORGANISM: Artificial sequence
<220> FEATURE:
<223> OTHER INFORMATION: Synthetic amino acid

<400> SEQUENCE: 53

Met Gln Phe Gly Trp Trp Pro Pro Arg Thr
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic amino acid

<400> SEQUENCE: 54

Arg Ala Ser His Ser Val Val Ser Ser Tyr Leu Ala
1               5                   10

<210> SEQ ID NO 55
<211> LENGTH: 7
<212> TYPE: PRT
<213> ORGANISM: Artificial sequence
<220> FEATURE:
<223> OTHER INFORMATION: Synthetic amino acid

<400> SEQUENCE: 55

Gly Ala Ser Ser Arg Glu Asp
1               5

<210> SEQ ID NO 56
<211> LENGTH: 10
<212> TYPE: PRT
<213> ORGANISM: Artificial sequence
<220> FEATURE:
<223> OTHER INFORMATION: Synthetic amino acid
```

```
<400> SEQUENCE: 56

Val Gln Phe Gly Trp Trp Pro Pro Arg Thr
1               5                   10

<210> SEQ ID NO 57
<211> LENGTH: 11
<212> TYPE: PRT
<213> ORGANISM: Artificial sequence
<220> FEATURE:
<223> OTHER INFORMATION: Synthetic amino acid

<400> SEQUENCE: 57

Arg Ala Ser Gln Gly Ile Ser Ser Trp Leu Ala
1               5                   10

<210> SEQ ID NO 58
<211> LENGTH: 7
<212> TYPE: PRT
<213> ORGANISM: Artificial sequence
<220> FEATURE:
<223> OTHER INFORMATION: Synthetic amino acid

<400> SEQUENCE: 58

Ala Ala Ser Ser Leu Gln Ser
1               5

<210> SEQ ID NO 59
<211> LENGTH: 9
<212> TYPE: PRT
<213> ORGANISM: Artificial sequence
<220> FEATURE:
<223> OTHER INFORMATION: Synthetic amino acid

<400> SEQUENCE: 59

Gln Gln Tyr Val Tyr Phe Pro Pro Thr
1               5

<210> SEQ ID NO 60
<211> LENGTH: 11
<212> TYPE: PRT
<213> ORGANISM: Artificial sequence
<220> FEATURE:
<223> OTHER INFORMATION: Synthetic amino acid

<400> SEQUENCE: 60

Gln Ala Ser Gln Asp Ile Ser Asn Tyr Leu Asn
1               5                   10

<210> SEQ ID NO 61
<211> LENGTH: 7
<212> TYPE: PRT
<213> ORGANISM: Artificial sequence
<220> FEATURE:
<223> OTHER INFORMATION: Synthetic amino acid

<400> SEQUENCE: 61

Asp Ala Ser Asn Leu Glu Thr
1               5

<210> SEQ ID NO 62
<211> LENGTH: 8
<212> TYPE: PRT
<213> ORGANISM: Artificial sequence
<220> FEATURE:
<223> OTHER INFORMATION: Synthetic amino acid

<400> SEQUENCE: 62
```

Gln Gln Pro Phe His Leu Ile Thr
1               5

<210> SEQ ID NO 63
<211> LENGTH: 120
<212> TYPE: PRT
<213> ORGANISM: Artificial sequence
<220> FEATURE:
<223> OTHER INFORMATION: Synthetic amino acid

<400> SEQUENCE: 63

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Pro Trp Ser Trp Ile Arg Gln Pro Pro Gly Lys Gly Leu Glu Trp Ile
        35                  40                  45

Gly Glu Thr Asp Val Ser Gly Trp Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Arg Arg Met Gly Thr Pro Ser Phe Asp Ile Trp Gly Gln
            100                 105                 110

Gly Thr Met Val Thr Val Ser Ser
        115                 120

<210> SEQ ID NO 64
<211> LENGTH: 107
<212> TYPE: PRT
<213> ORGANISM: Artificial sequence
<220> FEATURE:
<223> OTHER INFORMATION: Synthetic amino acid

<400> SEQUENCE: 64

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Phe
            20                  25                  30

Leu Ala Trp Tyr Gln Gln Lys Pro Gly Lys Ala Pro Lys Leu Leu Ile
        35                  40                  45

Tyr Ala Ala Ser Ser Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala Val Tyr Phe Pro Pro
                85                  90                  95

Thr Phe Gly Gly Gly Thr Lys Val Glu Ile Lys
            100                 105

<210> SEQ ID NO 65
<211> LENGTH: 107
<212> TYPE: PRT
<213> ORGANISM: Artificial sequence
<220> FEATURE:
<223> OTHER INFORMATION: Synthetic amino acid

<400> SEQUENCE: 65

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Phe
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala Val Tyr Phe Pro Pro
                85                  90                  95

Thr Phe Gly Gly Gly Thr Lys Val Glu Ile Lys
            100                 105

<210> SEQ ID NO 66
<211> LENGTH: 120
<212> TYPE: PRT
<213> ORGANISM: Artificial sequence
<220> FEATURE:
<223> OTHER INFORMATION: Synthetic amino acid

<400> SEQUENCE: 66

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Pro Trp Ser Trp Ile Arg Gln Pro Pro Gly Lys Gly Leu Glu Trp Ile
        35                  40                  45

Gly Glu Thr Asp Val Ser Gly Trp Thr Asp Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Arg Arg Met Gly Thr Pro Ser Phe Asp Ile Trp Gly Gln
            100                 105                 110

Gly Thr Met Val Thr Val Ser Ser
        115                 120

<210> SEQ ID NO 67
<211> LENGTH: 120
<212> TYPE: PRT
<213> ORGANISM: Artificial sequence
<220> FEATURE:
<223> OTHER INFORMATION: Synthetic amino acid

<400> SEQUENCE: 67

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Pro Trp Ser Trp Ile Arg Gln Pro Pro Gly Lys Gly Leu Glu Trp Ile
        35                  40                  45

Gly Glu Thr Asp Val Ser Gly Trp Thr Asp Tyr Asn Pro Ser Leu Lys
50                  55                  60

Ser Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg Asp Gly Arg Arg Met Gly Thr Pro Ser Phe Asp Ile Trp Gly Gln
            100                 105                 110

Gly Thr Met Val Thr Val Ser Ser
        115                 120

<210> SEQ ID NO 68
<211> LENGTH: 107
<212> TYPE: PRT
<213> ORGANISM: Artificial sequence
<220> FEATURE:
<223> OTHER INFORMATION: Synthetic amino acid

<400> SEQUENCE: 68

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Phe
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ser Val Tyr Phe Pro Pro
                85                  90                  95

Thr Phe Gly Gly Gly Thr Lys Val Glu Ile Lys
            100                 105

<210> SEQ ID NO 69
<211> LENGTH: 120
<212> TYPE: PRT
<213> ORGANISM: Artificial sequence
<220> FEATURE:
<223> OTHER INFORMATION: Synthetic amino acid

<400> SEQUENCE: 69

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Pro Trp Ser Trp Ile Arg Gln Pro Pro Gly Lys Gly Leu Glu Trp Ile
        35                  40                  45

Gly Glu Thr Asp Val Ser Gly Trp Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Arg Arg Met Gly Thr Pro Ser Phe Asp Ile Trp Gly Gln
            100                 105                 110

Gly Thr Met Val Thr Val Ser Ser
        115                 120

<210> SEQ ID NO 70
<211> LENGTH: 107
<212> TYPE: PRT
```

<213> ORGANISM: Artificial sequence
<220> FEATURE:
<223> OTHER INFORMATION: Synthetic amino acid

<400> SEQUENCE: 70

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Phe
            20                  25                  30

Leu Ala Trp Tyr Gln Gln Lys Pro Gly Lys Ala Pro Lys Leu Leu Ile
        35                  40                  45

Tyr Ala Ala Ser Ala Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ala Val Tyr Phe Pro Pro
                85                  90                  95

Thr Phe Gly Gly Gly Thr Lys Val Glu Ile Lys
            100                 105
```

<210> SEQ ID NO 71
<211> LENGTH: 120
<212> TYPE: PRT
<213> ORGANISM: Artificial sequence
<220> FEATURE:
<223> OTHER INFORMATION: Synthetic amino acid

<400> SEQUENCE: 71

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Pro Trp Ser Trp Ile Arg Gln Pro Pro Gly Lys Gly Leu Glu Trp Ile
        35                  40                  45

Gly Glu Thr Asp Val Ser Gly Trp Thr Asp Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Arg Arg Met Gly Thr Pro Ser Phe Asp Ile Trp Gly Gln
            100                 105                 110

Gly Thr Met Val Thr Val Ser Ser
        115                 120
```

<210> SEQ ID NO 72
<211> LENGTH: 9
<212> TYPE: PRT
<213> ORGANISM: Artificial sequence
<220> FEATURE:
<223> OTHER INFORMATION: Synthetic amino acid

<400> SEQUENCE: 72

```
Gly Ser Leu Ser Gly Tyr Pro Trp Ser
1               5
```

<210> SEQ ID NO 73
<211> LENGTH: 16
<212> TYPE: PRT
<213> ORGANISM: Artificial sequence

```
<220> FEATURE:
<223> OTHER INFORMATION: Synthetic amino acid

<400> SEQUENCE: 73

Glu Thr Asp Val Ser Gly Trp Thr Asp Tyr Asn Pro Ser Leu Lys Ser
1               5                   10                  15

<210> SEQ ID NO 74
<211> LENGTH: 14
<212> TYPE: PRT
<213> ORGANISM: Artificial sequence
<220> FEATURE:
<223> OTHER INFORMATION: Synthetic amino acid

<400> SEQUENCE: 74

Ala Arg Asp Gly Arg Arg Met Gly Thr Pro Ser Phe Asp Ile
1               5                   10

<210> SEQ ID NO 75
<211> LENGTH: 9
<212> TYPE: PRT
<213> ORGANISM: Artificial sequence
<220> FEATURE:
<223> OTHER INFORMATION: Synthetic amino acid

<400> SEQUENCE: 75

Gly Ser Leu Ser Gly Tyr Pro Trp Ser
1               5

<210> SEQ ID NO 76
<211> LENGTH: 16
<212> TYPE: PRT
<213> ORGANISM: Artificial sequence
<220> FEATURE:
<223> OTHER INFORMATION: Synthetic amino acid

<400> SEQUENCE: 76

Glu Thr Asp Val Ser Gly Trp Thr Asp Tyr Asn Pro Ser Leu Lys Ser
1               5                   10                  15

<210> SEQ ID NO 77
<211> LENGTH: 14
<212> TYPE: PRT
<213> ORGANISM: Artificial sequence
<220> FEATURE:
<223> OTHER INFORMATION: Synthetic amino acid

<400> SEQUENCE: 77

Ala Arg Asp Gly Arg Arg Met Gly Thr Pro Ser Phe Asp Ile
1               5                   10

<210> SEQ ID NO 78
<211> LENGTH: 9
<212> TYPE: PRT
<213> ORGANISM: Artificial sequence
<220> FEATURE:
<223> OTHER INFORMATION: Synthetic amino acid

<400> SEQUENCE: 78

Gly Ser Leu Ser Gly Tyr Pro Trp Ser
1               5

<210> SEQ ID NO 79
<211> LENGTH: 16
<212> TYPE: PRT
<213> ORGANISM: Artificial sequence
<220> FEATURE:
```

<223> OTHER INFORMATION: Synthetic amino acid

<400> SEQUENCE: 79

Glu Thr Asp Val Ser Gly Trp Thr Asp Tyr Asn Pro Ser Leu Lys Ser
1               5                   10                  15

<210> SEQ ID NO 80
<211> LENGTH: 14
<212> TYPE: PRT
<213> ORGANISM: Artificial sequence
<220> FEATURE:
<223> OTHER INFORMATION: Synthetic amino acid

<400> SEQUENCE: 80

Ala Arg Asp Gly Arg Arg Met Gly Thr Pro Ser Phe Asp Ile
1               5                   10

<210> SEQ ID NO 81
<211> LENGTH: 9
<212> TYPE: PRT
<213> ORGANISM: Artificial sequence
<220> FEATURE:
<223> OTHER INFORMATION: Synthetic amino acid

<400> SEQUENCE: 81

Gly Ser Leu Ser Gly Tyr Pro Trp Ser
1               5

<210> SEQ ID NO 82
<211> LENGTH: 16
<212> TYPE: PRT
<213> ORGANISM: Artificial sequence
<220> FEATURE:
<223> OTHER INFORMATION: Synthetic amino acid

<400> SEQUENCE: 82

Glu Thr Asp Val Ser Gly Trp Thr Asp Tyr Asn Pro Ser Leu Lys Ser
1               5                   10                  15

<210> SEQ ID NO 83
<211> LENGTH: 14
<212> TYPE: PRT
<213> ORGANISM: Artificial sequence
<220> FEATURE:
<223> OTHER INFORMATION: Synthetic amino acid

<400> SEQUENCE: 83

Ala Arg Asp Gly Arg Arg Met Gly Thr Pro Ser Phe Asp Ile
1               5                   10

<210> SEQ ID NO 84
<211> LENGTH: 9
<212> TYPE: PRT
<213> ORGANISM: Artificial sequence
<220> FEATURE:
<223> OTHER INFORMATION: Synthetic amino acid

<400> SEQUENCE: 84

Gly Ser Leu Ser Gly Tyr Pro Trp Ser
1               5

<210> SEQ ID NO 85
<211> LENGTH: 16
<212> TYPE: PRT
<213> ORGANISM: Artificial sequence
<220> FEATURE:
<223> OTHER INFORMATION: Synthetic amino acid

```
<400> SEQUENCE: 85

Glu Thr Asp Val Ser Gly Trp Thr Asp Tyr Asn Pro Ser Leu Lys Ser
1               5                   10                  15

<210> SEQ ID NO 86
<211> LENGTH: 14
<212> TYPE: PRT
<213> ORGANISM: Artificial sequence
<220> FEATURE:
<223> OTHER INFORMATION: Synthetic amino acid

<400> SEQUENCE: 86

Ala Arg Asp Gly Arg Arg Met Gly Thr Pro Ser Phe Asp Ile
1               5                   10

<210> SEQ ID NO 87
<211> LENGTH: 11
<212> TYPE: PRT
<213> ORGANISM: Artificial sequence
<220> FEATURE:
<223> OTHER INFORMATION: Synthetic amino acid

<400> SEQUENCE: 87

Arg Ala Ser Gln Gly Ile Asn Ser Phe Leu Ala
1               5                   10

<210> SEQ ID NO 88
<211> LENGTH: 7
<212> TYPE: PRT
<213> ORGANISM: Artificial sequence
<220> FEATURE:
<223> OTHER INFORMATION: Synthetic amino acid

<400> SEQUENCE: 88

Ala Ala Ser Ser Leu Asn Ser
1               5

<210> SEQ ID NO 89
<211> LENGTH: 9
<212> TYPE: PRT
<213> ORGANISM: Artificial sequence
<220> FEATURE:
<223> OTHER INFORMATION: Synthetic amino acid

<400> SEQUENCE: 89

Gln Lys Ala Val Tyr Phe Pro Pro Thr
1               5

<210> SEQ ID NO 90
<211> LENGTH: 11
<212> TYPE: PRT
<213> ORGANISM: Artificial sequence
<220> FEATURE:
<223> OTHER INFORMATION: Synthetic amino acid

<400> SEQUENCE: 90

Arg Ala Ser Gln Gly Ile Ser Asn Phe Leu Ala
1               5                   10

<210> SEQ ID NO 91
<211> LENGTH: 7
<212> TYPE: PRT
<213> ORGANISM: Artificial sequence
<220> FEATURE:
<223> OTHER INFORMATION: Synthetic amino acid
```

```
<400> SEQUENCE: 91

Ala Ala Ser Ser Leu Gln Ser
1               5

<210> SEQ ID NO 92
<211> LENGTH: 9
<212> TYPE: PRT
<213> ORGANISM: Artificial sequence
<220> FEATURE:
<223> OTHER INFORMATION: Synthetic amino acid

<400> SEQUENCE: 92

Gln Lys Ala Val Tyr Phe Pro Pro Thr
1               5

<210> SEQ ID NO 93
<211> LENGTH: 11
<212> TYPE: PRT
<213> ORGANISM: Artificial sequence
<220> FEATURE:
<223> OTHER INFORMATION: Synthetic amino acid

<400> SEQUENCE: 93

Arg Ala Ser Gln Asp Ile Ser Ser Phe Leu Ala
1               5                   10

<210> SEQ ID NO 94
<211> LENGTH: 7
<212> TYPE: PRT
<213> ORGANISM: Artificial sequence
<220> FEATURE:
<223> OTHER INFORMATION: Synthetic amino acid

<400> SEQUENCE: 94

Ala Ala Ser Ser Leu Gln Asp
1               5

<210> SEQ ID NO 95
<211> LENGTH: 9
<212> TYPE: PRT
<213> ORGANISM: Artificial sequence
<220> FEATURE:
<223> OTHER INFORMATION: Synthetic amino acid

<400> SEQUENCE: 95

Gln Lys Ser Val Tyr Phe Pro Pro Thr
1               5

<210> SEQ ID NO 96
<211> LENGTH: 11
<212> TYPE: PRT
<213> ORGANISM: Artificial sequence
<220> FEATURE:
<223> OTHER INFORMATION: Synthetic amino acid

<400> SEQUENCE: 96

Arg Ala Ser Gln Gly Ile Ser Thr Phe Leu Ala
1               5                   10

<210> SEQ ID NO 97
<211> LENGTH: 7
<212> TYPE: PRT
<213> ORGANISM: Artificial sequence
<220> FEATURE:
<223> OTHER INFORMATION: Synthetic amino acid

<400> SEQUENCE: 97
```

```
Ala Ala Ser Ala Leu His Ser
1               5

<210> SEQ ID NO 98
<211> LENGTH: 9
<212> TYPE: PRT
<213> ORGANISM: Artificial sequence
<220> FEATURE:
<223> OTHER INFORMATION: Synthetic amino acid

<400> SEQUENCE: 98

Gln Arg Ala Val Tyr Phe Pro Pro Thr
1               5

<210> SEQ ID NO 99
<211> LENGTH: 11
<212> TYPE: PRT
<213> ORGANISM: Artificial sequence
<220> FEATURE:
<223> OTHER INFORMATION: Synthetic amino acid

<400> SEQUENCE: 99

Arg Ala Ser Lys Gly Ile Ser Ser Phe Leu Ala
1               5                   10

<210> SEQ ID NO 100
<211> LENGTH: 7
<212> TYPE: PRT
<213> ORGANISM: Artificial sequence
<220> FEATURE:
<223> OTHER INFORMATION: Synthetic amino acid

<400> SEQUENCE: 100

Ala Ala Asp Ser Ile Gln Ser
1               5

<210> SEQ ID NO 101
<211> LENGTH: 9
<212> TYPE: PRT
<213> ORGANISM: Artificial sequence
<220> FEATURE:
<223> OTHER INFORMATION: Synthetic amino acid

<400> SEQUENCE: 101

Gln Ser Ala Val Tyr Phe Pro Pro Thr
1               5
```

DUAL SPECIFICITY ANTIBODIES TO HUMAN PD-L1 AND PD-L2 AND METHODS OF USE THEREFOR

PRIORITY CLAIM

This application is a national phase application under 35 U.S.C. § 371 of International Application No. PCT/US2019/022295, filed Mar. 14, 2019, which claims benefit of priority to U.S. Provisional Application Ser. No. 62/647,407 filed Mar. 23, 2018 and U.S. Provisional Application Ser. No. 62/755,408 filed Nov. 2, 2018, respectively, the entire contents of each application being hereby incorporated by reference.

INCORPORATION OF SEQUENCE LISTING

The sequence listing that is contained in the file named "UTFC_P1338WO_ST25" which is 49 KB and was created on Mar. 14, 2019, is filed herewith by electronic submission and is incorporated by reference herein.

BACKGROUND

1. Field

The present disclosure relates generally to the field of medicine, oncology, and immunology. More particularly, it concerns bispecific human antibodies binding to PD-L1 and PD-L2 and their use in cancer therapies.

2. Description of Related Art

Blockade of the interaction of the T cell co-inhibitory receptor PD-1 with its ligand PD-L1 has become a pillar of modern oncology now available even in the first-line setting for subsets of melanoma and lung cancer patients (Boussiotis, 2016). Numerous antibodies targeting PD-1 or PD-L1 are currently FDA approved or in clinical trials; however, no agents targeting the second PD-1 ligand, PD-L2, are under clinical investigation. PD-L2 binds PD-1 with an approximately 3-fold higher affinity than does PD-L1, and, like PD-L1, sends an inhibitory signal which attenuates T cell function (Cheng et al., 2013; Latchman et al., 2001; Lee et al., 2016; Li et al., 2017; Youngnak et al., 2003). Historically, PD-L2 was considered to be largely an inducible co-inhibitory molecule with expression limited to the tumor stroma; however, improved detection reagents for PD-L2 have revealed widespread PD-L2 expression both in the tumor microenvironment and on tumor cells themselves (Baptista et al., 2016; Danilova et al., 2016; Derks et al., 2015; Dong et al., 2016; Howitt et al., 2016; Kim et al., 2015; Kim et al., 2015; Nomi et al., 2007; Obeid et al., 2016; Ohigashi et al., 2005; Roemer et al., 2016; Shi et al., 2014; Shin et al., 2015; Xu et al., 2016). Recently, PD-L2 was shown to be an independent predictor of response to the PD-1 antibody pembrolizumab across multiple cancers (Yearley et al., 2017).

First described in the vast majority of classical Hodgkin's Lymphoma (cHL), amplification of chromosomal region 9p24.1 leads to direct upregulation of PD-L1 and PD-L2 (which reside therein), as well as indirect induction via enhanced JAK2 activity (Roemer et al., 2016; Shi et al., 2014; Green et al., 2010; Van Roosbroeck et al., 2016). In addition to cHL, this genetic driver of high PD-L1/PD-L2 co-expression is also found in the majority of Primary Mediastinal Large B-Cell Lymphoma (PMBL), T cell lymphoma, and a variety of histiocytic and dendritic cell malignancies. Not surprisingly, many of these cancers have been shown to respond to PD-1 blockade. More recently, 9p24.1 amplification has been demonstrated in solid tumors such as triple-negative breast cancer (TNBC) (Howitt et al., 2016; Barrett et al., 2015). Relatively high co-expression of PD-L1 and PD-L2 has also been observed in a number of other cancers such as gastric carcinoma, melanoma, squamous carcinomas of the lung, head and neck, cervix and vulva, bladder cancer, and hepatocellular carcinoma among others (Baptista et al., 2016; Danilova et al., 2016; Derks et al., 2015; Dong et al., 2016; Howitt et al., 2016; Kim et al., 2015; Nomi et al., 2007; Obeid et al., 2016; Xu et al., 2016; Yearley et al., 2017; Van Roosbroeck et al., 2016; Barrett et al., 2015; Shin et al., 2016; Inoue et al., 2016; Wang et al., 2011). In addition to expression by these tumors themselves, stromal and endothelial expression of PD-L2 has also been documented for many of these tumors (Yearley et al., 2017). These findings suggest limitations to the therapeutic potential of PD-L1 blockade in these cancers.

The PD-1 co-inhibitory receptor is expressed primarily by activated T cells and NK cells and can thus best be targeted by antibodies which bind it and prevent engagement by PD-ligands. PD-L1, in contrast, is expressed by tumor cells and suppressive stromal populations and can be targeted with antibodies capable of cytotoxic effector function. While the theoretical advantages of these antibody-dependent cellular cytotoxicity (ADCC) capable PD-L1 antibodies can be demonstrated in vitro, no patient data exists demonstrating actual effector function in patients or improved outcome relative to purely blocking variants (Boyerinas et al., 2015).

PD-L1 and PD-L2 share only approximately 40% identity, as each binds an additional receptor distinct from PD-1 (Latchman et al., 2001). PD-L1 also binds B7-1 in an additional negative T cell regulatory interaction (Butte et al., 2007; Butte et al., 2008). In mice, PD-L2 can bind to RGMb on either myeloid cells or T cells and regulate tolerance to inhaled antigens (Xiao et al., 2014; Nie et al., 2017). The role of PD-L2 binding to RGMb in tumors remains to be described, as does the relevance of this interaction in humans. It could prove extremely advantageous from a therapeutic standpoint to have bispecific antibodies to PD-L1 and PD-L2.

SUMMARY

Thus, in accordance with the present disclosure, there is provided an antibody or antibody fragment that binds selectively to both PD-L1 and PD-L2 and having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% or greater identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% or greater identity to clone-paired sequences from Table 2.

There is also provided a method of treating cancer in a subject comprising contacting a PD-L1- or PD-L2-positive cancer cell in a subject with an antibody as described above. The PD-L1- or PD-L2-positive cancer cell may be a solid tumor cell, such as a lung cancer cell, brain cancer cell, head & neck cancer cell, breast cancer cell, skin cancer cell, liver cancer cell, pancreatic cancer cell, stomach cancer cell, colon cancer cell, rectal cancer cell, uterine cancer cell, cervical cancer cell, ovarian cancer cell, testicular cancer cell, skin cancer cell, esophageal cancer cell, a lymphoma cell, a renal cell carcinoma cell, or may be a leukemia or myeloma such as acute myeloid leukemia, chronic myelogenous leukemia or multiple myeloma.

The method may further comprise contacting the PD-L1- or PD-L2-positive cancer cell with a second anti-cancer agent or treatment, such as chemotherapy, radiotherapy, immunotherapy, hormonal therapy, or toxin therapy. The second anti-cancer agent or treatment may inhibit an intracellular PD-L1 or PD-L2 function. The second anti-cancer agent or treatment may be given at the same time as the first agent, or given before and/or after the agent. The PD-L1- or PD-L2-positive cancer cell may be a metastatic cancer cell, a multiply drug resistant cancer cell or a recurrent cancer cell.

The antibody may be a single chain antibody, a single domain antibody, a chimeric antibody, or a Fab fragment. The antibody may be a human antibody, murine antibody, an IgG, a humanized antibody or a humanized IgG. The antibody or antibody fragment may further comprise a label, such as a peptide tag, an enzyme, a magnetic particle, a chromophore, a fluorescent molecule, a chemiluminescent molecule, or a dye. The antibody or antibody fragment may further comprise an antitumor drug linked thereto, such as linked to the antibody or antibody fragment through a photolabile linker or an enzymatically-cleaved linker. The antitumor drug may be a toxin, a radioisotope, a cytokine or an enzyme. The antibody or antibody fragment may be conjugated to a nanoparticle or a liposome.

In another embodiment, there is provided a method of treating a cancer in a subject comprising delivering to the subject an antibody or antibody fragment having clone-paired heavy and light chain CDR sequences from Tables 3 and 4, respectively. The antibody fragment may be a recombinant scFv (single chain fragment variable) antibody, Fab fragment, F(ab')$_2$ fragment, or Fv fragment. The antibody may be an IgG. The antibody may be is a chimeric antibody. Delivering may comprise antibody or antibody fragment administration, or genetic delivery with an RNA or DNA sequence or vector encoding the antibody or antibody fragment.

The antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

Also provided is a monoclonal antibody, wherein the antibody or antibody fragment is characterized by clone-paired heavy and light chain CDR sequences from Tables 3 and 4, respectively. The antibody fragment may be a recombinant scFv (single chain fragment variable) antibody, Fab fragment, F(ab')2 fragment, or Fv fragment. The antibody may be a chimeric antibody, or an IgG.

The antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

In yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody fragment may be a recombinant scFv (single chain fragment variable) antibody, Fab fragment, F(ab')2 fragment, or Fv fragment. The antibody may be a chimeric antibody or an IgG The antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

A further embodiment comprises a cancer vaccine comprising one or more antibodies or antibody fragments characterized by clone-paired heavy and light chain CDR sequences from Tables 3 and 4, respectively. At least one antibody fragment may be a recombinant scFv (single chain fragment variable) antibody, Fab fragment, F(ab')2 fragment, or Fv fragment. At least one of antibody may be a chimeric antibody, or an IgG. At least one antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. At least one antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

In another embodiment there is provided a method of detecting PD-L1 or PD-L2 expressing cells in a subject comprising contacting a sample from said subject with an antibody or antibody fragment characterized by clone-paired heavy and light chain CDR sequences from Tables 3 and 4, respectively, and detecting a PD-L1 or PD-L2 expressing cell in said sample by binding said antibody or antibody fragment to a cell in said sample. The sample may be a body fluid or a tissue sample. The cell may be a cancer cell, such as a lymphoma cell, breast cancer cell, or renal cell carcinoma cell. The cell may be a cell associated with immune suppression. The cell associated with immune suppression may be a non-cancerous cell in a tumor microenvironment, such as a stromal cell or endothelial cell. Detection may comprise ELISA, RIA, or Western blot. The method may further comprise performing the method a second time and determining a change in orthopoxyvirus antigen levels as compared to the first assay. The antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1C—Identification of bispecific PD-L1/PD-L2 (BiPDL) antibodies to block PD-L1/PD-L2 binding to PD-1. Antibody candidates identified as described in the Examples were tested for the capacity to bind PD-L1 or PD-L2 and block their binding to PD-1. 5 μg/mL of antibody was bound to CHO-PD-L1 or CHO-PD-L2 cells and then recombinant PD-1 labelled with Alexa Fluor® 532 was added for 1 hour. (FIG. 1A) The percentage of PD-1+ cells is shown. (FIG. 1B) Maximum fluorescence intensity of Alexa Fluor® 532 labeled PD-1 was measured, with PD-L1 or PD-L2 blocking viewed as a reduction in Alexa532 fluorescence in FACS analysis. BiPDL antibody clones 1-4, (ADI-16413, -16414, -16415, and -16418) were evaluated against unstained cells, control antibodies, Durvalumab (anti-PD-L1), and a commercially available anti-PD-L2 antibody. (FIG. 1C) Candidate BiPDL monoclonal antibodies were assayed using the Promega® PD-L1:PD-1 blockade system.

FIGS. 2A-2D—Identification of bispecific antibody subclones which bind PD-L1 and PD-L2. Subclones of bispecific antibodies BiPDL3 or BiPDL4 were assayed for binding to CHO-PD-L1 (FIGS. 2A and 2C) or CHO-PD-L2 cells (FIGS. 2B and 2D). The indicated concentrations of BiPDL (human IgG1) antibodies were added to the indicated cells and binding was detected by addition of anti-human IgG1 secondary antibody conjugated to PE. Reactions were performed on the ForteBio Octet® platform.

FIG. 3—Evaluation of bispecific antibodies compared to FDA approved antibody therapeutics. Candidate BiPDL monoclonal antibodies were assayed using both the Promega® PD-L1:PD-1 blockade system and the PD-L2:PD-1 blockade system. Varying concentrations of antibody were added to CHO-PD-L1 or CHO-PD-L2 (CHO-PD-L1/2) cells capable of stimulating Jurkat T cells stably expressing PD-1. When co-cultured, the interaction between CHO-PD-L1/2 cells and Jurkat T cells inhibits luminescence. Upon disruption of that activation by the addition of PD-L1, PD-L2, PD-1, or BiPDL antibodies, luminescence is induced. The Jurkat T cells were incubated with antibodies the specified antibodies at the concentrations indicated and CHO-PD-L1/2 cells for 6 hours. Results were generated using the Bio-Glo™ (Fluorescein) assay kit (Promega®).

FIGS. 4A-4F—Evaluation of second, third, and fourth generation BiPDL antibodies. Candidate second generation (FIGS. 4A-B), third generation (FIGS. 4C-D), and fourth generation (FIGS. 4E-F) BiPDL monoclonal antibodies were again assayed using the Promega® PD-L1/PD-L2:PD-1 blockade system. Keytruda® (pembrolizumab) was used as a positive control anti-PD-L2 antibody (FIGS. 4B-D), while Durvalumab was used as a control anti-PD-L1 antibody (FIGS. 4C-D). Promega®'s control mAb against PD-1 was also used as a control (FIGS. 4C-D).

FIGS. 5A-5C—Candidate BiPDL antibodies are active across multiple human mixed lymphocyte reactions. Candidate antibodies, FDA approved antibodies, or control antibodies were evaluated in the presence of induced dendritic cells and T-cells from separate donors and evaluated by ELISA for IL-2 or IFN-γ production. (FIG. 5A) Magnetically-sorted iDCs were analyzed by flow cytometry for expression of human PD-L1 and PD-L2. (FIG. 5B)

Keytruda® (pembrolizumab) (anti-PD-1), Atezolizumab (anti-PD-L1), a 4th generation BiPDL antibody, and an isotype control were added to the IDCs prior to addition to CD4+ T cells. (FIG. 5C) A different 4th generation BiPDL antibody was evaluated alongside Atezolizumab and an isotype control. Each was added to the IDCs prior to addition to CD4+ T cells.

FIG. 6—BiPDL Antibodies Mediate Efficient ADCC Against Human PD-L1/PD-L2+ Lymphoma. Varying concentrations of BiPDL antibodies (mouse IgG2a) were added with in vitro expanded murine NK cells to Calcein-labelled U2940 PMBL cells at an effector to target ratio of 15 to 1. Percent specific lysis was calculated as the difference between experimental release and spontaneous release of Calcein as measured on a fluorescent plate reader.

Figure 7A:
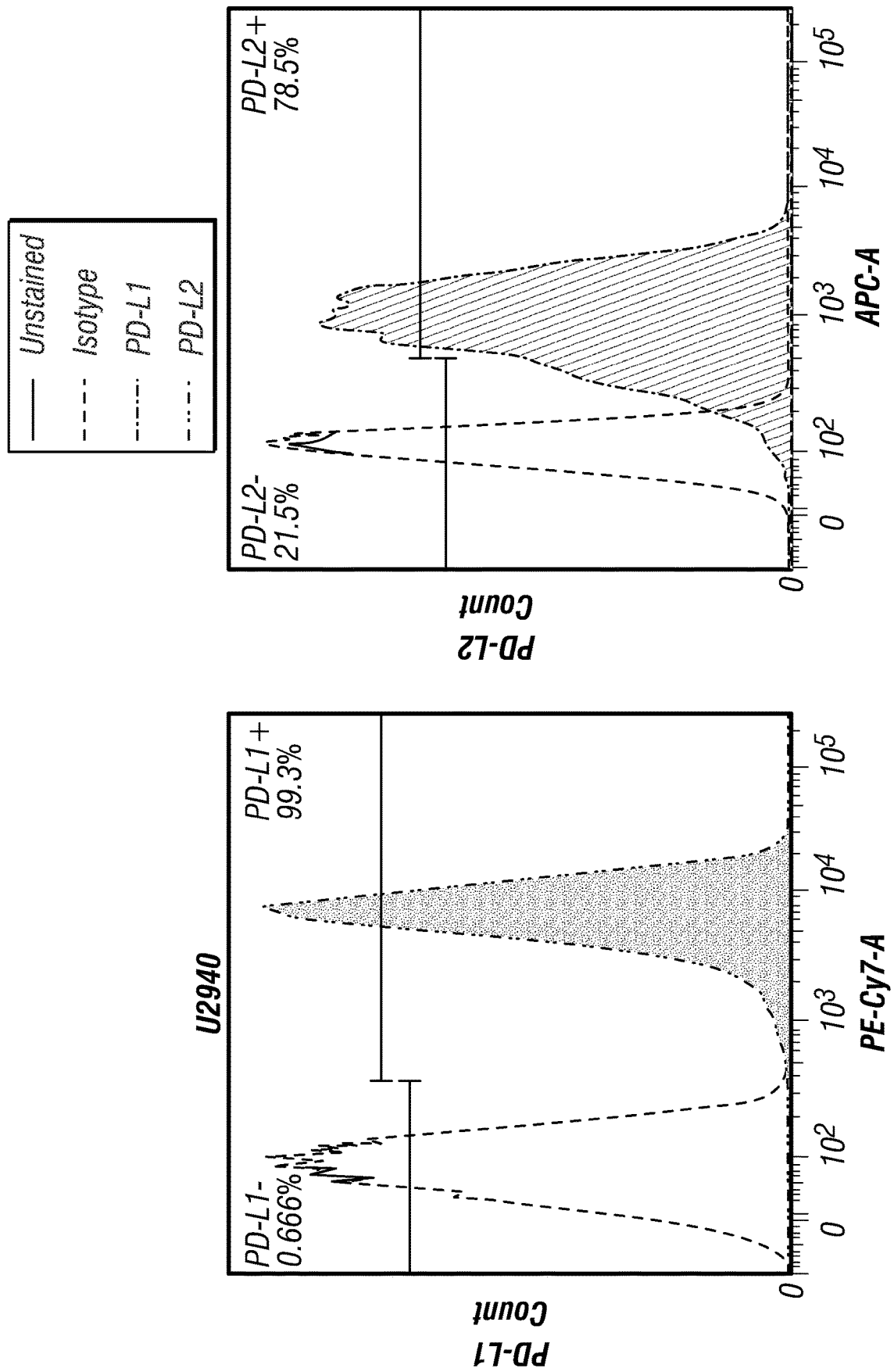
Figure 7B:
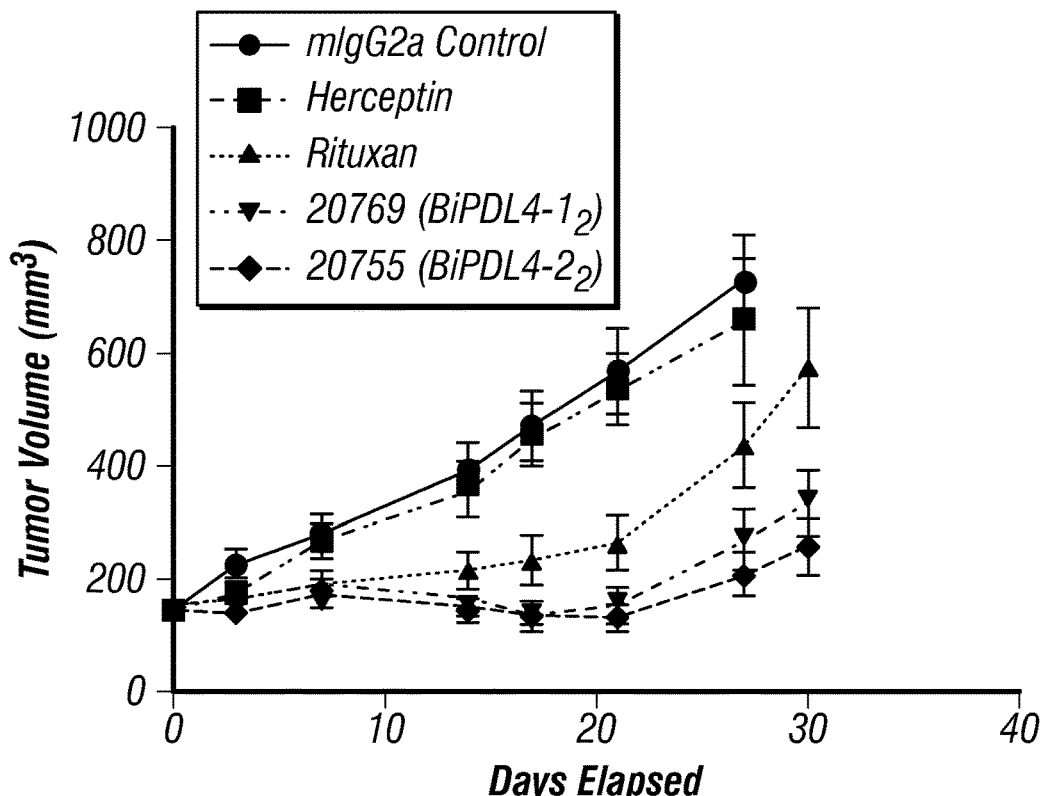
Figure 7C:
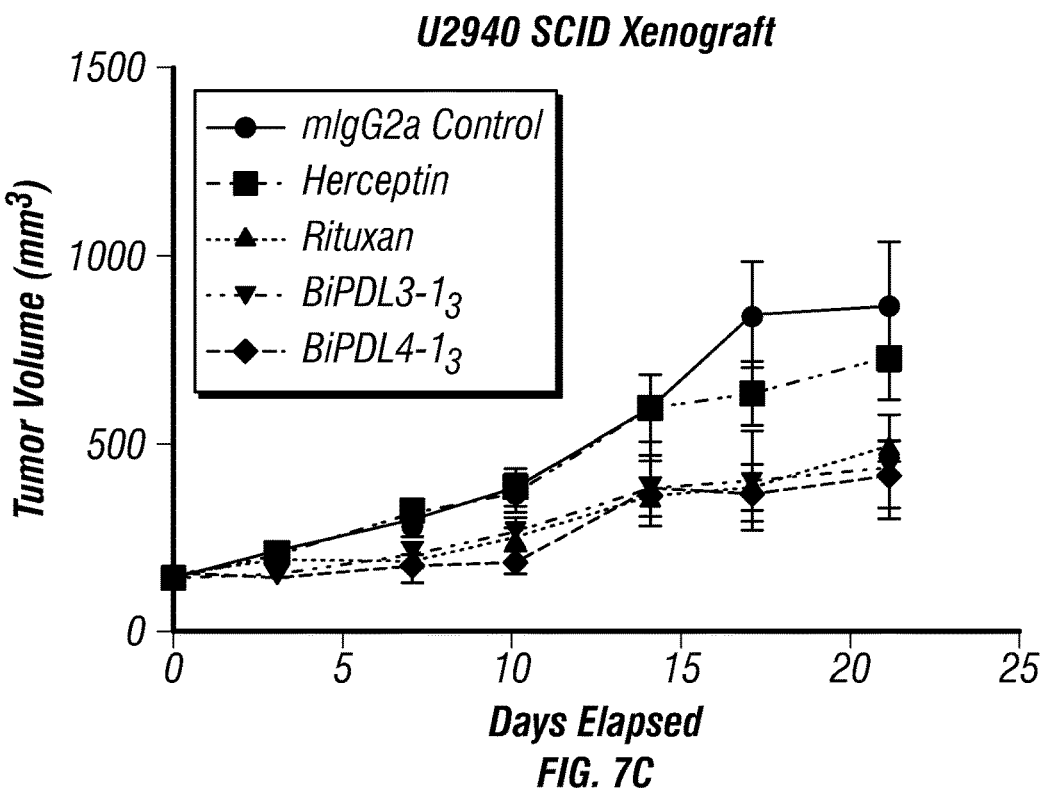

FIGS. 7A-7C-Candidate antibodies with ADCC are highly active against human U2940 lymphoma in vivo. PBML xenograft tumors were established in SCID mice and allowed to reach 150 mm3. (FIG. 7A) Cells were analyzed for PD-L1 or PD-L2 expression by flow cytometry. (FIGS. 7B-C) Mice were treated with either mIgG2a control antibodies, Herceptin® trastuzumab), Rituxan® (rituximab), or the indicated BiPDL antibodies 2×/week at 10 mg/kg for 3 weeks, and tumor volume was assessed by caliper on the indicated days.

Figure 8A:
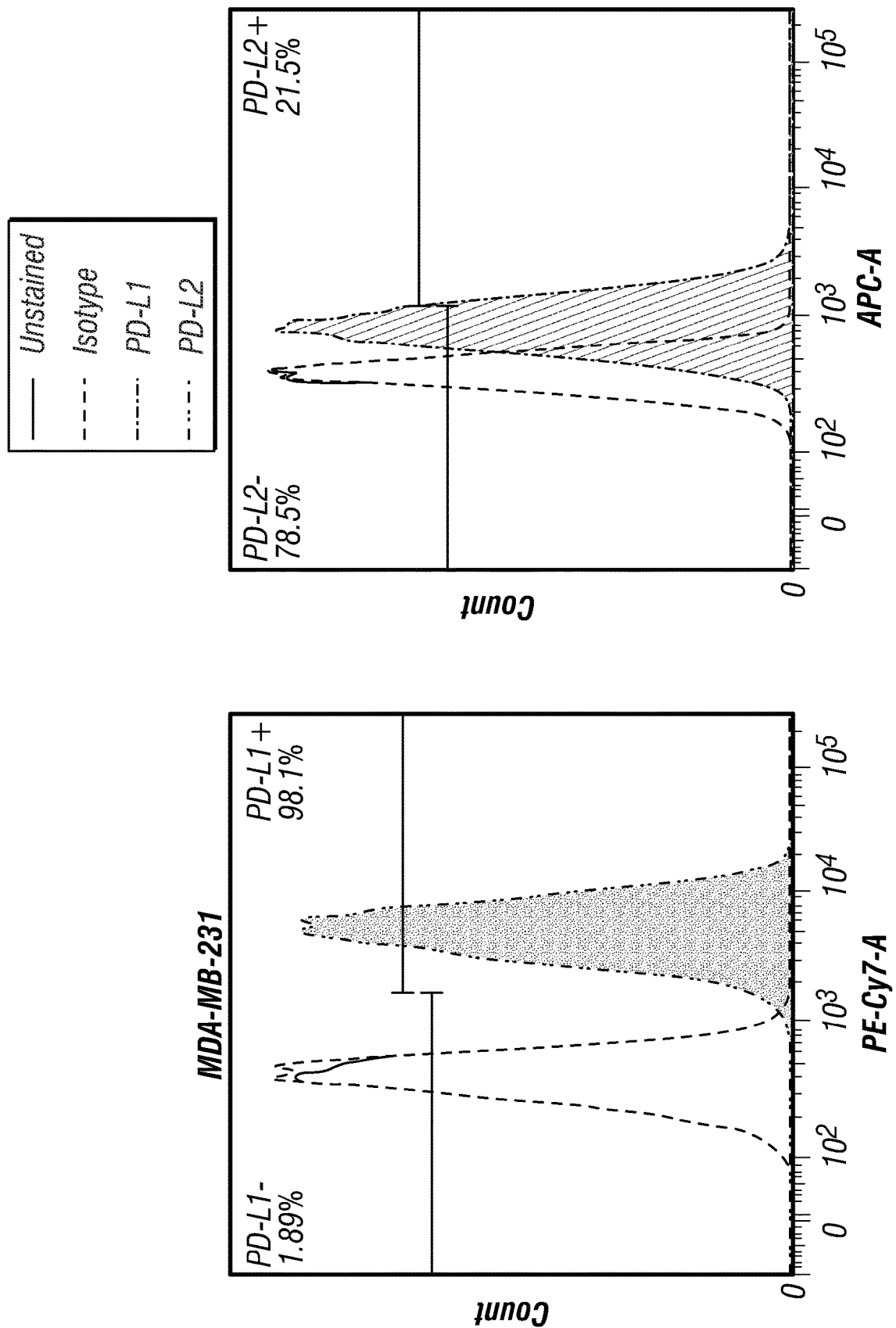
Figure 8B:
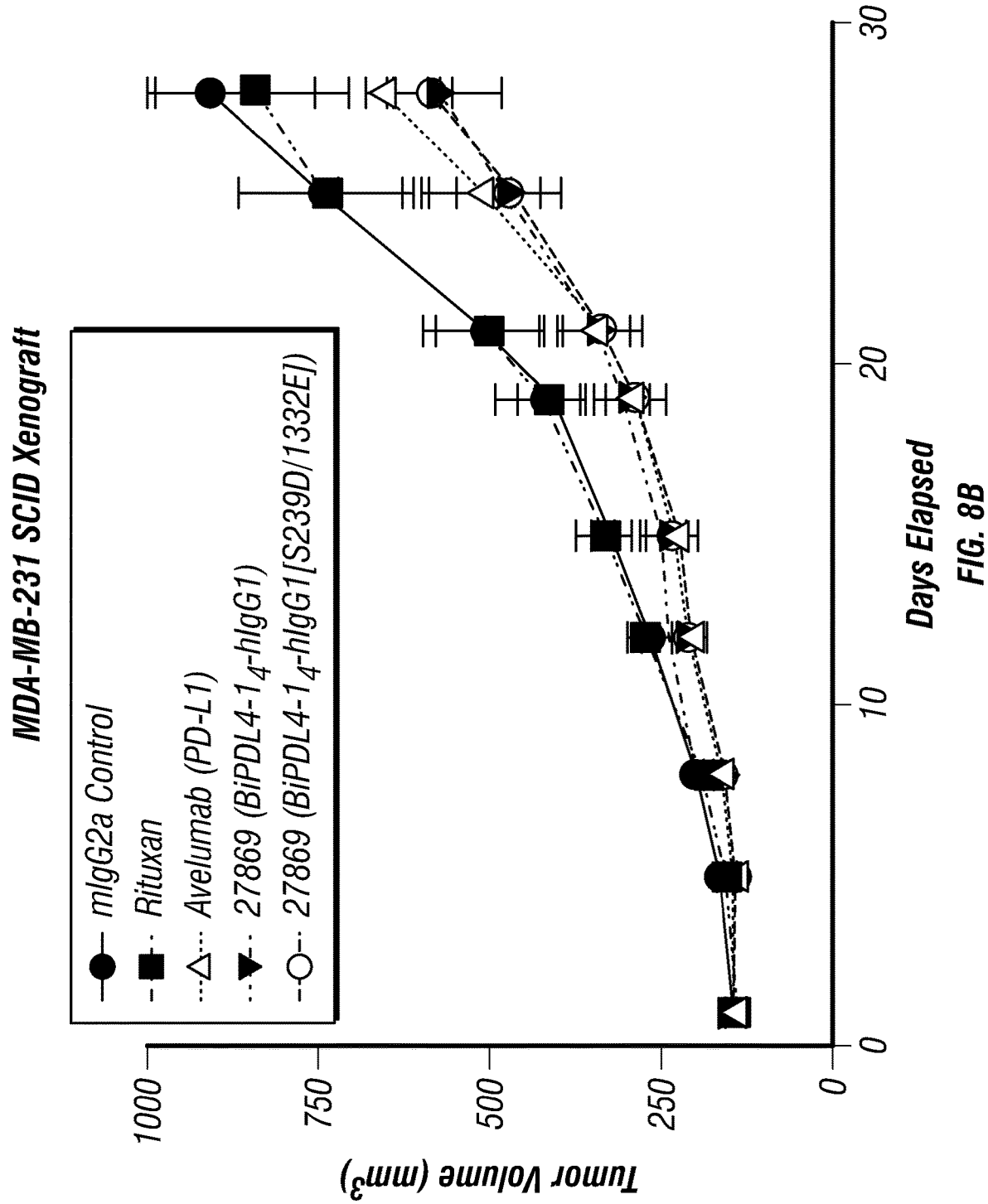

FIGS. 8A-8B—Candidate antibodies are active against MDA-MB-231. MDA-MB-231 triple-negative breast cancer xenograft tumors were established in SCID mice and allowed to reach 150 mm$^3$. (FIG. 8A) Cells were analyzed for PD-L1 or PD-L2 expression by flow cytometry. (FIG. 8B) The mice were then treated with the indicated antibody 2×/week at 10 mg/kg for 3 weeks. Data shown is from a single experiment with 9 mice per group, and tumor volume was assessed on the indicated days.

Figure 9A:
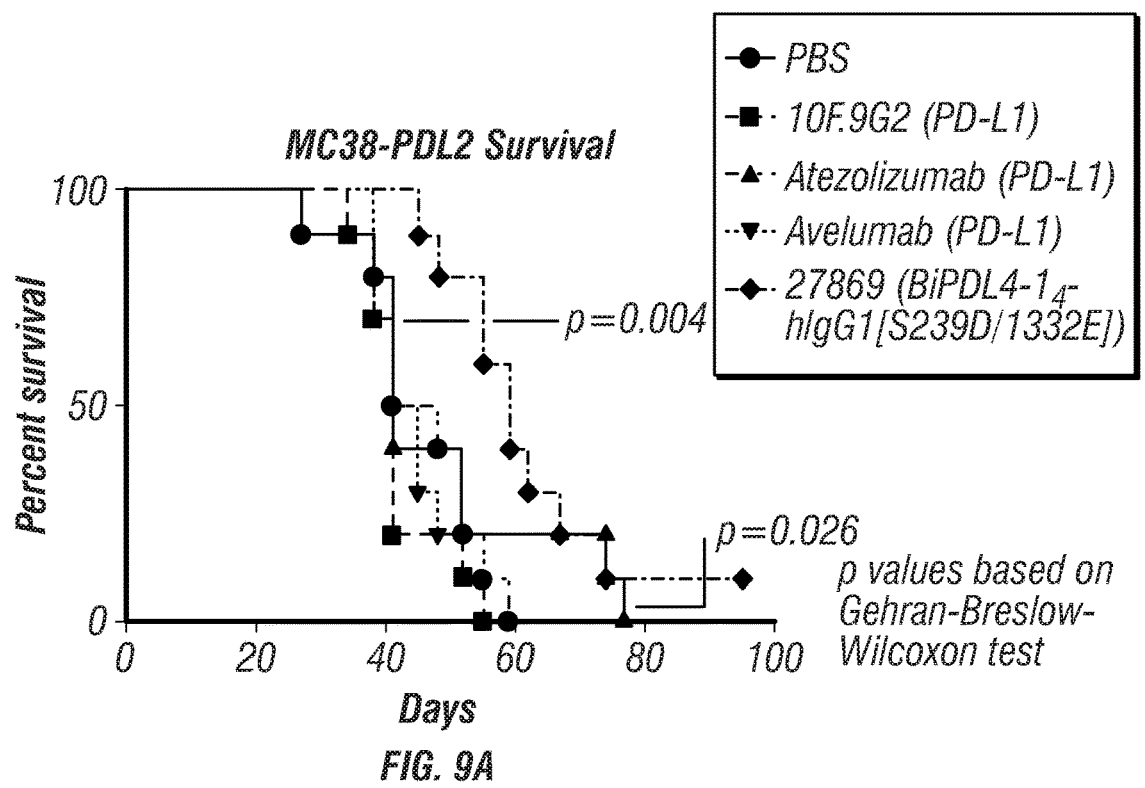
Figure 9B:
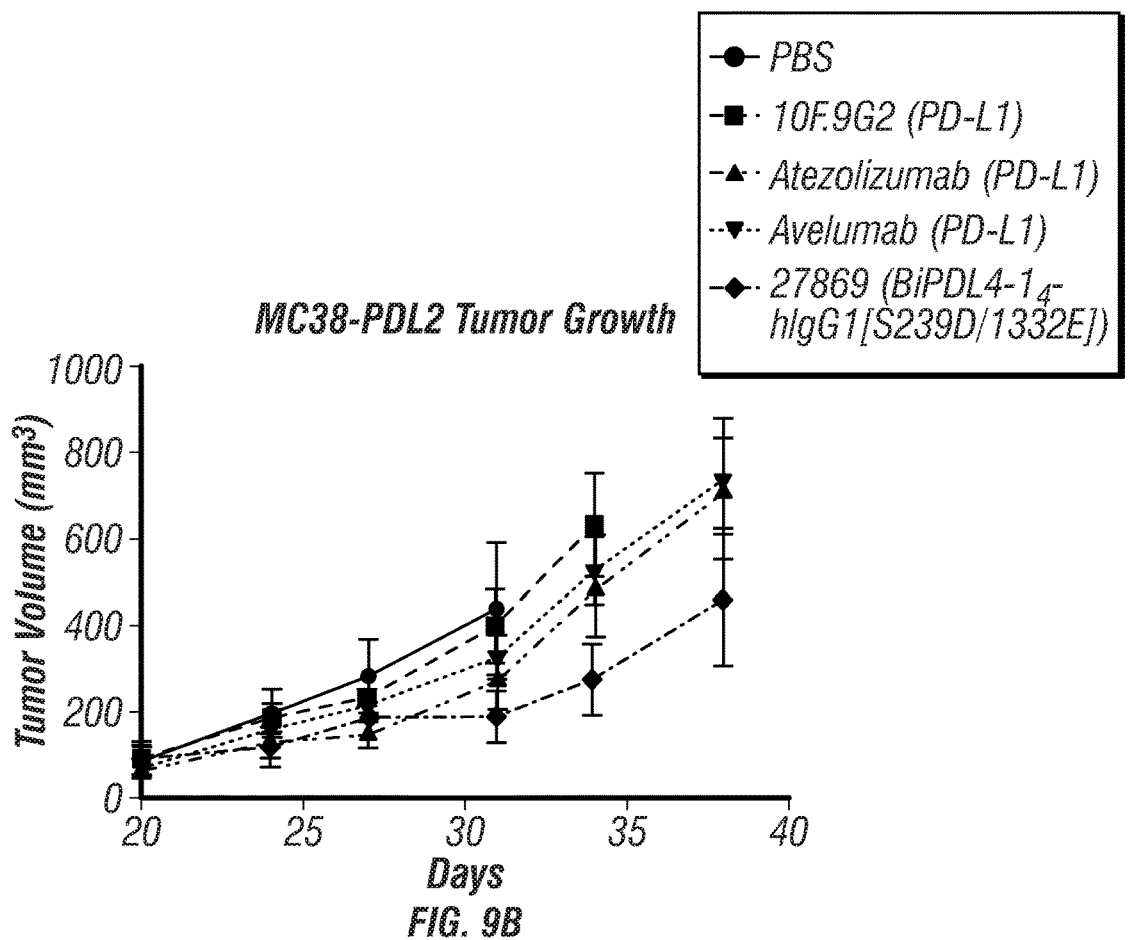
Figure 9C:
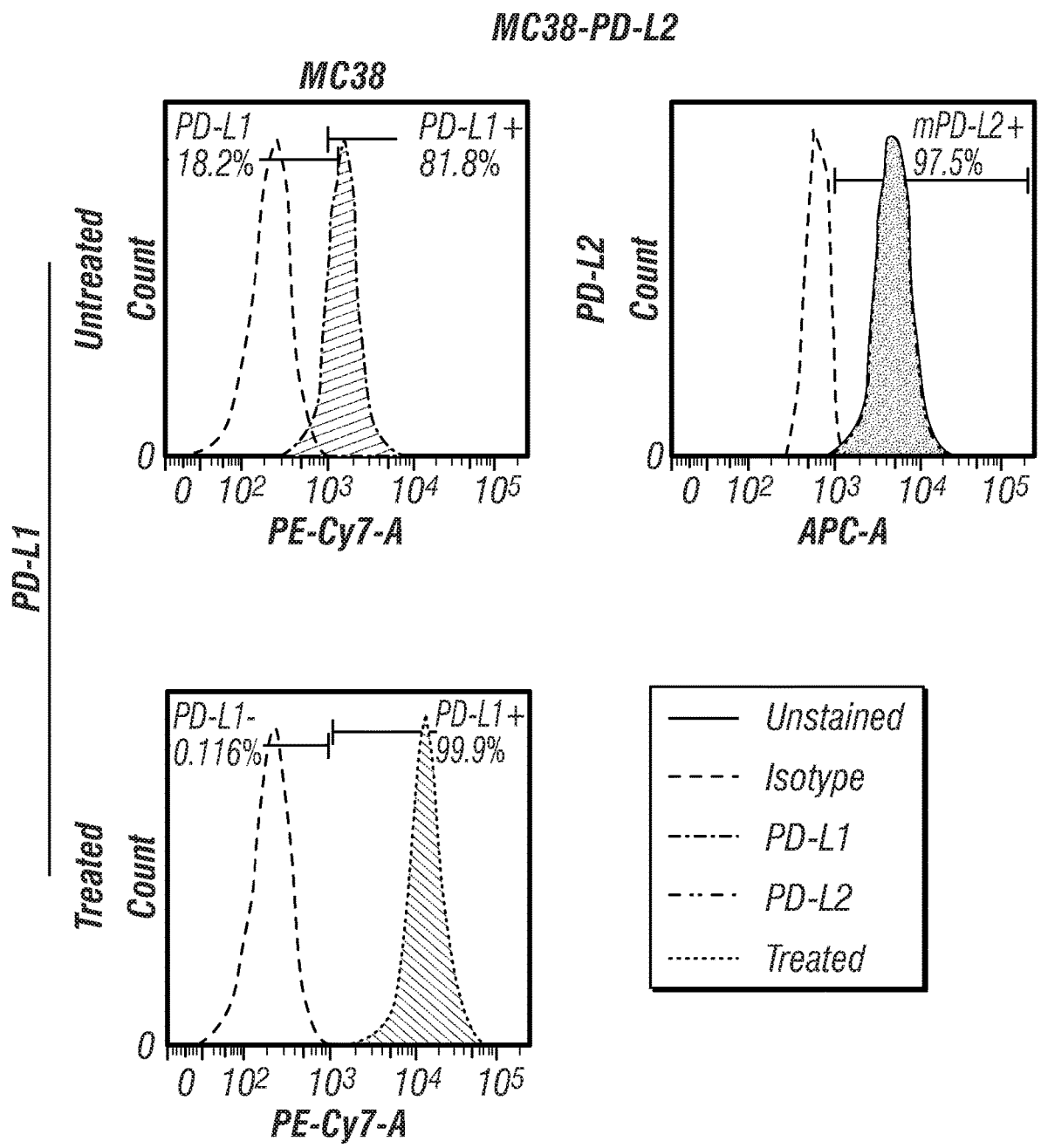

FIGS. 9A-9C—BiPDL antibodies treat syngeneic MC38-PD-L2 colon carcinoma more effectively than PD-L1 antibodies. 5×10$^5$ MC38-PDL2 tumor cells were implanted subcutaneously in C57BL/6J mice. Mice were treated with 100 μg of the indicated antibody on days 3, 6, 9, 12, and 15. (FIG. 9A) Survival is shown for a single experiment of 10 mice per group (p values via Gehran-Breslow-Wilcoxon test). (FIG. 9B) Growth of MC-38-PD-L2 tumors on the flank was measured with calipers and tumor volume is shown for all groups until such time as any tumor measured ≥1000 mm$^3$. (FIG. 9C) The presence of PD-L1 and PD-L2 was evaluated by flow cytometry.

Figure 10A:
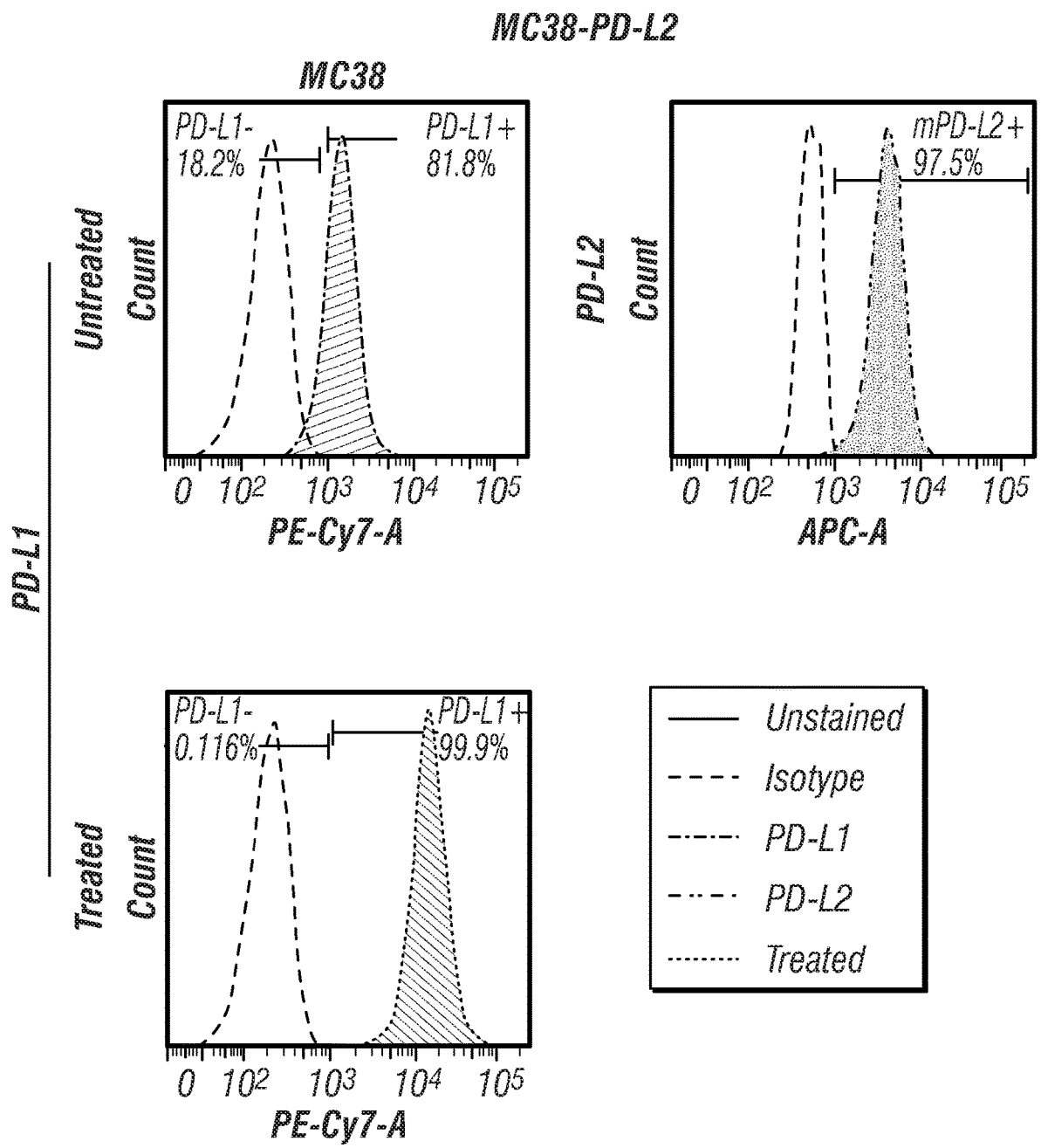
Figure 10B:
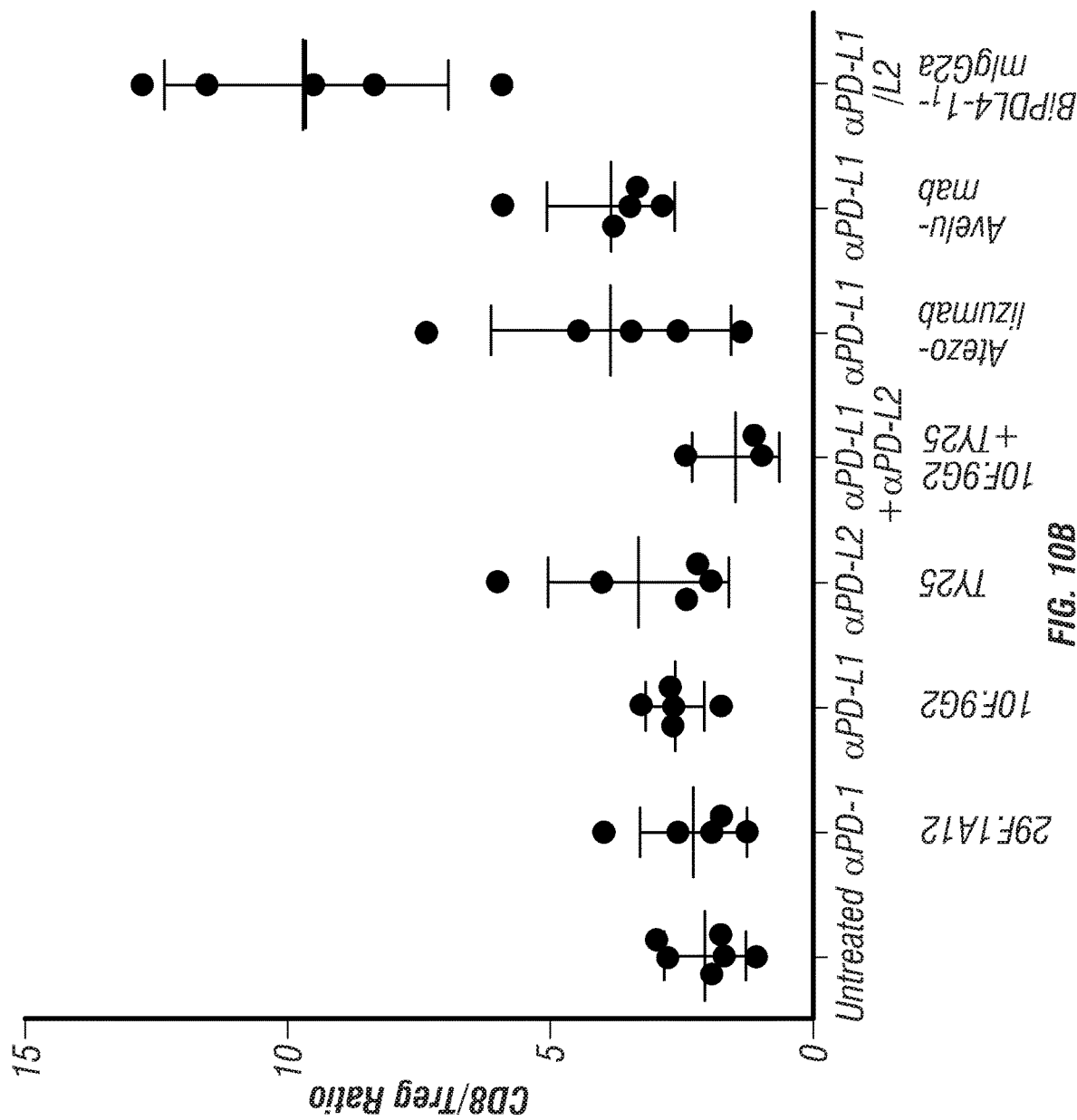

FIGS. 10A-10B—BiPDL antibodies with antibody-dependent cell-mediated cytotoxicity (ADCC) generate advantageous CD8 to Treg ratios in MC38-PD-L2 mice. 1.5×10$^6$ MC38-PDL2 tumor cells were implanted subcutaneously in C57BL/6J mice in 30% Matrigel (Corning) and treated with 100 μg of the indicated antibody on days 7, 10, and 13 injected intraperitoneally. On day 15, tumors were harvested. (FIG. 10A) The presence of PD-L1 and PD-L2 was evaluated by flow cytometry. (FIG. 10B) The ratios of infiltrating CD8 T cells relative to FoxP3+ Treg were measured by flow cytometry.

Figure 11A:
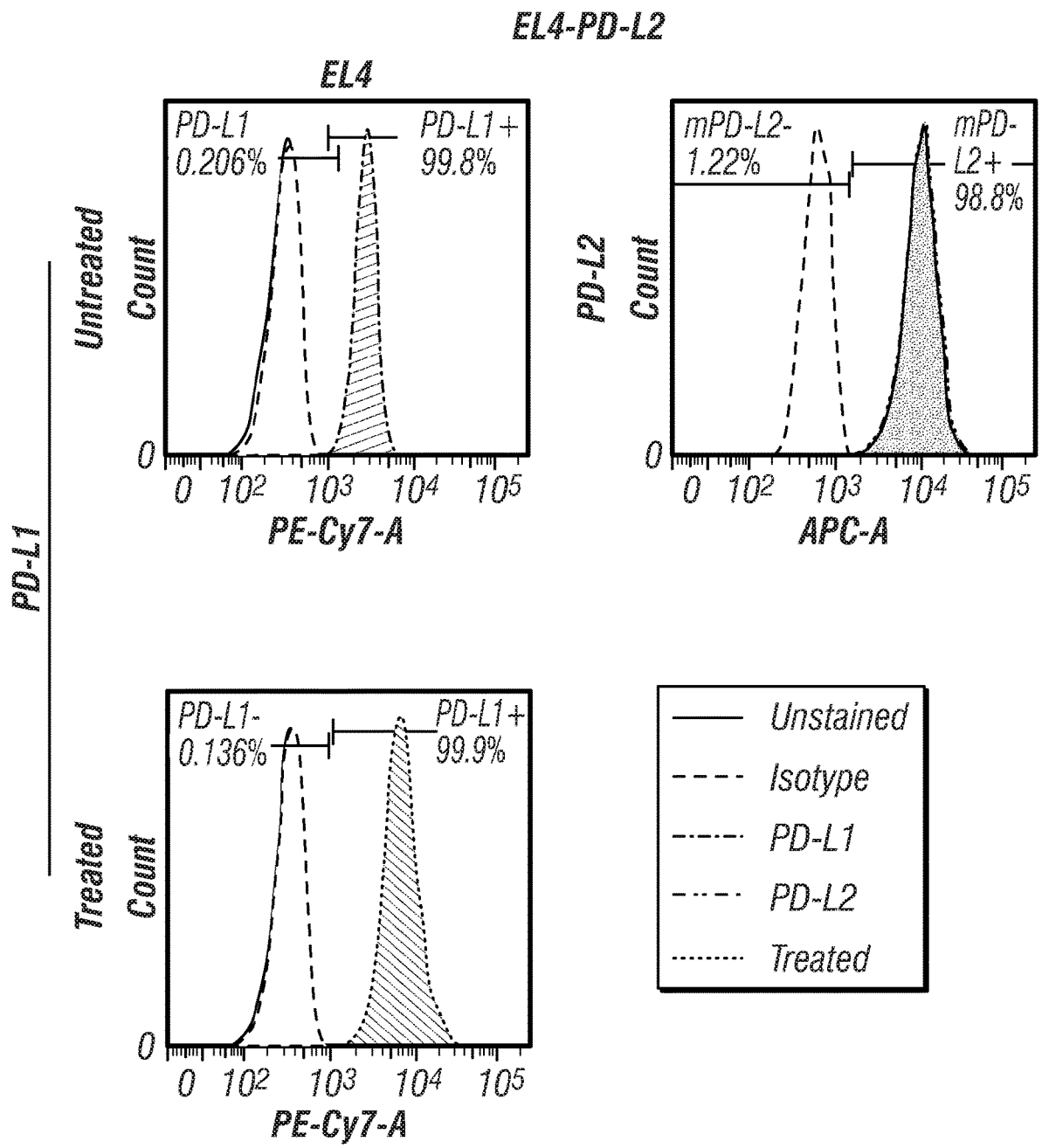
Figure 11B:
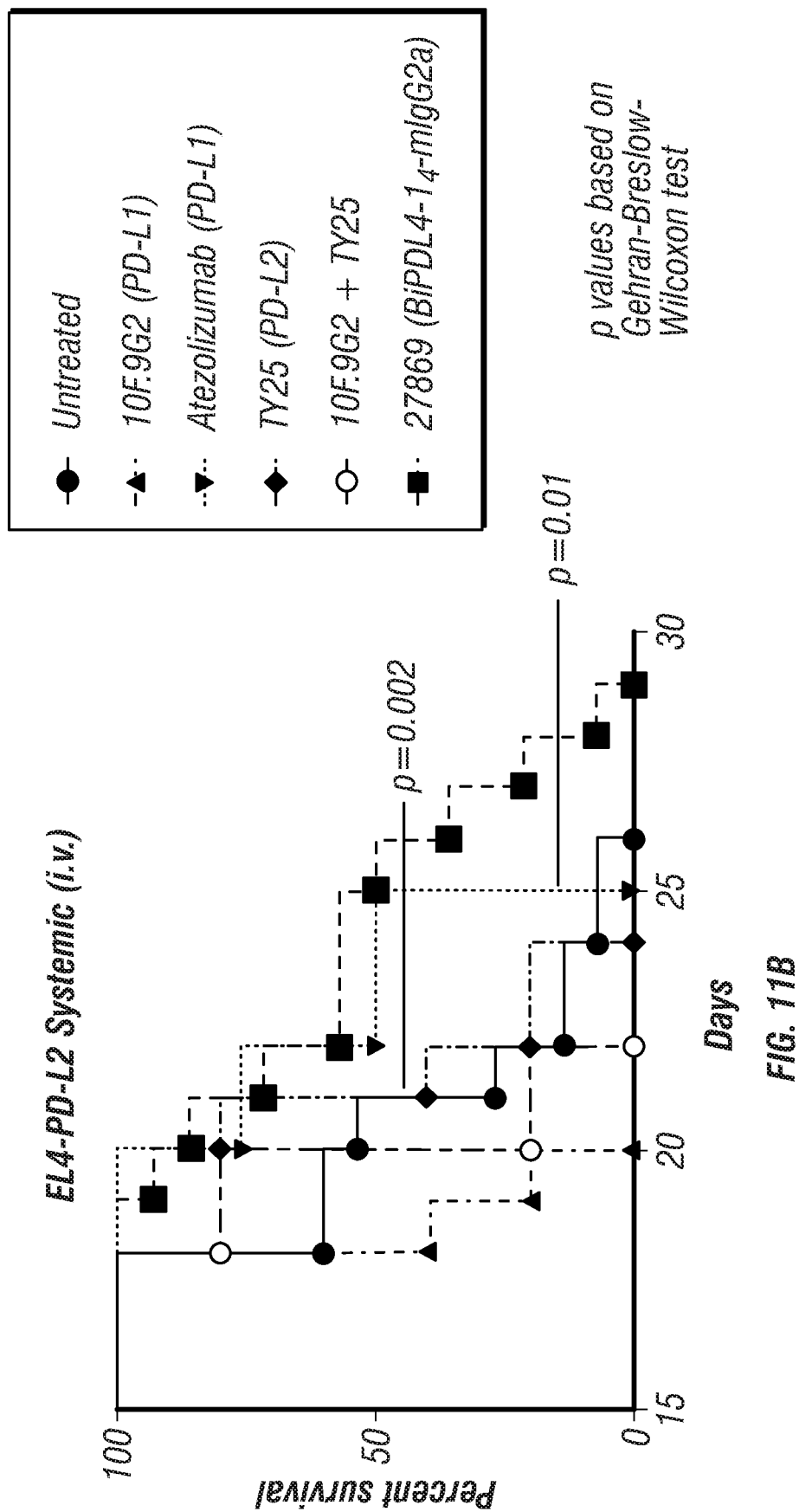

FIGS. 11A-11B—BiPDL antibodies treat systemic EL4 T cell lymphoma more effectively than PD-L1 or PD-L2 blockade. 1.5×10$^5$ EL4-PD-L2 cells, which also express Luciferase to facilitate bioluminescent imaging, were implanted to establish systemic disease in C57BL/6J mice. On days 3, 6, 9, 12 and 15 mice received 100 μg injections of the indicated antibody. (FIG. 11A) Flow cytometry was used to assess the presence of PD-L1 and PD-L2. (FIG. 11B) Survival is shown for 1-3 independent experiments (depending on the group) with 5 mice per group. Survival statistics were calculated using the Gehran-Breslow-Wilcoxon test.

Figure 12:
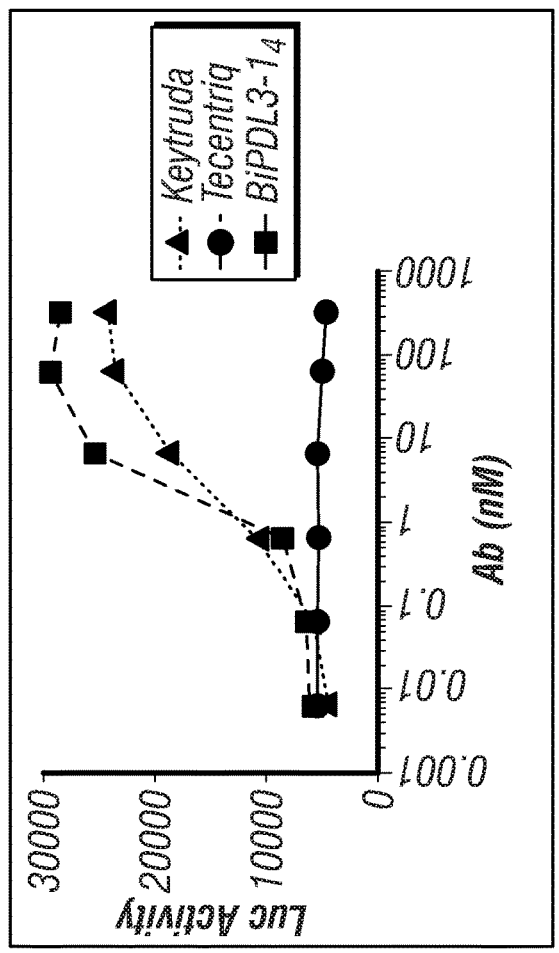

FIG. 12. Equivalence to PD-1 blockade and superiority to PD-L1 blockade in Promega® PD-L1/PD-L2 assay. BiPDL3-14 completely blocks PD-1 engagement. The Promega® PD-1 assay consisting of CHO cells expressing a T cell activation element and human PD-L1 and PD-L2 and Jurkat T cells with an NFAT-Luciferase reporter was used to test the capacity of Keytruda® (pembrolizumab), Tecentriq® (atezolizumab) and BiPDL to block PD-1-mediated T cell suppression.

Figure 13:
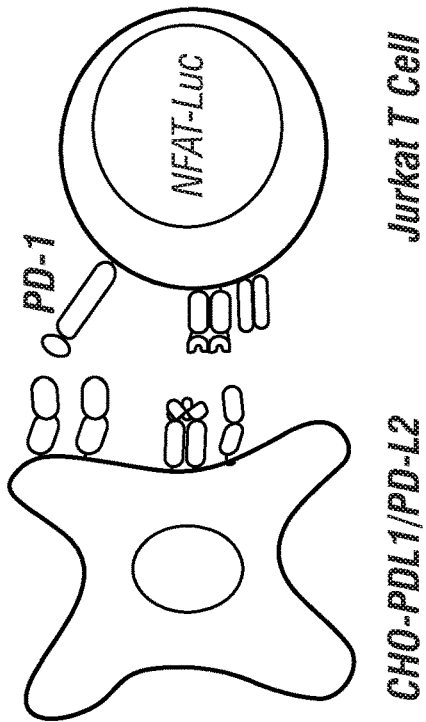
Figure 13:
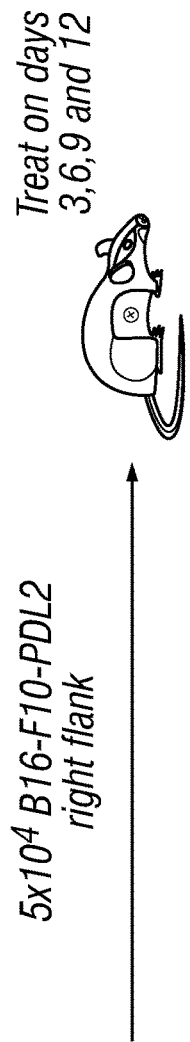
Figure 13:
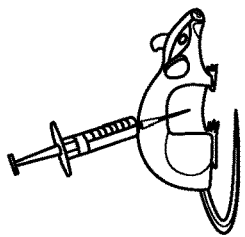
Figure 13:
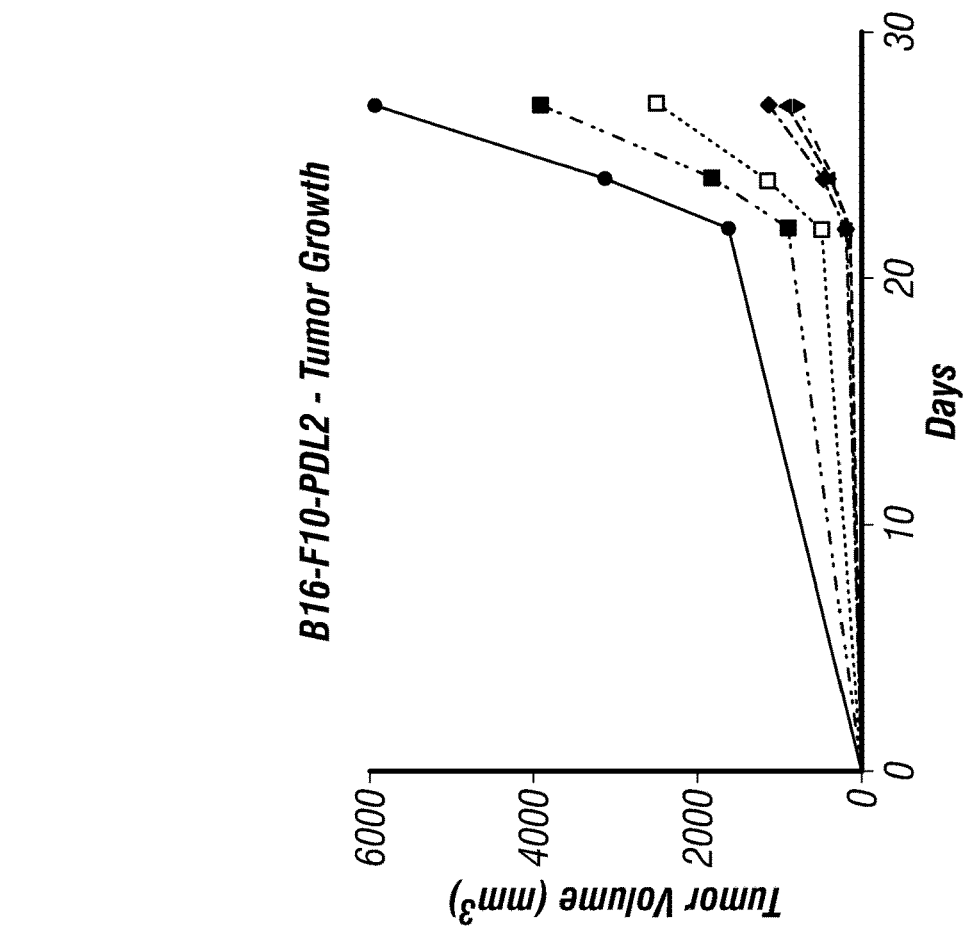
Figure 13:
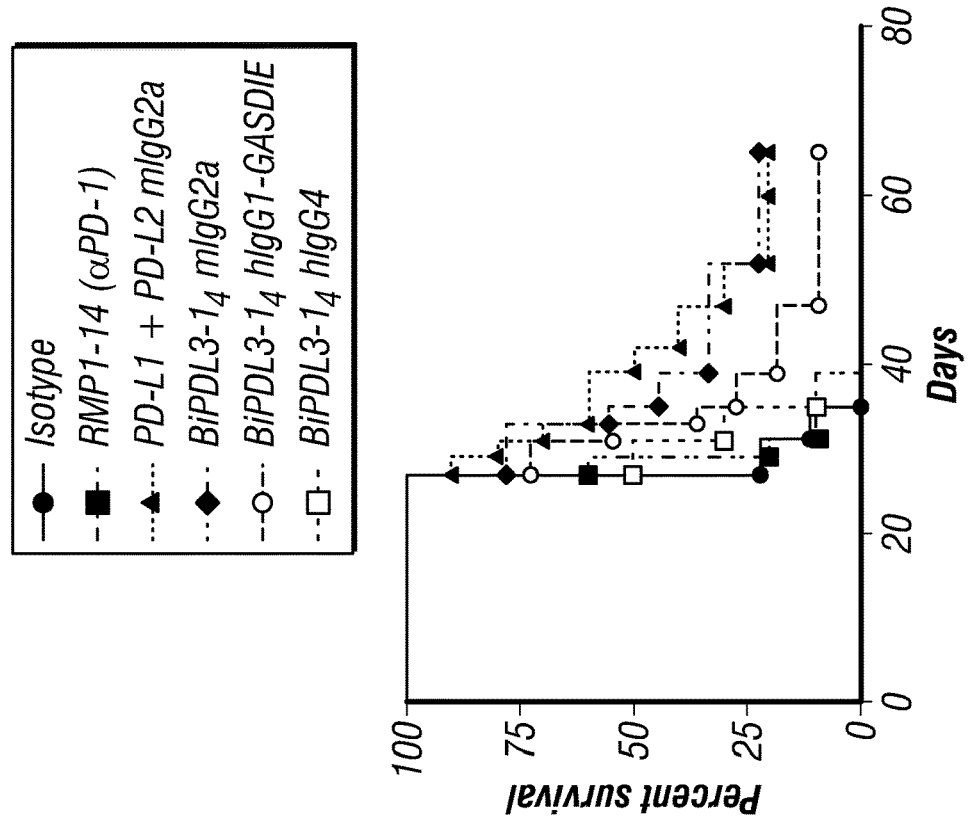

FIG. 13. F16-F10-PDL2 data suggests promise of effector BiPDL3 antibodies in "cold" tumors. BiPDL3 can cure PD-1 resistant B16 melanoma. Mice implanted with 5×10$^4$B16.F10 melanoma on the flank were treated on days 3, 6, 9, 12 with the indicated antibody i.p. GASDIE=hIgG1 with T236A, S239D, I332E mutations to enhance ADCC/P.

DESCRIPTION OF ILLUSTRATIVE EMBODIMENTS

The inventors have generated monoclonal antibodies with binding specificity for both human PD-L1 and PD-L2 proteins. As these antibodies have been demonstrated to bind to both PD-L1 and PD-L2, they present an opportunity to block the binding of either PD-L1 or PD-L2 to PD-1. They can also be used to deliver therapeutic payloads to PD-L1 or PD-L2 expressing cancer cells. These and other aspects of the disclosure are described in even greater detail below.

I. PD-L1

A. Structure

Programmed death-ligand 1 (PD-L1) is a protein encoded by the CD274 gene. PD-L1 is a 40 kDa type 1 transmembrane protein which may play a major role in immune suppression during a variety of events such as, pregnancy, tissue allografts, autoimmune disease, cancer and other disease states. The human PD-L1 protein is encoded by the amino acid sequence shown below:

```
                                            (SEQ ID NO: 1)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET
```

B. Function

PD-L1 is a ligand to its receptor, PD-1. PD-1 may be found on activated T cells, B cells, and myeloid cells. Binding of PD-L1 to PD-1 modulates T cell and B cell activation or inhibition, transmitting an inhibitor signal that reduces proliferation of antigen specific CD8+ T cells and CD4+ helper T-cells. Binding of PD-L1 to PD-1 also induces apoptosis. This reduction of CD8+ T cells and CD4+ helper T-cells has been thought to help PD-L1 expressing cancer cells evade anti-tumor immunity (Dong et al., 2002). Upregulation of PD-L1 has been associated with evasion of the host immune system, and is thought to be a cause of increased tumor aggressiveness (Thompson et al., 2004). The role of PD-L1 in evasion of anti-tumor immunity makes it an attractive target for therapeutic intervention.

II. PD-L2

A. Structure

Programmed death-ligand 2 (PD-L2) is a protein encoded by the CD273 gene. PD-L2 is a 31 kDa protein which may play a major role in immune suppression during a variety of events such as, pregnancy, tissue allografts, autoimmune disease, cancer and other disease states. The human PD-L2 protein is encoded by the amino acid sequence shown below:

```
                                            (SEQ ID NO: 2)
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPTWLLHIFIPFCIIAFIFIATVIALRKQLCQK

LYSSKDTTKRPVTTTKREVNSAI
```

PD-L2 is initially produced with a signal peptide corresponding to amino acids 1-19 of SEQ ID NO: 2, which is subsequently removed to yield the mature protein. The mature PD-L2 protein, corresponding to amino acids 20-273 of SEQ ID NO: 2, is comprised of an Ig-like V-domain, an Ig-like C2-type domain, transmembrane domain, and a cytoplasmic tail.

B. Function

PD-L2 is a ligand to its receptor, PD-1. PD-1 may be found on activated T cells, B cells, and myeloid cells. Binding of PD-L2 to PD-1 begins an immunological cascade which impairs proliferation, cytokine production, cytolytic function and survival of the T cell. PD-1 transmits an inhibitor signal that reduces proliferation of antigen specific CD8+ T cells and CD4+ helper T-cells. PD-L2 has also been shown to be an independent predictor of response to the PD-1 antibody pembrolizumab across multiple cancers (Yearley et al., 2017).

III. MONOCLONAL ANTIBODIES AND PRODUCTION THEREOF

A. General Methods

Antibodies to PD-L1 and PD-L2 may be produced by standard methods as are well known in the art (see, e.g., Antibodies: A Laboratory Manual, Cold Spring Harbor Laboratory, 1988; U.S. Pat. No. 4,196,265). The methods for generating monoclonal antibodies (mAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and tittering is repeated until a suitable titer is achieved. When a desired level of immunogenicity is obtained, the immunized animal can be bled and the serum isolated and stored, and/or the animal can be used to generate monoclonal antibodies.

Following immunization, somatic cells with the potential for producing antibodies, specifically B lymphocytes (B cells), are selected for use in the mAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this disclosure were generated using the SP2/0/mIL-6 cell line, an IL-6 secreting derivative of the SP2/0 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays and dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

Monoclonal antibodies produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Yeast-based antibody libraries may be designed rationally, and antibodies may be selected and/or isolated from such yeast-based antibody presentation libraries, as disclosed in, for example, WO2012/009568; WO2009/036379; WO2010/105256; WO2003/074679; U.S. Pat. Nos. 8,691,730; and 9,354,228. The antibodies may be expressed as full length IgGs from any desired cell type as disclosed in the above, and purified.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity, i.e., binding to PD-L1 and PD-L2. Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies may be generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibodies, and antibody libraries from which such antibodies may be selected and/or isolated, may be rationally designed and synthesized, such as by the Adimab® technology, as disclosed in, for example, WO2012/009568; WO2009/036379; WO2010/105256; WO2003/074679; U.S. Pat. Nos. 8,691,730; and 9,354,228. This method of synthesis antibodies requires that the nucleotide sequence coding for the desired or designed antibody be inserted into a vector for ectopic expression. Then the desired antibodies may be expressed as full chain IgG molecules and purified.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (–0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (–0.4), sulfur containing amino acids: cysteine (–1.0) and methionine (–1.3); hydrophobic, nonaromatic amino acids: valine (–1.5), leucine (–1.8), isoleucine (–1.8), proline (–0.5±1), alanine (–0.5), and glycine (0); hydrophobic, aromatic amino acids: tryptophan (–3.4), phenylalanine (–2.5), and tyrosine (–2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

IV. PHARMACEUTICAL FORMULATIONS AND TREATMENT OF CANCER

A. Cancers

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Cancer cells to which the methods of the present disclosure can be applied include generally any cell that expresses PD-L1 or PD-L2, and more particularly, that overexpresses either PD-L1 or PD-L2. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. Cancers may also be recurrent, metastatic and/or multi-drug resistant, and the methods of the present disclosure may be particularly applied to such cancers so as to render them resectable, to prolong or re-induce remission, to inhibit angiogenesis, to prevent or limit metastasis, and/or to treat multi-drug resistant cancers. At a cellular level, this may translate into killing cancer cells, inhibiting cancer cell growth, or otherwise reversing or reducing the malignant phenotype of tumor cells.

B. Formulation and Administration

The present disclosure provides pharmaceutical compositions comprising bispecific antibodies directed to PD-L1 and PD-L2 (BiPDL). In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Other suitable pharmaceutical excipients include starch, glucose, lactose, sucrose, saline, dextrose, gelatin, malt, rice, flour, chalk, silica gel, sodium stearate, glycerol monostearate, talc, sodium chloride, dried skim milk, glycerol, propylene glycol, water, ethanol and the like.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The antibodies of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

C. Combination Therapies

In the context of the present disclosure, it also is contemplated that bispecific antibodies to PD-L1 and PD-L2 (Bi-PDL) described herein could be used similarly in conjunction with chemo- or radiotherapeutic intervention, or other treatments. It also may prove effective, in particular, to combine bispecific PD-L1 and PD-L2 antibodies with other therapies that target different aspects of PD-L1 or PD-L2 function, such as peptides and small molecules that target the PD-L1 or PD-L2 cytoplasmic domain.

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with a bispecific anti-PD-L1 and anti-PD-L2 antibody according to the present disclosure and at least one other agent. These compositions would be provided in a combined amount effective to kill or inhibit proliferation of the cell. This process may involve contacting the cells with the bispecific anti-PD-L1 and anti-PD-L2 antibody according to the present disclosure and the other agent(s) or factor(s) at the same time. This may be achieved by contacting the cell with a single composition or pharmacological formulation that includes both agents, or by contacting the cell with two distinct compositions or formulations, at the same time, wherein one composition includes the bispecific anti-PD-L1 and anti-PD-L2 antibody according to the present disclosure and the other includes the other agent.

Alternatively, the bispecific anti-PD-L1 and anti-PD-L2 antibody therapy may precede or follow the other agent treatment by intervals ranging from minutes to weeks. In embodiments where the other agent and the bispecific anti-PD-L1 and anti-PD-L2 antibody are applied separately to the cell, one would generally ensure that a significant period of time did not expire between each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the bispecific anti-PD-L1 and anti-PD-L2 antibody or the other agent will be desired. Various combinations may be employed, where a bispecific anti-PD-L1 and anti-PD-L2 antibody according to the present disclosure therapy is "A" and the other therapy is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Administration of the therapeutic agents of the present invention to a patient will follow general protocols for the administration of that particular secondary therapy, taking into account the toxicity, if any, of the antibody treatment. It is expected that the treatment cycles would be repeated as necessary. It also is contemplated that various standard therapies, as well as surgical intervention, may be applied in combination with the described cancer therapies.

The skilled artisan is directed to "Remington's Pharmaceutical Sciences" 15th Edition, Chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5 fluorouracil, vincristine, vinblastine and methotrexate, Temozolomide (an aqueous form of DTIC), or any analog or derivative variant of the foregoing. The combination of chemotherapy with biological therapy is known as biochemotherapy. The present invention contemplates any chemotherapeutic agent that may be employed or known in the art for treating or preventing cancers.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic agent and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T-cells and NK cells. The combination of therapeutic modalities, i.e., direct cytotoxic activity and inhibition or reduction of Fortilin would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. Nos. 5,801,005; 5,739,169; Hui and Hashimoto, 1998; Christodoulides et al., 1998), cytokine therapy (e.g., interferons, and; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846, 945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin® (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with Herceptin® (trastuzumab) and chemotherapy has been shown to be more effective than the individual therapies. Thus, it is contemplated that one or more anti-cancer therapies may be employed with the tumor-associated HLA-restricted peptide therapies described herein.

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders was few compared to those who did not respond.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989). Possible therapeutic antibodies include anti-TNF, anti-CD25, anti-CD3, anti-CD20, CTLA-4-IG, and anti-CD28.

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

4. Gene Therapy

In yet another embodiment, the secondary treatment is a gene therapy in which a therapeutic polynucleotide is administered before, after, or at the same time as the tumor-associated HLA-restricted peptide is administered. Delivery of a vector encoding the tumor-associated HLA-restricted peptide in conjunction with a second vector encoding one of the following gene products will have a combined anti-hyperproliferative effect on target tissues. Alternatively, a single vector encoding both genes may be used. A variety of proteins are encompassed within the invention, some of which are described below. Various genes that may be targeted for gene therapy of some form in combination with the present invention are well known to one of ordinary skill in the art and may comprise any gene involved in cancers.

Inducers of Cellular Proliferation. The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity. The proteins Jun, Fos and Myc are proteins that directly exert their effects on nuclear functions as transcription factors.

Inhibitors of Cellular Proliferation. The tumor suppressor oncogenes function to inhibit excessive cellular proliferation. The inactivation of these genes destroys their inhibitory activity, resulting in unregulated proliferation. The most common tumor suppressors are Rb, p53, p21 and p16. Other genes that may be employed according to the present invention include APC, DCC, NF-1, NF-2, WT-1, MEN-I, MEN-II, zac1, p73, VHL, C-CAM, MMAC1/PTEN, DBCCR-1, FCC, rsk-3, p27, p27/p16 fusions, and p21/p27 fusions.

Regulators of Programmed Cell Death. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

V. ANTIBODY CONJUGATES

Antibodies may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., immunosuppression/anti-inflammation. Non-limiting examples of such molecules are set out above. Such molecules are optionally attached via cleavable linkers designed to allow the molecules to be released at or near the target site.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups are often used to bind radioisotopes to antibody and exist as metallic ions are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green® 488, Oregon Green® 500, Oregon Green® 514, Pacific Blue™, REG, Rhodamine Green, Rhodamine Red, Renographin, ROX, TAMRA, TET, Tetramethylrhodamine, and/or Texas Red®.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277, 437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VI. IMMUNODETECTION METHODS

In still further embodiments, there are immunodetection methods for binding, purifying, removing, quantifying and otherwise generally detecting PD-L1 or PD-L2 and their associated antigens. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of PD-L1 and PD-L2 antibodies also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to PD-L1 and PD-L2 present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple sense, are binding assays. Certain preferred immunoassays are the various types of enzyme linked immunosorbent assays (ELISAs) and radioimmunoassays (RIA) known in the art Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing PD-L1 and/or PD-L2 is added to the wells. After binding and washing to remove non-specifically bound immune complexes, the bound antigen may be detected. Detection may be achieved by the addition of another bispecific antibody directed to PD-L1 and PD-L2 linked to a detectable label, or by an anti-PD-L1 or anti-PD-L2 antibody that is linked to a detectable label. This type of ELISA is a simple "sandwich ELISA." Detection may also be achieved by the addition of a second bispecific antibody to PD-L1 and PD-2, or an anti-PD-L1 or anti-PD-L2 antibody, followed by the addition of a third antibody that has binding affinity for the second antibody, with the third antibody being linked to a detectable label.

In another exemplary ELISA, the samples suspected of containing the PD-L1 and/or PD-L2 antigen are immobilized onto the well surface and then contacted with a bispecific anti-PD-L1 and anti-PD-L2 antibody. After binding and washing to remove non-specifically bound immune complexes, the bound bispecific anti-PD-L1 and anti-PD-L2 antibodies are detected. Where the initial bispecific anti-PD-L1 and anti-PD-L2 antibodies are linked to a detectable label, the immune complexes may be detected directly. Again, the immune complexes may be detected using a second antibody that has binding affinity for the first bispecific anti-PD-L1 and anti-PD-L2 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG)

or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probing. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, there are immunodetection kits for use with the immunodetection methods described above. The immunodetection kits will thus comprise, in suitable container means, a first bispecific antibody that binds to PD-L1 and/or PD-L2 antigens, and optionally an immunodetection reagent.

In certain embodiments, the bispecific antibody to PD-L1 and PD-L2 may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the PD-L1 and PD-L2 antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Antibody selection, generation, and production. Although additional detail may be provided in subsequent Examples, the selection, generation, and production of the disclosed antibodies were performed generally as follows.

Antigen preparation-Antigens were biotinylated using the EZ-Link® Sulfo-NHS-Biotinylation Kit from Pierce. Goat F(ab')2 anti-human kappa-FITC (LC-FITC), ExtrAvidin-PE (EA-PE) and Streptavidin-AF633 (SA-633) were obtained from Southern Biotech, Sigma®, and Molecular Probes, respectively. Streptavidin MicroBeads and MACS LC separation columns were purchased from Miltenyi Biotec®. Goat anti-human IgG-PE (Human-PE) was obtained from Southern Biotech.

Naïve Discovery—Eight naïve human synthetic yeast libraries each of ~109 diversity were propagated as previously described (see, e.g., Xu et al., 2013; WO2009036379; WO2010105256; and WO2012009568.) For the first two rounds of selection, a magnetic bead sorting technique utilizing the Miltenyi® MACS system was performed, as previously described (see, e.g., Siegel et al., 2004.) Briefly, yeast cells (~1010 cells/library) were incubated with 3 ml of 10 nM biotinylated Fc fusion-antigen for 15 min at 30° C. in wash buffer (phosphate-buffered saline (PBS)/0.1% bovine serum albumin (BSA)). After washing once with 40 ml ice-cold wash buffer, the cell pellet was resuspended in 20 mL wash buffer, and Streptavidin MicroBeads (500 µl) were added to the yeast and incubated for 15 min at 4° C. Next, the yeast were pelleted, resuspended in 20 mL wash buffer, and loaded onto a Miltenyi® LS column. After the 20 mL were loaded, the column was washed 3 times with 3 ml wash buffer. The column was then removed from the magnetic field, and the yeast were eluted with 5 mL of growth media and then grown overnight. The following rounds of selection were performed using flow cytometry. Approximately 2×107 yeast were pelleted, washed three times with wash buffer, and incubated at 30° C. with either 10 nM Fc-fusion antigen or in later rounds decreasing concentrations of biotinylated antigen (100 to 1 nM) under equilibrium conditions, 100 nM biotinylated antigens of different species (mouse) in order to obtain species cross-reactivity, or with a poly-specificity depletion reagent (PSR) to remove non-specific antibodies from the selection. For the PSR depletion, the libraries were incubated with a 1:10 dilution of biotinylated PSR reagent as previously described (see, e.g., Xu et al., 2013). Yeast were then washed twice with wash buffer and stained with LC-FITC (diluted 1:100) and either SA-633 (diluted 1:500) or EAPE (diluted 1:50) secondary reagents for 15 min at 4° C. After washing twice with wash buffer, the cell pellets were resuspended in 0.3 mL wash buffer and transferred to strainer-capped sort tubes. Sorting was performed using a FACS ARIA sorter (BD® Biosciences) and sort gates were determined to select for antibodies with desired characteristics. Selection rounds were repeated until a population with all of the desired characteristics was obtained.

In order to generate cross-reactive antibodies, selections as described above using each target antigen, independently, were alternated from round-to-round to enrich for the dual specificity. After the final round of sorting, yeast were plated and individual colonies were picked for characterization.

Light chain batch shuffle (LCBS)—The primary discovery also included a light chain batch diversification protocol from heavy chain plasmids from the naïve selections: Heavy chain plasmids from a naïve round four selection output were extracted from the yeast and transformed into a light chain library with a diversity of $5 \times 10^6$. Selections were performed with one round of MACS and three rounds of FACS employing the same conditions as the naïve discovery.

Antibody Optimization—Optimization of antibodies was performed by introducing diversities into the heavy chain and light chain variable regions as described below. A combination of some of these approaches was used for each antibody.

CDRH1 and CDRH2 selection: The CDRH3 of a single antibody was recombined into a premade library with CDRH1 and CDRH2 variants of a diversity of $1 \times 10^8$ and selections were performed with one round of MACS and four rounds of FACS as described in the naïve discovery. In the FACS rounds the libraries were looked at for PSR binding, species cross-reactivity, antigen cross-reactivity and affinity pressure, and sorting was performed in order to obtain a population with the desired characteristics. For these selections affinity pressures were applied either by titrating down biotinylated monomeric antigen or by preincubating the biotinylated antigen with parental Fab for 30 minutes and then applying that precomplexed mixture to the yeast library for a length of time which would allow the selection to reach an equilibrium. The higher affinity antibodies were then able to be sorted.

VH Mut selection: The heavy chain variable region (VH) was mutagenized via error prone PCR. The library was then created by transforming this mutagenized VH and the heavy chain expression vector into yeast already containing the light chain plasmid of the parent. Selections were performed similar to previous cycles using FACS sorting for three rounds. In the FACS rounds the libraries were looked at for cross-reactivity and affinity pressure, and sorting was performed in order to obtain a population with the desired characteristics.

CDRL1, CDRL2 and CDRL3 selection: Oligos were ordered from IDT which comprised the CDRL3 and were variegated via NNK diversity. The CDRL3 oligos were double-stranded using primers which annealed to the flanking region of the CDRL3. These double-stranded CDRL3 oligos were then recombined into a premade library with CDRL1 and CDRL2 variants of a diversity of $3 \times 10^5$ and selections were performed with one round of MACS and three rounds of FACS as described in the naïve discovery. In the FACS rounds the libraries were looked at for PSR binding, cross-reactivity, and affinity pressure, and sorting was performed in order to obtain a population with the desired characteristics. Affinity pressures for these selections were performed as described above in the CDRH1 and CDRH2 selection and alternating antigens from round to round was applied to enrich for dual binders.

Antibody production and purification—Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare™ LifeSciences).

ForteBio KD measurements—ForteBio affinity measurements were performed on an Octet® RED384 generally as previously described (see, e.g., Estep et al., 2013). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. For monovalent affinity assessment Fabs were used instead of IgGs. For this assessment the unbiotinylated Fc fusion antigen was loaded on-line onto the AHQ sensors. Sensors were equilibrated off-line in assay buffer for 30 min and then monitored on-line for 60 seconds for baseline establishment. Sensors with loaded antigen were exposed to 100 nM Fab for 3 minutes, and afterwards they were transferred to assay buffer for 3 min for off-rate measurement. All kinetics were analyzed using the 1:1 binding model.

ForteBio Epitope Binning/Ligand Blocking—Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Additional binding by the second antibody or ligand after antigen association indicates an unoccupied epitope (non-competitor), while no binding indicates epitope blocking (competitor or ligand blocking).

MSD®-SET KD measurements—Equilibrium affinity measurements of selected high affinity antibodies were performed generally as previously described (Estep et al., 2013). Briefly, solution equilibrium titrations (SET) were performed in PBS+0.1% IgG-Free BSA (PBSF) with antigen held constant at 50 pM and incubated with 3- to 5-fold serial dilutions of Fab starting at 20 nM. Antibodies (20 nM in PBS) were coated onto standard bind MSD®-ECL plates overnight at 4° C. or at room temperature for 30 min. Plates were then blocked by BSA for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD® Sector Imager 2400 instrument using 1× Read Buffer T with surfactant. The percent free antigen was plotted as a function of titrated antibody in Prism and fit to a quadratic equation to extract the KD. To improve throughput, liquid handling robots were used throughout MSD®-SET experiments, including SET sample preparation.

Cell Binding Analysis—Approximately 100,000 cells overexpressing the antigen were washed with wash buffer and incubated with 100 µl 100 nM IgG for 5 minutes at room temperature. Cells were then washed twice with wash buffer and incubated with 100 ul of 1:100 Human-PE for 15 minutes on ice. Cells were then washed twice with wash buffer and analyzed on a FACSCanto® II analyzer (BD® Biosciences).

Antibody Screening and Characterization. Antibody candidates generated from the presentation methods described above were tested for the capacity to bind to PD-L1 and PD-L2, and block their binding to PD-1. 5 µg/mL of antibody was bound to CHO-PD-L1 or CHO-PD-L2 cells and then recombinant PD-1 (R&D Systems) labelled with Alexa 532 (Thermo Fisher®) was added for 1 hour. PD-1 maximum fluorescence intensity was measured. Blockade of PD-1 binding was measured by reduction in Alexa 532 fluorescence by flow cytometry. To generate affinity KD to human PD-L1 or PD-L2, BiPDL Abs were loaded onto Anti-Human Fc Capture (AHC) Biosensors at 100 nM (15 µg/mL), and human PD-L1 or -L2 protein association and dissociation was tested in dilution series from 30-0.37 nM. The binding and release of the analyte are recorded by the Octet® instrument in real time and then used to calculate the Kd, Kon, and Kdis; results are derived from 2:1 Global Fit Modeling with reference well subtraction. To generate affinity KD to murine PD-L1 or PD-L2, BiPDL Abs were covalently immobilized onto activated Amine Reactive 2nd Generation (AR2G) Biosensors (quenched with 1M ethanolamine pH 8.5 after protein loading) at 100 nM (15 µg/mL), and mouse PD-L1 and PD-L2 protein association and dissociation was tested in dilution series from 300-1 nM. The binding and release of the analyte are recorded by the Octet® instrument in real time and then used to calculate the Kd, Kon, and Kdis; results are derived from 2:1 Global Fit Modeling with reference well subtraction.

Antibody Activity. Varying concentrations of BiPDL antibodies, with human IgG1 backbones, were added to CHO cells expressing either human or murine PD-L1 or PD-L2 (CHO-PD-L1 or CHO-PD-L2 cells). Binding was detected by addition of anti-human IgG1 secondary antibody conjugated to phycoerythrin (PE). FACS analysis was performed, detecting phycoerythrin to determine fluorescence activity at a variety of antibody concentrations. EC50 was calculated using GraphPad Prism® software.

Candidate antibodies prevent PD-1/PD-L2 binding. Candidate BiPDL antibodies and FDA approved antibodies were assayed using The Promega® PD-L1/PD-L2 Dual expression:PD-1 blockade system. Varying concentrations of antibody were added to CHO-PD-L1/L2 cells. PD-1 effector cells are Jurkat T cells which can be stimulated by CHO-PD-L1/L2 cells. The PD-1 effector cells, which produce firefly Luciferase in response to activation, were incubated with antibody and CHO cells for 6 hours and then the results were read out on a luminometer using the Bio-Glo™ (Fluorescein) assay kit (Promega®) according to the manufacturer's instructions. For competition assays, Biotin-rhPD-1-Fc protein was added to the cells and antibodies, followed by addition of Streptavidin-APC conjugate. Blocking was assessed as an increase in luciferase signal. Analysis was conducted using GraphPad Prism® software. For the competition assay, X was transformed to Log X and analyzed by non-linear regression (curve fit), dose response inhibition, and Log (inhibitor) vs. response.

BiPDL activity in mixed lymphocyte reactions. CD14+ monocytes were isolated from peripheral blood mononuclear cells using CD14 microbeads. Cells were seeded at 1 million/ml in and stimulated with IL-4 and GM-CSF in 10% FCS/RPMI/P/S cell culture medium. Cells were cultured for 7 days to differentiate into immature dendritic cells (IDCs) and varying concentrations of BiPDL or commercial antibodies were added. IDCs were then used to stimulate CD4+ T cells at a ratio of 10:1 CD4:IDCs. IL-2 and IFN-γ were assayed by ELISA following the protocols provided by R&D systems.

Antibody activity against xenograft tumors. U2940 PMBL or MDA-MB-231 triple-negative breast cancer xenograft tumors were established in immunodeficient mice. Tumors were allowed to reach a volume of 150 mm$^3$. After reaching 150 mm$^3$, the mice were treated with the antibody therapeutics shown twice per week, at a treatment of 10 mg/kg for 3 weeks with 9 mice per treatment group. Caliper measurements of tumor width, length, and depth were used to calculate tumor volume.

Survival and tumor growth of MC38-PD-L2 injected mice. Survival was measured for C57BL/6J mice implanted with MC38-PD-L2 tumor cells. $5 \times 10^5$ MC38-PD-L2 tumor cells were implanted subcutaneously and treated with 100 µg intraperitoneally of the indicated antibodies or buffer on days 3, 6, 9, 12, and 15. Caliper measurements of tumor with, length, and depth were used to calculate tumor volume. Survival statistics were calculated using the Gehran-Breslow-Wilcoxon test. To determine CD8/Treg ratios, $1.5 \times 10^6$ MC38-PDL2 tumor cells were implanted subcutaneously in C57BL/6J mice in 30% Matrigel (Corning) and treated with 100 µg injected intraperitoneally of the indicated antibody on days 7, 10, and 13. On day 15, tumors were harvested and ratios of infiltrating CD8 T cells relative to FoxP3$^+$ Treg were measured by flow cytometry.

Survival of EL4 Lymphoma Mouse Model. EL4 T cell lymphoma cells endogenously express PD-L1, and were retrovirally engineered to express mouse PD-L2. Expression of both PD-L1 and PD-L2 was verified by flow cytometry. Survival was measured for mice injected with EL4 cells expressing PD-L2 and luciferase. $1.5 \times 10^5$ EL4-PD-L2 cells which also express luciferase were injected into the mouse tail vein to establish systemic disease in C57BL/6J mice. Mice were treated with 100 µg intraperitoneally of the indicated antibodies on days 3, 6, 9, 12, and 15.

Epitope binning of BiPDL antibodies. Binding specificity of a variety of BiPDL antibodies were compared using a binding competition assay conducted using the ForteBio Octet® platform. Target His-tagged protein (human PD-L1 or PD-L2) is loaded onto pre-charged Nickel NTA Biosensors at 1 µg/mL. The first antibody, Ab1, is saturated on the target-loaded biosensor at 100 nM, and a reference (buffer only) well is included to determine maximal Ab2 binding signal. The second antibody is screened for binding signal also at 100 nM, and Ab1 is included to determine background self-blocking signal. Data Analysis HT 9.0 software is used to generate a matrix of raw signal response of Ab2 binding that is then transformed to be expressed as a percentage of the unblocked Ab2 binding signal. Less than 15% response is considered competitive blocking.

Example 2—Results

Figure 1A:
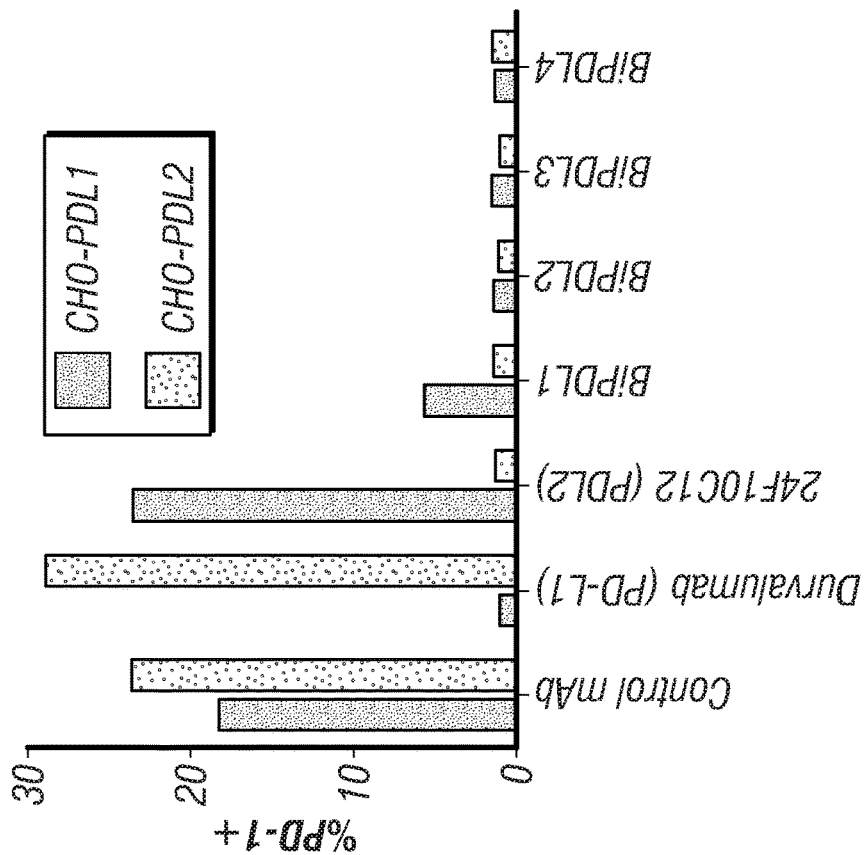
Figure 1C:
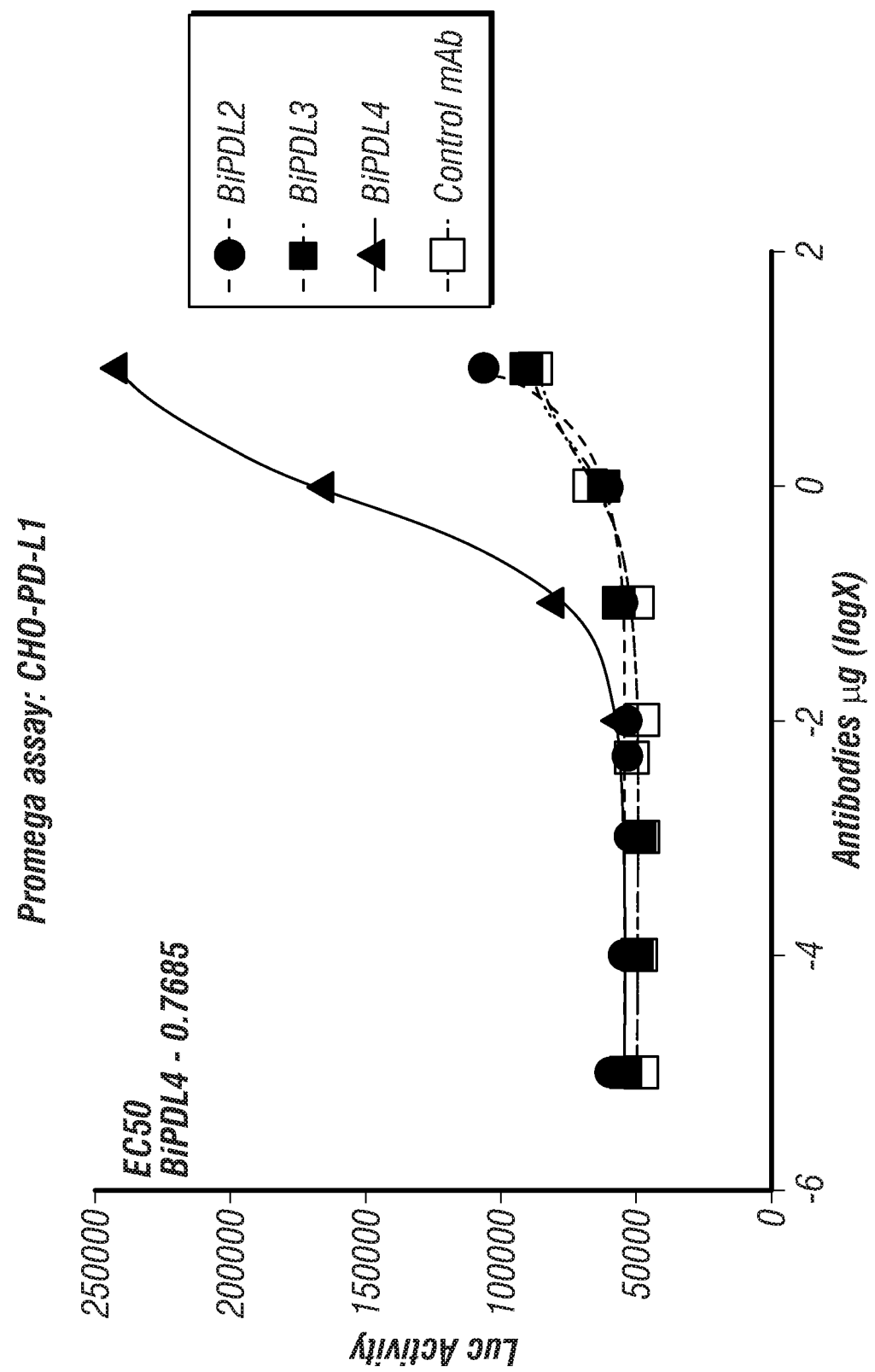

Selection of BiPDL antibodies which bind to both human PD-L1 and PD-L2. Given that both PD-L1 and PD-L2 bind to PD-1 and share approximately 40% amino acid identity, it was hypothesized that antibodies could be derived which bound both ligands and prevented their engagement of the T cell co-inhibitory receptor PD-1. As it was expected that finding high affinity antibodies capable of bivalent binding to both ligands to be rare, these antibodies were discovered through a process of iterative selection from the yeast-based, fully human antibody library presentation system as described above. Antibodies were first selected which bound to both PD-L1 and PD-L2 as described in Example 1 above, using recombinant ligands fused to human IgG1 Fc constant regions which dimerized (i.e., avid binding), and then the highest affinity hits were further enriched through selection of those capable of binding the monomeric PD-Ligands. This initial round of screening yielded four distinct lineages of antibodies capable of binding both PD-L1 and PD-L2 and blocking their binding to PD-1 (FIGS. 1A-B). Antibodies were termed BiPDL and use the nomenclature BiPDLX-YZ where X is the BiPDL family (Boussiotis, 2016; Cheng et al., 2013; Latchman et al., 2001; Lee et al., 2016), Y is the clone number within that family within a given generation, and Z is the generation representing successive rounds of affinity maturation (Boussiotis, 2016; Cheng et al., 2013; Latchman et al., 2001; Lee et al., 2016). Individual antibody clones are also referenced by the experimental clone number. Table 5 provides both the BiPDL nomenclature as well as the clone number for each. While each of these antibodies demonstrated reasonably high avidity (using dimeric ligands) for PD-L2 (Kd≤2×10-9), only BiPDL4 had a quantifiable avidity (Kd≤1×10-9) for human PD-L1 as measured by Octet® (ForteBio). Several antibodies were tested further for their capacity to relieve Jurkat T cell inhibition by PD-1 using the Promega® PD-1 assay system across a range of antibody concentrations and found that only BiPDL4 could block PD-L1-induced T cell suppression (FIG. 1C).

Figure 2A:
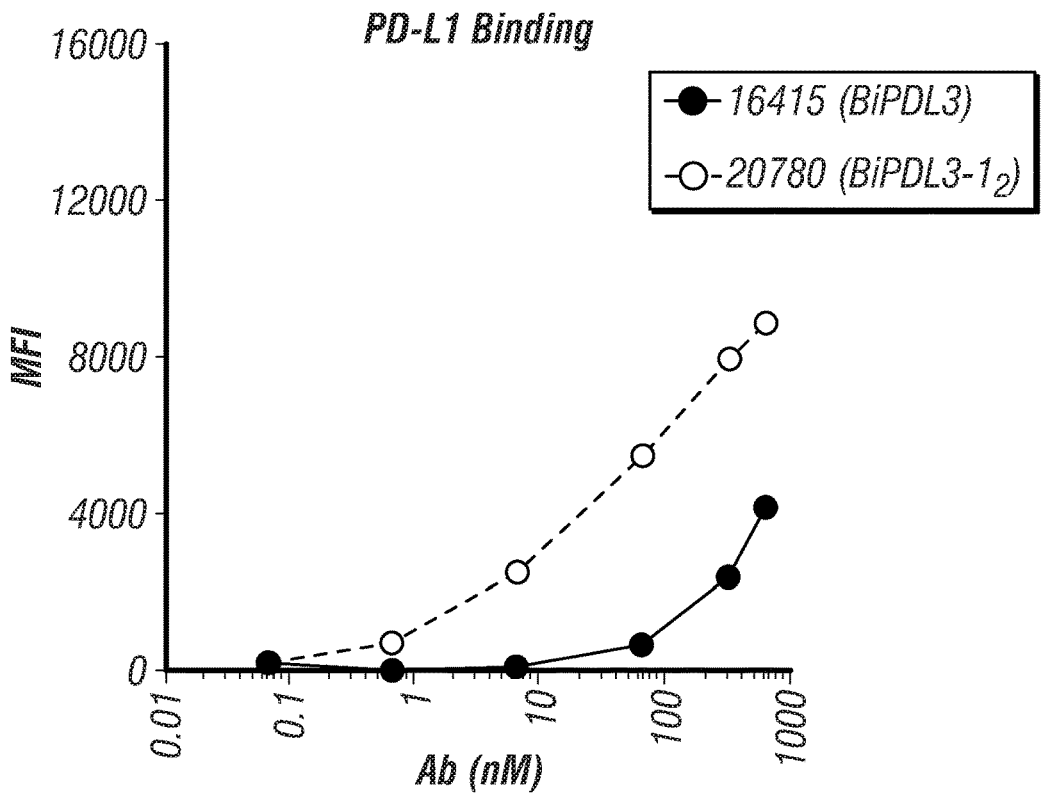
Figure 2B:
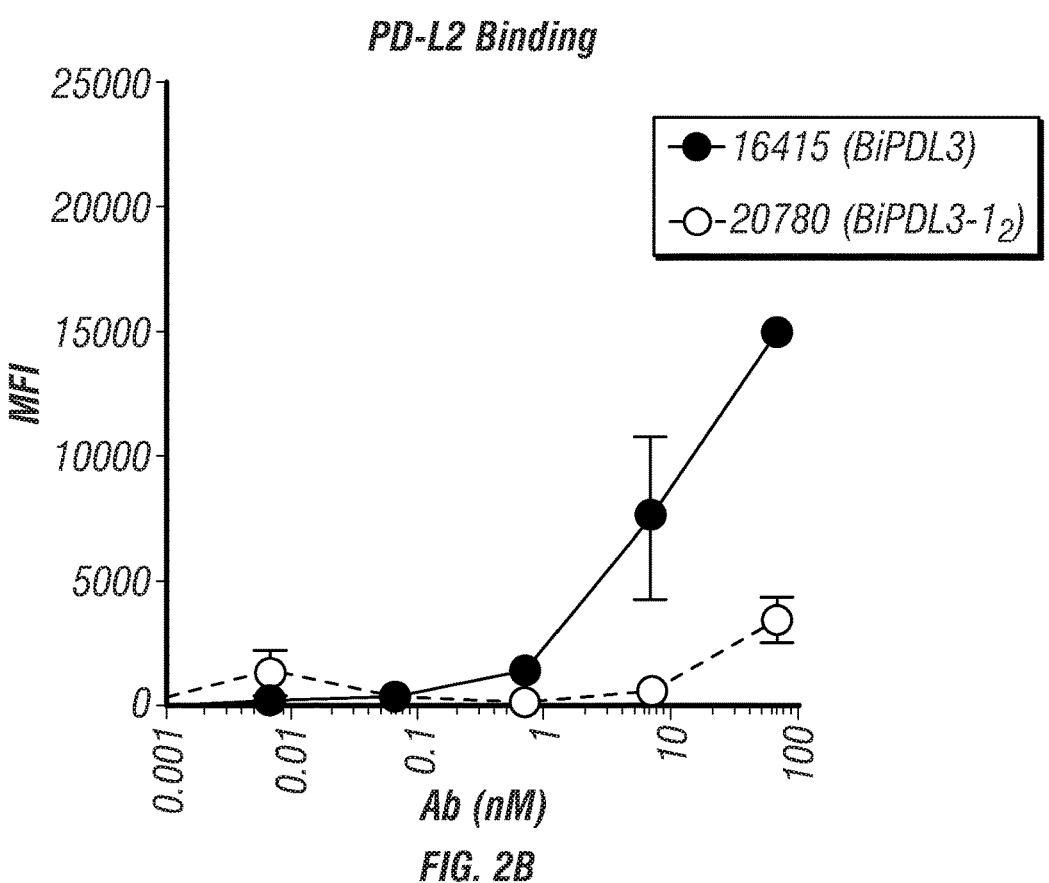

Affinity maturation increases the functional capacity of BiPDL to reverse PD-L1 and PD-L2 inhibition of T cell activation. Each of the first generation leads, BiPDL1-1$_1$, BiPDL2-1$_1$, BiPDL3-1$_1$, and BiPDL4-1$_1$ was subjected to heavy chain affinity maturation to enrich for clones binding to both PD-L1 and PD-L2 via selection of optimized CDR1 and CDR2 sequences using the processes described in Example 1 above. Varying concentrations of BiPDL3 and BiPDL4 antibodies (human IgG1) were added to CHO-PD-L1 or CHO-PD-L2 cells. Binding of affinity matured BiPDL3 and BiPDL4 was detected by addition of anti-human IgG1 secondary antibody conjugated to PE. (FIGS. 2A-D). All of the BiPDL3 and BiPDL4 antibodies retained their ability to bind PD-L1 (FIGS. 2A and 2C), though BiPDL3-1$_2$ showed little PD-L2 binding activity (FIG. 2B).

Figure 3:
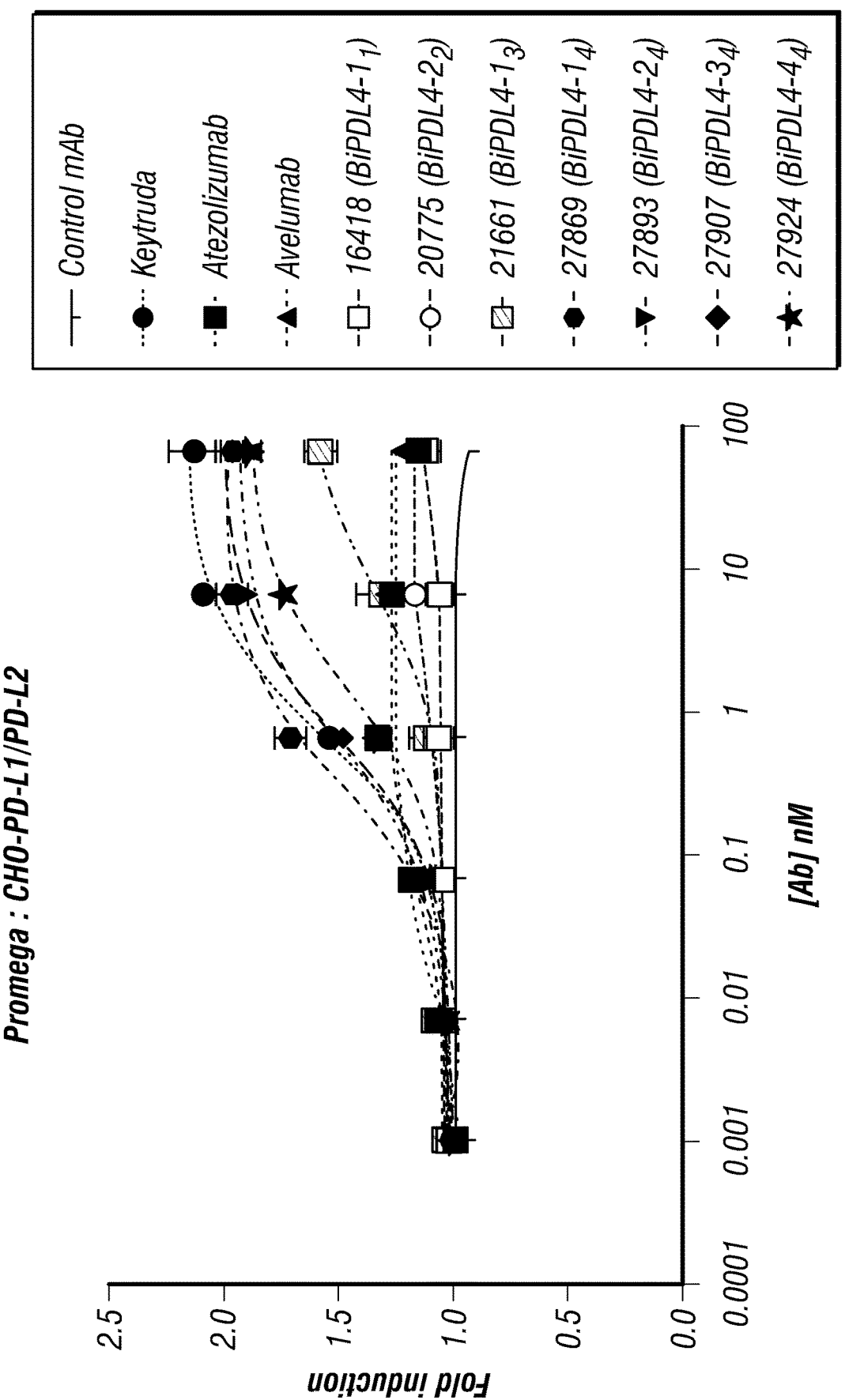
Figure 4A:
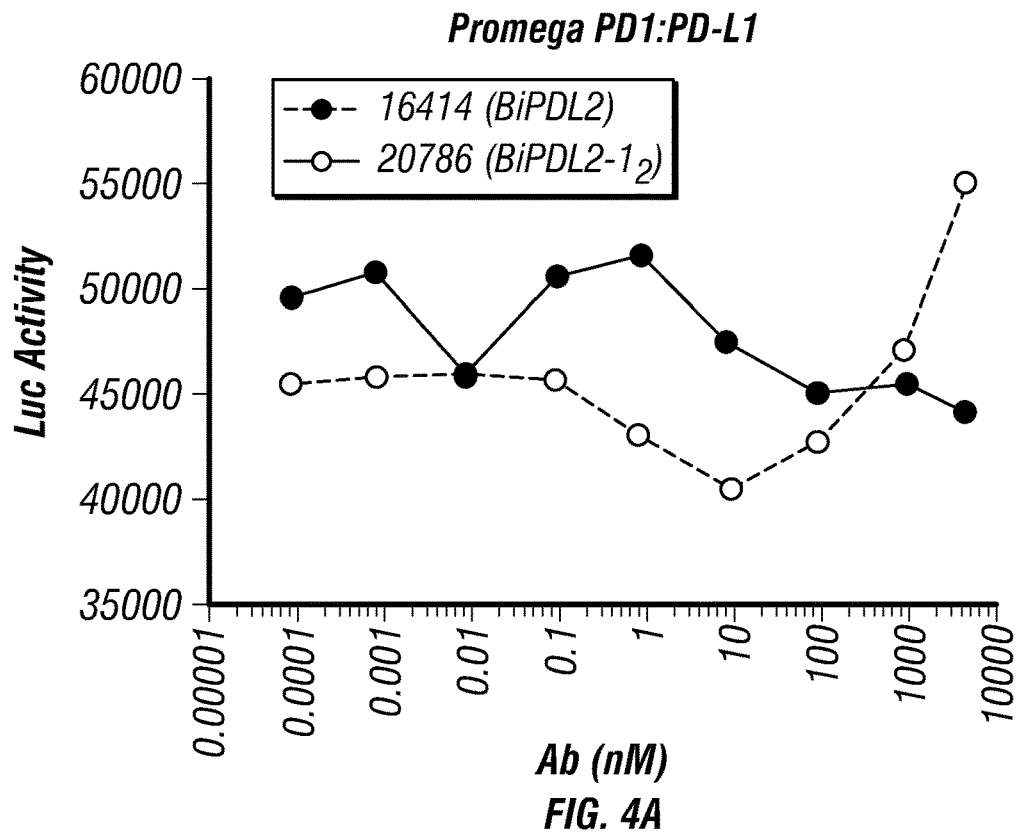
Figure 4B:
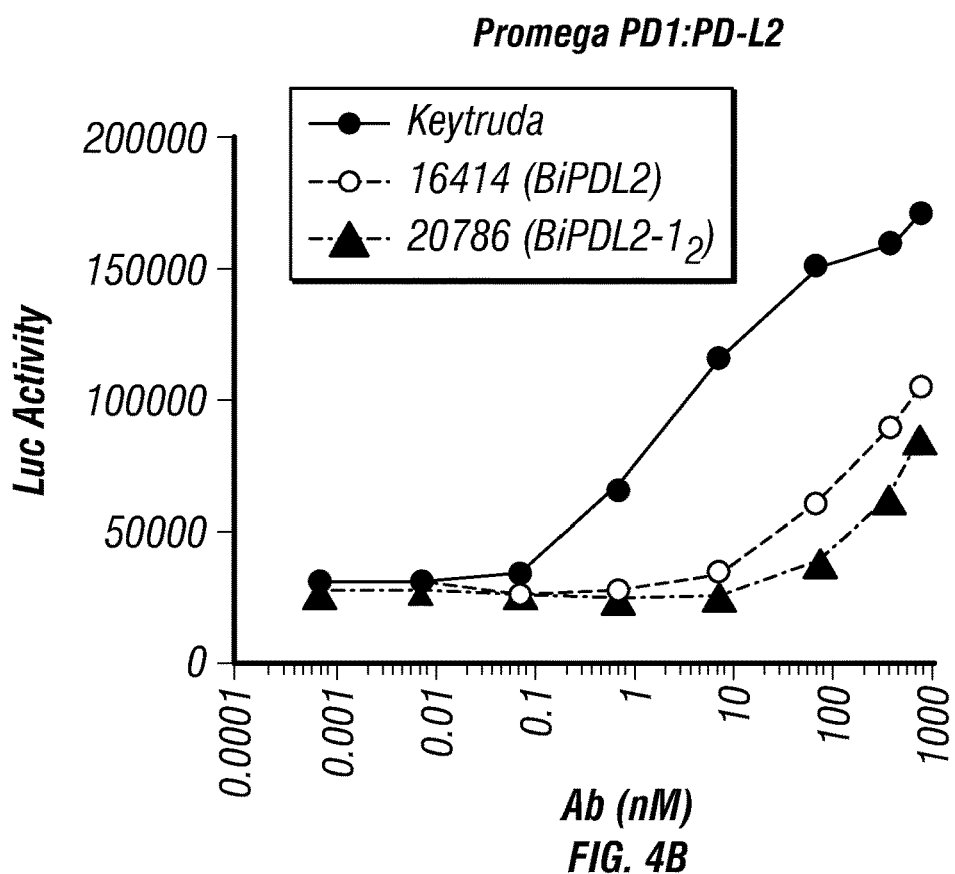
Figure 4C:
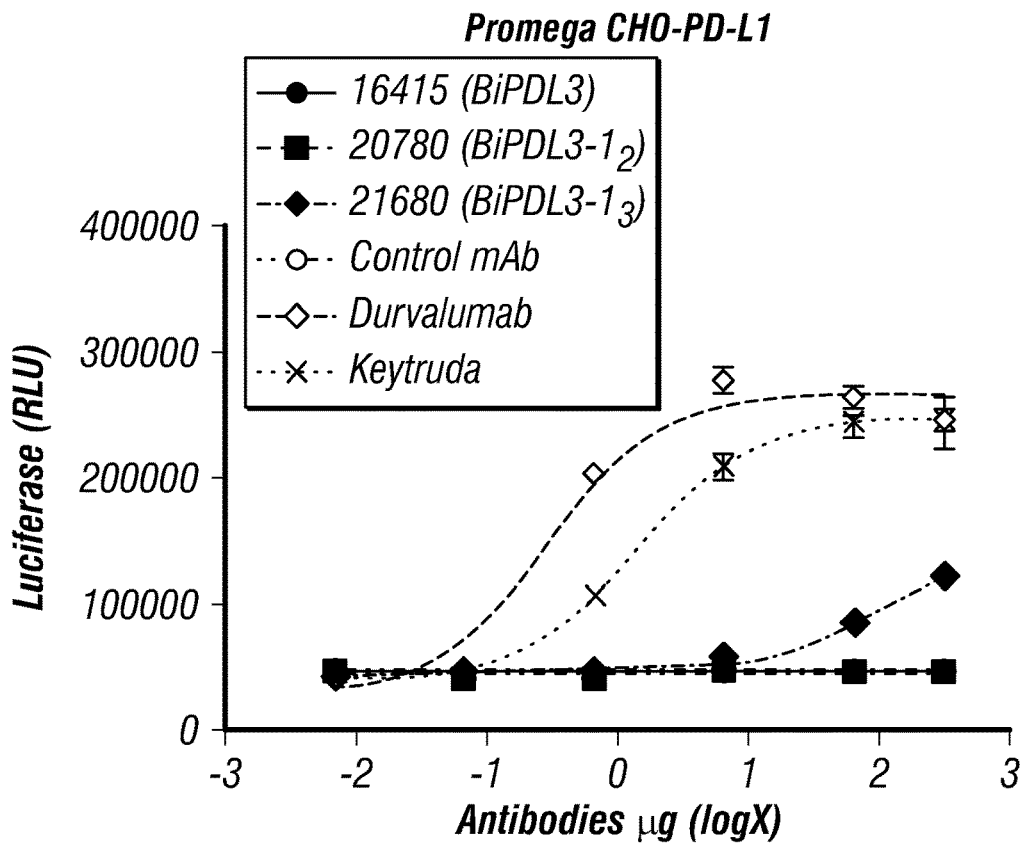
Figure 4D:
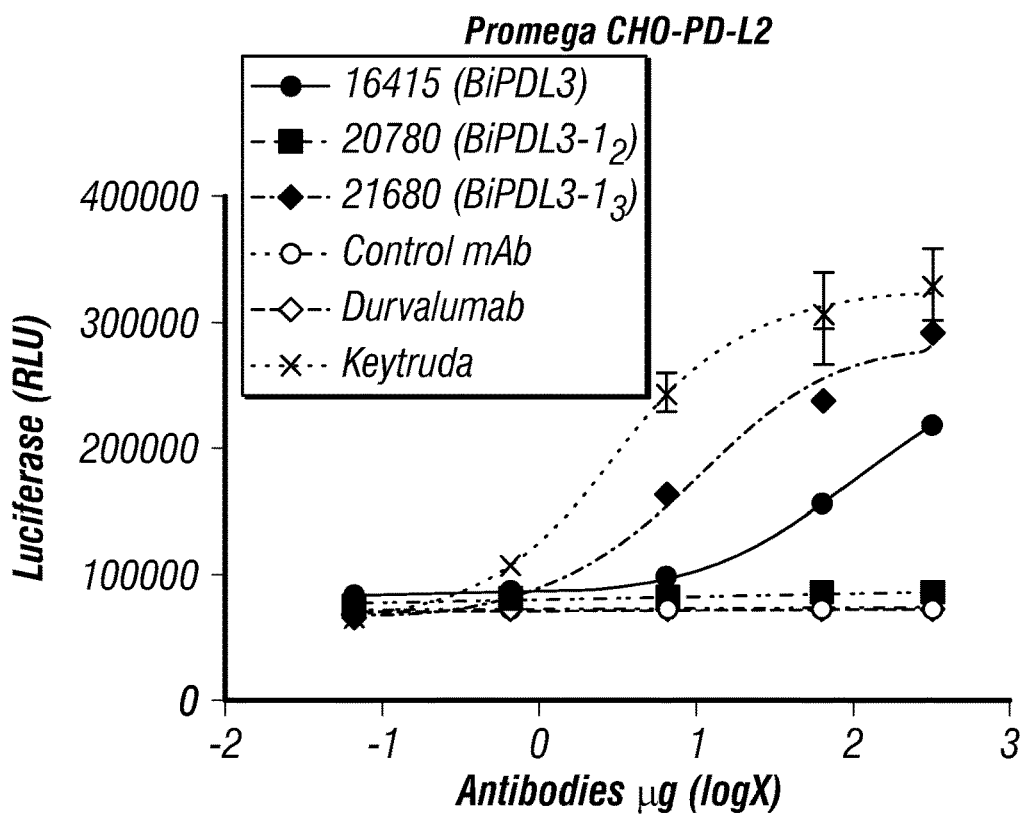
Figure 4E:
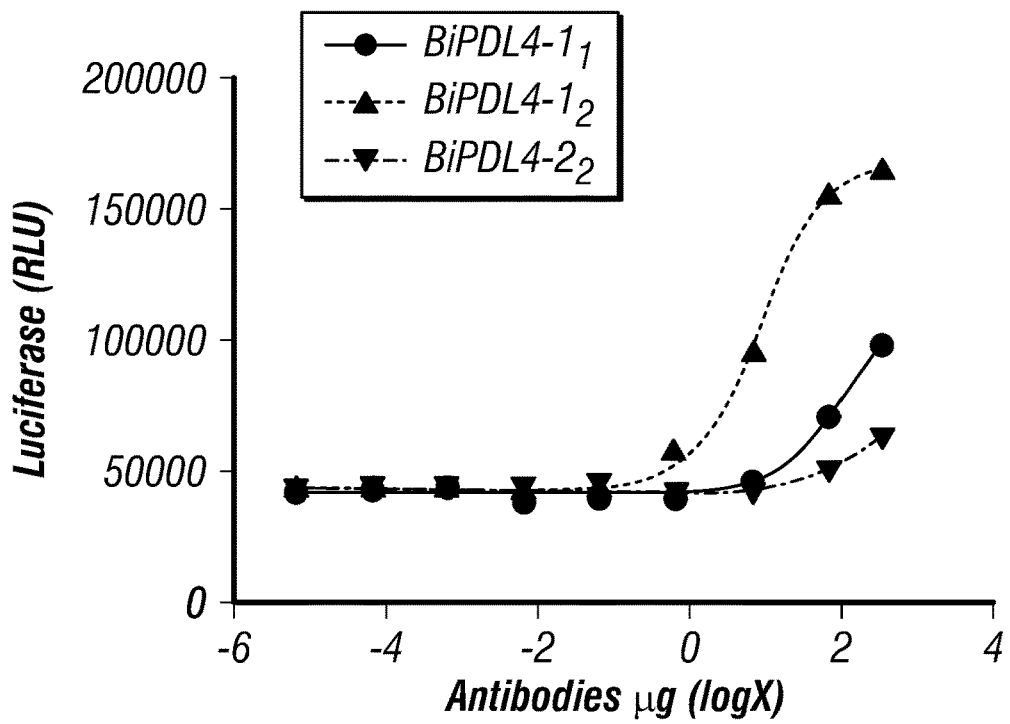
Figure 4F:
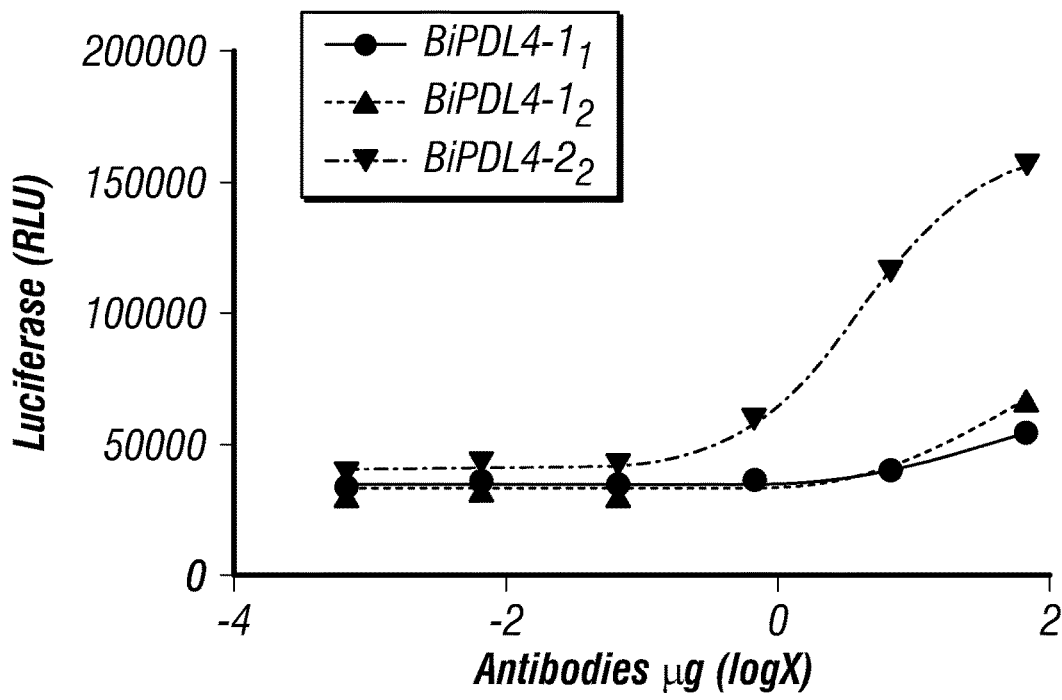

The Promega® PD-L1/PD-L2 dual expression:PD-1 assay system was used to assess the capacity of fourth generation BiPDL4 clones to restore Jurkat T cell activity (FIG. 3). BiPDL4-11, -14, -24, -34, -44 all showed similar levels of activity to Keytruda® (pembrolizumab) (anti-PD1), and outperformed Atezolizumab and Avelumab. The binding of other independent families was assessed as well (FIGS. 4A-F). The capacity of BiPDL4-12 to reverse Jurkat T cell inhibition in the Promega® system increased for both PD-L1 and PD-L2 relative to parental BiPDL4, whereas BiPDL4-22 did not gain any capacity to reverse PD-L1 mediated inhibition, but could fully reverse PD-L2 mediated suppression (FIGS. 4E-F). Octet® affinity measurements for BiPDL3-12 were Kd=2.71×10-8 PD-L1 and 8.85×10-8 PD-L2 (dimeric ligand) (Table 5). BiPDL4-12 measured 6.22×10-10 for PD-L1 and 1.74×10-9 for PD-L2, whereas BiPDL4-22 measured 8.42×10-9 for PD-L1 and 3.5×10-10 for PD-L2 (Table 5).

Figure 2C:
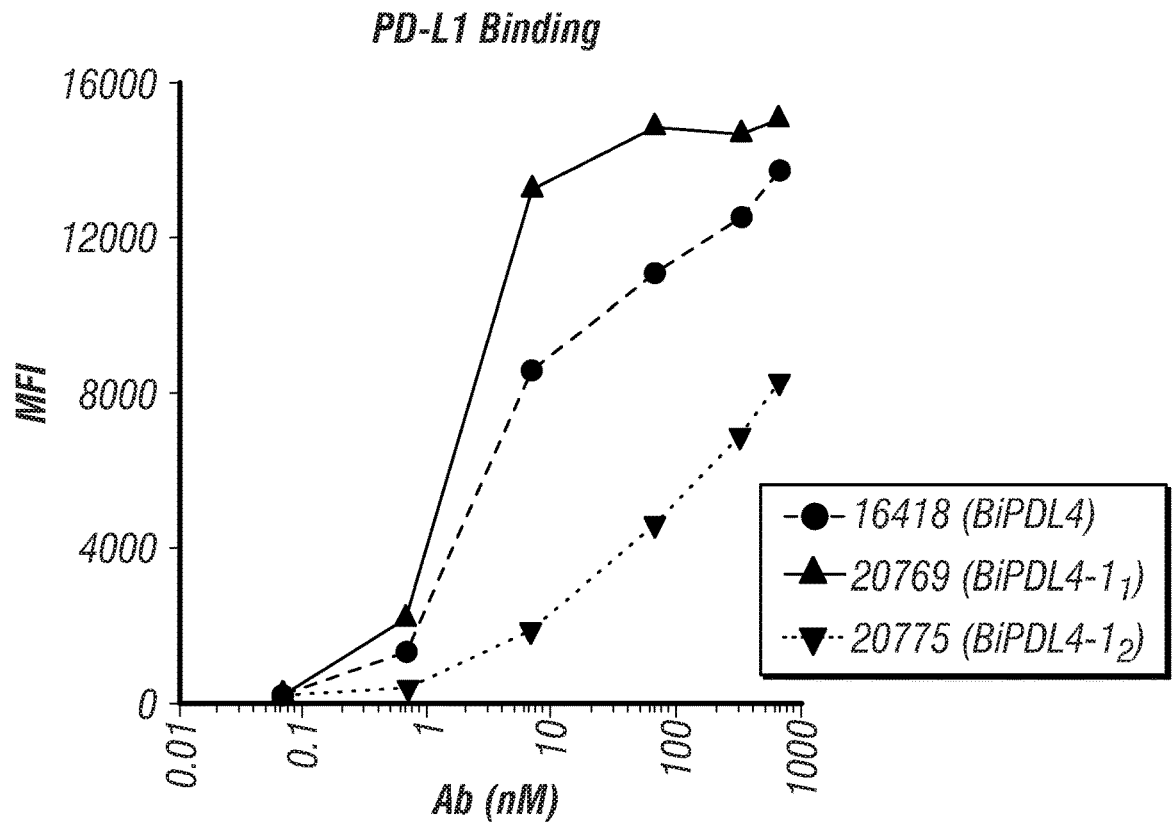

Despite improvement from the first generation of BiPDL, neither BiPDL3-12, BiPDL4-12 nor BiPDL4-22 demonstrated clinically relevant affinities for both PD-L1 and PD-L2. For this reason, a third round of heavy chain affinity maturation was performed focused on BiPDL3-12 and BiPDL4-22. This process yielded third-generation BiPDL antibodies with significantly enhanced affinities for both ligands. Octet® affinity measurements for BiPDL3-13 were Kd=3.28×10-9 for PD-L1 and 4.31×10-10 for PD-L2 (dimeric ligand). BiPDL4-13 measured 6.9×10-10 for PD-L1 and 4.9×10-10 for PD-L2 whereas BiPDL4-23 measured 1.12×10-9 for PD-L1 and 3.4×10-10 for PD-L2. BiPDL4-13 also demonstrated measurable affinity for monovalent PD-L1 (Kd=5.04×10-8) and for monovalent PD-L2 (Kd=8.36×10-9). Monovalent affinities for BiPDL4-23 were Kd=8.4×10-8 for PD-L1 and Kd=1.66×10-9 for PD-L2. All third-generation leads could potently reverse Jurkat T cell inhibition resulting from PD-L2 engagement; however, the BiPDL4 antibodies showed substantially higher capacity to reverse PD-L1 induced suppression (FIG. 2C).

Figure 2D:
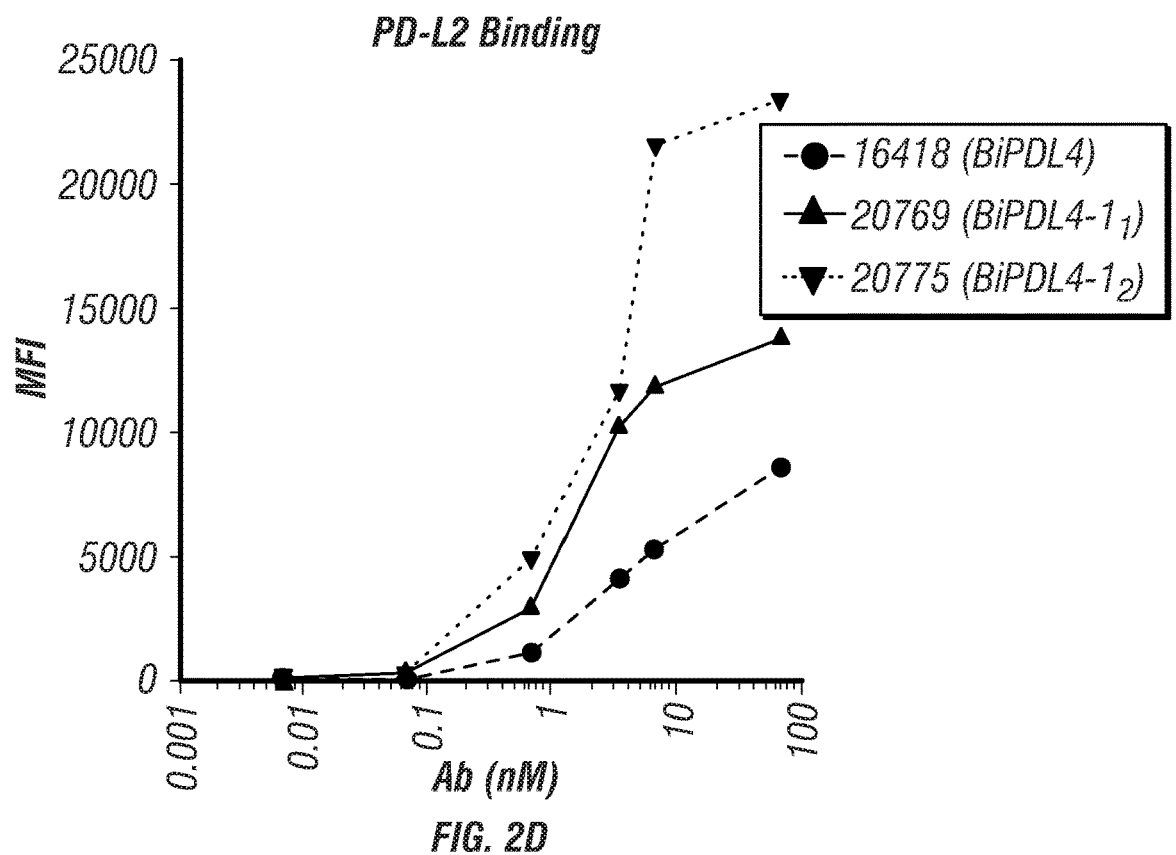

A final round of light chain affinity maturation was performed, as described in Example 1 above, in an attempt to increase the PD-L1 affinity of BiPDL4-13 and BiPDL4-23. This screen yielded a number of BiPDL leads with clinically relevant affinities for both ligands, foremost among them BiPDL4-14, BiPDL4-24, BiPDL4-34, and BiPDL4-44. Affinities of these antibodies for HIS-tagged monovalent PD-L1 measured by Octet® ranged from 2.26-7.9×10-9 for PD-L1, and 4.98-9.3×10-10 for PD-L2. When tested for their capacity to restore suppressed Jurkat T cells in the Promega® system with stimulator CHO cells expressing both PD-L1 and PD-L2, these 4th generation BiPDL4 antibodies performed similarly to Keytruda® (pembrolizumab) (FIG. 2D). In addition, these fully matured BiPDL4 demonstrated significant superiority to both earlier generations of BiPDL4 and to the FDA-approved PD-L1 antibodies atezolizumab and avelumab.

Fourth generation BiPDL4 engage a previously undescribed epitope on PD-L1. These fourth generation BiPDL4 antibodies bind with high affinity to both human and cynomolgus PD-L1 and PD-L2, and also cross-reactivity significantly with the mouse ligands (Tables 5 and 6). All four fourth generation BiPDL4 antibodies share the same heavy chain CDR3 but differ significantly in other heavy chain and light chain CDR sequences (Tables 1-4). Of note, no significant similarity exists with any of the FDA-approved PD-L1 antibodies. This lack of sequence homology suggested the potential for a unique binding specificity of these PD-L1 and PD-L2 binding antibodies, therefore they were "binned" against known PD-L1 and PD-L2 antibodies to determine their comparative epitope binding.

Antibody binning showed that all four fourth-generation BiPDL4 antibodies bind an epitope on PD-L1 entirely distinct from avelumab and atezolizumab (Table 7). Partial overlap exists with the PD-L1 epitope bound by durvalumab as evidenced by the intermediate levels of interference. All BiPDL4 bind a distinct epitope on PD-L2 relative to the commercially available clones 24F.10C12 and MIH18 (Table 8).

Figure 5A:
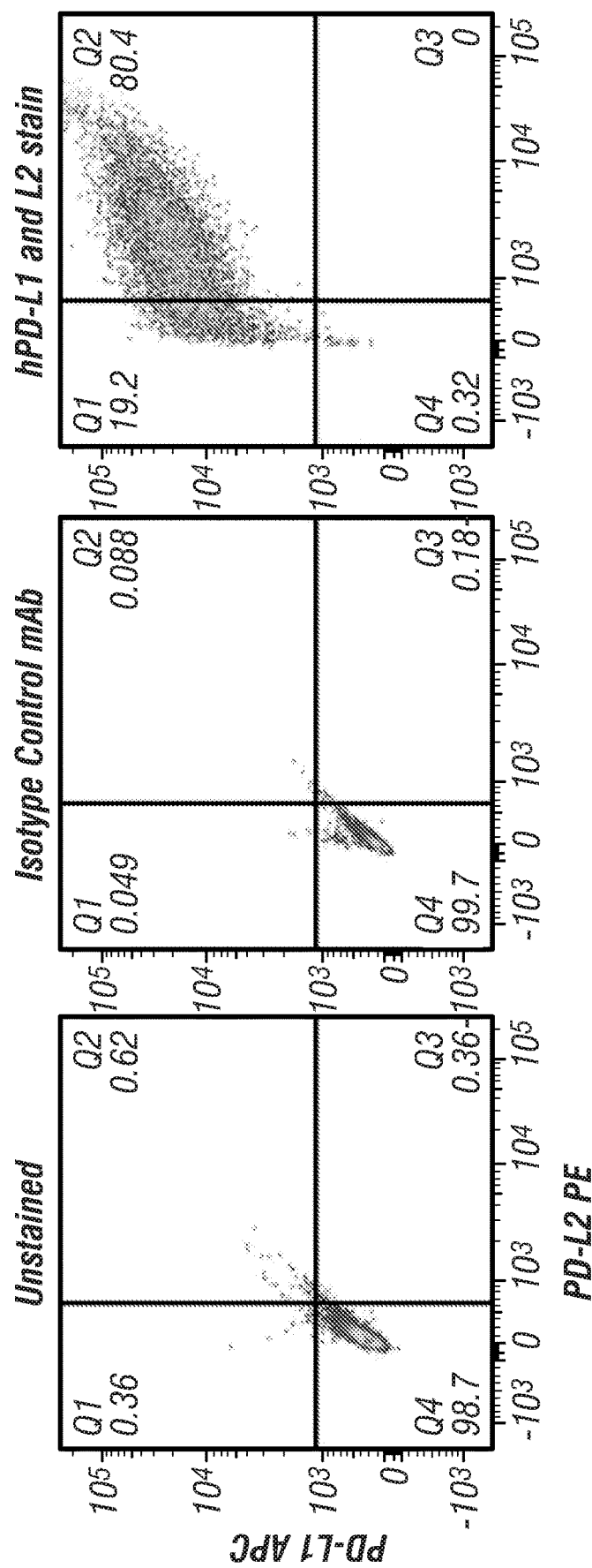
Figure 5B:
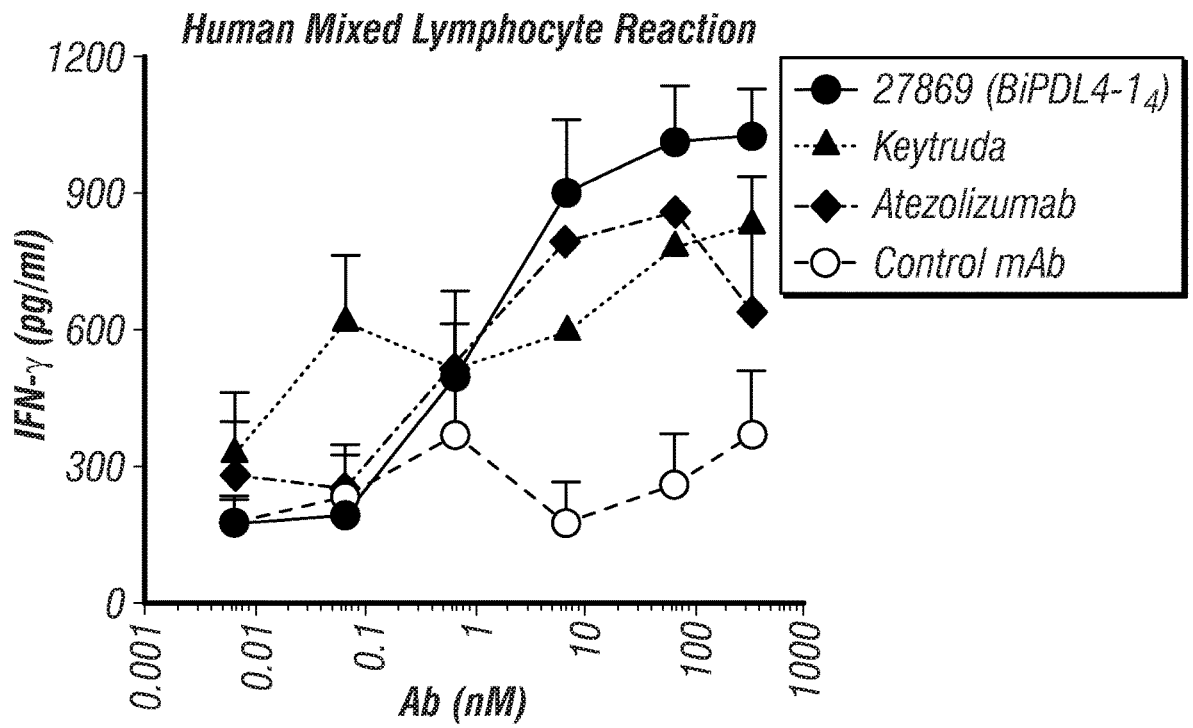
Figure 5C:
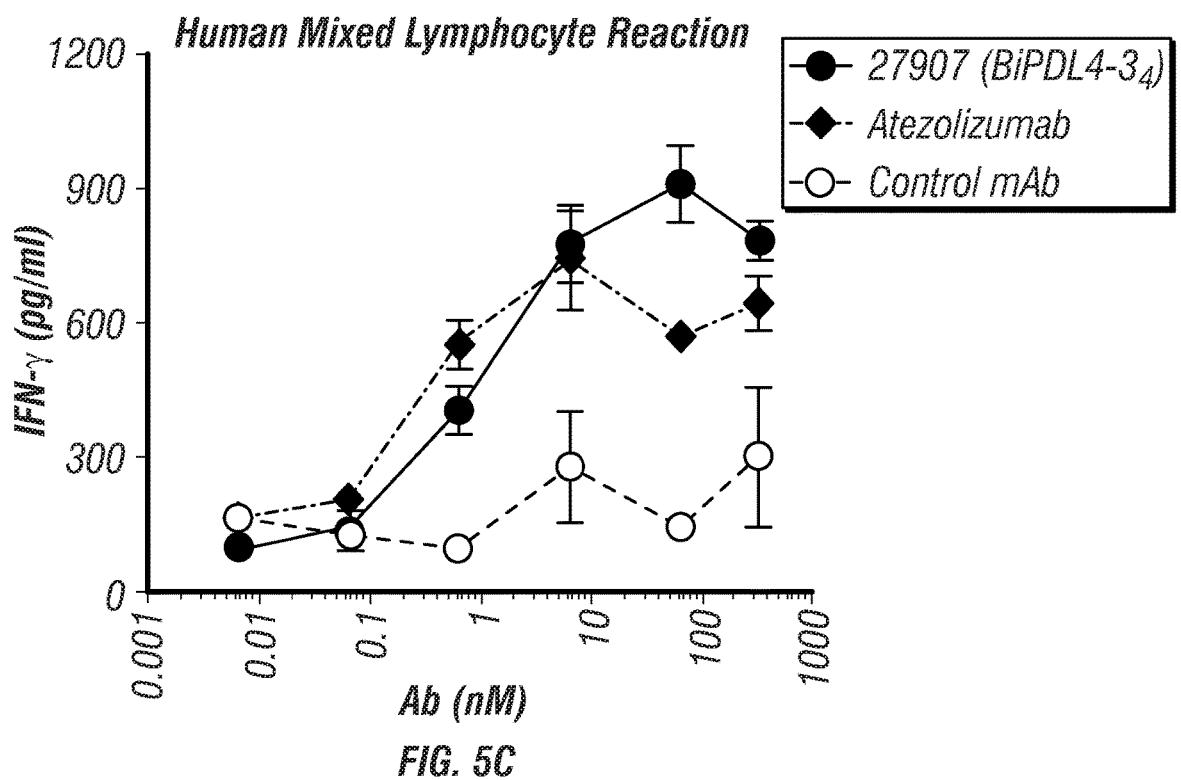

BiPDL antibodies restore effector cytokine production in primary human mixed lymphocyte reactions (MLR). Candidate antibodies, FDA approved antibodies, or control antibodies were evaluated in the presence of induced dendritic cells and T-cells from separate donors and evaluated by ELISA for IL-2 or IFN-γ production. Expression of PD-L1 and PD-L2 by the iDC were confirmed by flow cytometry (FIG. 5A). Both BiPDL4-1$_4$ and BiPDL4-3$_4$ showed similar capacity to restore IFN-γ secretion by human primary T cells as compared to FDA approved PD-L1 and PD-1 antibodies (FIGS. 5B and 5C). Despite the presence of PD-L2 in these assays, the effect of PD-L1 was found to be dominant in this context.

BiPDL antibodies with effector function mediate efficient ADCC against PD-L1 and PD-L2 expressing tumor cells. U2940 is a human primary mediastinal B lymphoma (PMBL) xenograft cell line which expresses high PD-L1 (~50,000 molecules per cell) and low to moderate levels of PD-L2 (~7,000 molecules per cell). Murine NK cells were expanded in vitro and incubated for 4 hours at a 15 to 1 effector to target ratio with Calcein-AM (Thermo Fisher®) labeled U9240 PMBL target cells and the indicated concentration of antibody. Percent specific lysis was calculated as the difference between experimental release and spontaneous release with no antibody. All generations of BiPDL3 and BiPDL4 were capable of mediating ADCC against U2940 (FIG. 6). BiPDL4-1$_2$ and BiPDL4-1$_3$ were particularly efficient at driving killing of U2940.

Effector-capable BiPDL control U2940 PBML and MDA-MB-231 tumor xenograft growth in SCID mice. 1×106 U2940 PMBL cells were implanted into SCID mice and allowed to establish until tumors reached 150 mm3. Cells were evaluated for the expression of PD-L1 and PD-L2 (FIG. 7A). Mice were then treated twice per week with 10 mg/kg of either mIgG2a control antibody, Herceptin® (trastuzumab), Rituxan® (rituximab) (U2940 is CD20+), BiPDL4-12-mIgG2a or BiPDL4-22-mIgG2a. Both BiPDL4 antibodies significantly delayed tumor growth relative to control mAb and also outperformed Rituxan® (rituximab) (FIG. 7B). The same experiment was repeated with BiPDL3-13-mIgG2a and BiPDL4-13-mIgG2a and again demonstrated significant therapeutic benefit of both BiPDL antibodies relative to controls (FIG. 7C). In this case, neither antibody significantly outperformed Rituxan® (rituximab); however, the only two mice which remain tumor free (tumor volume ≤20 mm3) at the end of the study were in the BiPDL4-13-mIgG2a group.

MDA-MB-231 triple negative breast cancer xenograft cells (TNBC) also express both PD-L1 and PD-L2 with proportions similar to U2940 (FIG. 8A). 1×10^7 MDA-MB-231 TNBC cells were implanted into SCID mice and allowed to establish until tumors reached 150 mm3. Mice were then treated twice per week with 10 mg/kg of either mIgG2a control antibody, Rituxan® (rituximab) (human IgG1 control), avelumab (human IgG1), BiPDL4-14-hIgG1, or BiPDL4-14-hIgG1[S239D/I332E] engineered for enhanced ADCC. In this setting, the BiPDL antibodies slowed progression of MDA-MB-231 xenografts with a similar capacity to the ADCC-capable PD-L1 antibody avelumab (FIG. 8B). This similarity is not surprising given the high expression of PD-L1 relative to PD-L2 by MDA-MB-231.

BiPDL treat syngeneic MC38-PD-L2 colon carcinoma more efficiently than any PD-L1 antibody. MC38 colon carcinoma cells endogenously express PD-L1 and were retrovirally engineered to express mouse PD-L2. The expression of both PD-L1 and PD-L2 was confirmed by flow cytometry (FIG. 9C). 5×10^5 MC38-PD-L2 were implanted in C57BL/6J mice. On days 3, 6, 9, 12 and 15 mice received 100 µg injections of either PBS, the rat anti-mouse PD-L1 antibody 10F.9G2, the FDA-approved PD-L1 antibodies atezolizumab and avelumab, or BiPDL4-1$_4$-hIgG1[S239D/I332E]. Survival with the BiPDL4 antibody was superior to atezolizumab (p=0.026) and to PBS (p=0.004) (FIG. 9A). Tumor growth was also slowest in mice treated with BiPDL4-1$_4$-hIgG1[S239D/I332E] (FIG. 9B).

BiPDL generate the most advantageous intra-tumoral CD8 to Treg ratios in MC38-PD-L2. 1.5×10^6 MC38-PD-L2 were implanted in C57BL/6J mice in 30% Matrigel (Corning) to facilitate recovery of infiltrating lymphocytes. The expression of PD-L1 and PD-L2 was confirmed by flow cytometry (FIG. 10A). Mice were treated as above except on days 7, 10 and 13 and then tumors were harvested and infiltrating lymphocytes analyzed by flow cytometry on day 15. In this case, BiPDL4-14-mIgG2a was used instead of the effector-enhanced human IgG1 variant. The intratumoral ratio of CD8 cytotoxic T cells relative to suppressive FoxP3+ regulatory T cells (Treg) has been established as a reliable biomarker of the success of immunotherapeutic interventions. Mice treated with BiPDL4-1$_4$-mIgG2a averaged CD8 to Treg ratios of 10, significantly higher than any of the anti-PD-L1, anti-PD-L2, anti-PD-1 or control animals (FIG. 10B).

BiPDL treat syngeneic EL4-PD-L2 T cell lymphoma more efficiently than PD-L1 or PD-L2 antibody blockade. EL4 T cell lymphoma cells also endogenously express PD-L1 and were retrovirally engineered to express mouse PD-L2. Expression of both PD-L1 and PD-L2 was confirmed by flow cytometry (FIG. 11A). 1.5×10^5 EL4-PD-L2 cells, which also express Luciferase to facilitate bioluminescent imaging, were implanted to establish systemic disease in C57BL/6J mice. On days 3, 6, 9, 12 and 15 mice received 100 µg injections of either PBS, the rat anti-mouse PD-L1 antibody 10F.9G2, the rat anti-mouse PD-L2 antibody TY25, a combination of 10F.9G2 and TY25, the FDA-approved PD-L1 antibody atezolizumab, or BiPDL4-1$_4$-mIgG2a. PD-L1 and PD-L2 blockade were ineffective in this model; however, BiPDL4 antibodies significantly extended survival (p=0.002 vs untreated; p=0.01 vs. atezolizumab) (FIG. 11B). In this setting, the effector function of the BiPDL antibody appears particularly important for efficacy, as a combination of PD-L1 and PD-L2 blocking antibodies (10F.9G2 and TY25) has no efficacy.

TABLE 1

NUCLEIC ACID SEQUENCES FOR ANTIBODY VARIABLE REGIONS

| Clone | Variable Sequence Region | SEQ ID NO: |
|---|---|---|
| 27869 Heavy BiPDL4-1$_4$ | CAGGTGCAGCTGGTGGAGTCTGGGGGAGGCGTGGTCCAGCCTGGGAG GTCCCTGAGACTCTCCTGTGCAGCGTCTGGATTCACCTTCGATGAGT ATGGCATGCACTGGGTCCGCCAGGCTCCAGGCAAGGGGCTGGAGTGG GTGGCAGTTATAGGGTATGATGGACTGAATAAATACTATGCAGACTC CGTGAAGGGCCGATTCACCATCTCCAGAGACAATTCCAAGAACACGC TGTATCTGCAAATGAACAGCCTGAGAGCCGAGGACACGGCGGTGTAC TACTGCGCCAGAGCTGGAATAGAATACAGCTACGCCTATACTGATTA CTGGGGACAGGGTACATTGGTCACCGTCTCCTCA | 3 |
| 27869 Light BiPDL4-1$_4$ | GAAATTGTGTTGACGCAGTCTCCAGGCACCCTGTCTTTGTCTCCAGG GGAAAGAGCCACCCTCTCCTGCAGGGCCAGTCAGTTCGTTTACAGCA GCGACTTAGCCTGGTACCAGCAGAAACCTGGCCAGGCTCCCAGGCTC CTCATCTATGGTGCATCCACCAGGAAAACTGGCATCCCAGACAGGTT CAGTGGCAGTGGGTCTGGGACAGACTTCACTCTCACCATCAGCAGAC TGGAGCCTGAAGATTTTGCAGTGTATTACTGTCTGCAGTTCGGATGG TGGCCTCCTAGGACTTTCGGCGGAGGGACCAAGGTGGAGATCAAA | 4 |
| 27893 Heavy BiPDL4-2$_4$ | CAGGTGCAGCTGGTGGAGTCTGGGGGAGGCGTGGTCCAGCCTGGGAG GTCCCTGAGACTCTCCTGTGCAGCGTCTGGATTCACCTTCGATGAGT ATGGCATGCACTGGGTCCGCCAGGCTCCAGGCAAGGGGCTGGAGTGG GTGGCAGTTATAGGGTATGATGGACTGAATAAATACTATGCAGACTC CGTGAAGGGCCGATTCACCATCTCCAGAGACAATTCCAAGAACACGC TGTATCTGCAAATGAACAGCCTGAGAGCCGAGGACACGGCGGTGTAC TACTGCGCCAGAGCTGGAATAGAATACAGCTACGCCTATACTGATTA CTGGGGACAGGGTACATTGGTCACCGTCTCCTCA | 5 |
| 27893 Light BiPDL4-2$_4$ | GAAATTGTGTTGACGCAGTCTCCAGGCACCCTGTCTTTGTCTCCAGG GGAAAGAGCCACCCTCTCCTGCAGGGCCAGTAACAGTGTTGTCAGCA GCTACTTAGCCIGGTACCAGCAGAAACCIGGCCAGGCTCCCAGGCTC CTCATCTATGGTCAGCCAGCAGGGCCAACGGCATCCCAGACAGGTT | 6 |

TABLE 1-continued

NUCLEIC ACID SEQUENCES FOR ANTIBODY VARIABLE REGIONS

| Clone | Variable Sequence Region | SEQ ID NO: |
|---|---|---|
| | CAGTGGCAGTGGGTCTGGGACAGACTTCACTCTCACCATCAGCAGAC TGGAGCCTGAAGATTTTGCAGTGTATTACTGTGTTCAGTTCGGATGG TGGCCTCCTAGGACTTTCGGCGGAGGGACCAAGGTGGAGATCAAA | |
| 27907 Heavy BiPDL4-3$_4$ | CAGGTGCAGCTGGTGGAGTCTGGGGGAGGCGTGATCCAGCCTGGGAG GTCCCTGAGACTCTCCTGTGCAGCGTCTGGATTCACCTTCAGTGCGT ATCTTATGCACTGGGTCCGCCAGGCTCCAGGCAAGGGGCTGGAGTGG GTGGCAGCTATAGGTTATGATGGAATGAATAAATACTATGCAGACTC CGTGAAGGGCCGATTCACCATCTCCAGAGACAATTCCAAGAACACGC TGTATCTGCAAATGAACAGCCTGAGAGCCGAGGACACGGCGGTGTAC TACTGCGCCAGAGCTGGAATAGAATACAGCTACGCCTATACTGATTA CTGGGGACAGGGTACATTGGTCACCGTCTCCTCA | 7 |
| 27907 Light BippL4-3$_4$ | GAAATTGTGTTGACGCAGTCTCCAGGCACCCTGTCTTTGTCTCCAGG GGAAAGAGCCACCCTCTCCTGCAGGGCCAGTCAGTTCGTTTACAGCA GCGACTTAGCCTGGTACCAGCAGAAACCTGGCCAGGCTCCCAGGCTC CTCATCTATGGTGCATCCGCCAGGGCCGCCGGCATCCCAGACAGGTT CAGTGGCAGTGGGTCTGGGACAGACTTCACTCTCACCATCAGCAGAC TGGAGCCTGAAGATTTTGCAGTGTATTACTGTATGCAGTTCGGATGG TGGCCTCCTAGGACTTTCGGCGGAGGGACCAAGGTTGAGATCAAA | 8 |
| 27924 Heavy BiPDL4-4$_4$ | CAGGTGCAGCTGGTGGAGTCTGGGGGAGGCGTGATCCAGCCTGGGAG GTCCCTGAGACTCTCCTGTGCAGCGTCTGGATTCACCTTCAGTGCGT ATCTTATGCACTGGGTCCGCCAGGCTCCAGGCAAGGGGCTGGAGTGG GTGGCAGCTATAGGTTATGATGGAATGAATAAATACTATGCAGACTC CGTGAAGGGCCGATTCACCATCTCCAGAGACAATTCCAAGAACACGC TGTATCTGCAAATGAACAGCCTGAGAGCCGAGGACACGGCGGTGTAC TACTGCGCCAGAGCTGGAATAGAATACAGCTACGCCTATACTGATTA CTGGGGACAGGGTACATTGGTCACCGTCTCCTCA | 9 |
| 27924 Light BiPDL4-4$_4$ | GAAATTGTGTTGACGCAGTCTCCAGGCACCCTGTCTTTGTCTCCAGG GGAAAGAGCCACCCTCTCCTGCAGGGCCAGTCACAGTGTTGTCAGCA GCTACTTAGCCTGGTACCAGCAGAAACCTGGCCAGGCTCCCAGGCTC CTCATCTATGGTGCATCCAGCAGGGAAGACGGCATCCCAGACAGGTT CAGTGGCAGTGGGTCTGGGACAGACTTCACTCTCACCATCAGCAGAC TGGAGCCTGAAGATTTTGCAGTGTATTACTGTGTGCAGTTCGGATGG TGGCCTCCTAGGACTTTCGGCGGAGGGACCAAGGTGGAGATCAAA | 10 |
| 21680 Heavy BiPDL3-1$_3$ | CAAGTACAATTACAACAGTGGGGAGCTGGTTTATTAAAGCCTTCAGA AACTTTAAGTTTGACCTGTGCTGTTTACGGTGGATCATTATCTGGTT ATCCTTGGTCTTGGATTCGTCAACCACCAGGCAAAGGATTGGAGTGG ATCGGTGAGACAGACGTGTCAGGCTGGACTGACTACAATCCAAGTTT AAAATCCAGGGTTACTATCTCCGTAGACACGTCCAAGAACCAGTTCT CCCTGAAGCTGAGTTCTGTGACCGCCGCAGACACGGCGGTGTACTAC TGCGCCAGAGACGGCAGAAGGATGGGTACCCCTTCATTCGACATATG GGGCCAGGGTACAATGGTCACCGTCTCCTCA | 11 |
| 21680 Light BiPDL3-1$_3$ | GACATCCAGTTGACCCAGTCTCCATCTTCCGTGTCTGCATCTGTAGG AGACAGAGTCACCATCACTTGTCGGGCGAGTCAGGGTATTAGCAGCT GGTTAGCCTGGTATCAGCAGAAACCAGGGAAAGCCCCTAAGCTCCTG ATCTATGCTGCATCAAGTTTGCAAAGTGGGGTCCCATCAAGGTTCAG CGGCAGTGGATCTGGGACAGATTTCACTCTCACCATCAGCAGCCTGC AGCCTGAAGATTTTGCAACTTATTACTGTCAGCAGTACGTCTACTTC CCTCCTACTTTTGGCGGAGGGACCAAGGTTGAGATCAAA | 12 |
| 20786 Heavy BiPDL2-1$_2$ | CAGGTGCAGCTGGTGCAGTCTGGGGCTGAGGTGAAGAAGCCTGGGTC CTCGGTGAAGGTCTCCTGCAAGGCTTCTGGAGGCACCTTCAGCAGCT GGTTGATCAGCTGGGTGCGACAGGCCCCTGGACAAGGGCTTGAGTGG ATGGGAGGGATCATCCCTATCCTGGGTACAGCACGGTACGCACAGAA GTTCCAGGGCAGAGTCACGATTACCGCGGACGAATCCACGAGCACAG CCTACATGGAGCTGAGCAGCCTGAGATCTGAGGACACGGCGGTGTAC TACTGCGCCAGAGTGTACAGAGCTGCTTCTTGGTTTGATCCCTGGGG ACAGGGTACATTGGTCACCGTCTCCTCA | 13 |
| 20786 Light BiPDL2-1$_2$ | GACATCCAGATGACCCAGTCTCCATCCTCCCTGTCTGCATCTGTAGG AGACAGAGTCACCATCACTTGCCAGGCGAGTCAGGACATTAGCAACT ATTTAAATTGGTATCAGCAGAAACCAGGGAAAGCCCCTAAGCTCCTG ATCTACGATGCATCCAATTTGGAAACAGGGGTCCCATCAAGGTTCAG TGGAAGTGGATCTGGGACAGATTTTACTTTCACCATCAGCAGCCTGC AGCCTGAAGATATTGCAACATATTACTGTCAGCAGCCCTTCCACCTC ATCACTTTTGGCGGAGGGACCAAGGTTGAGATCAAA | 14 |

TABLE 2

PROTEIN SEQUENCES FOR ANTIBODY VARIABLE REGIONS

| Clone | Variable Sequence | SEQ ID NO: |
|---|---|---|
| 27869 Heavy BiPDL4-1$_4$ | QVQLVESGGGVVQPGRSLRLSCAASGFTFDEYGMHWVRQAPGKGLEWVAVIGYDGLNKYYADSVKGRFTISRDNSKNTLYLQMNSLRAEDTAVYYCARAGIEYSYAYTDYWGQGTLVTVSS | 15 |
| 27869 Light BiPDL4-1$_4$ | EIVLTQSPGTLSLSPGERATLSCRASQFVYSSDLAWYQQKPGQAPRLLIYGASTRKTGIPDRFSGSGSGTDFTLTISRLEPEDFAVYYCLQFGWWPPRTFGGGTKVEIK | 16 |
| 27893 Heavy BiPDL4-2$_4$ | QVQLVESGGGVVQPGRSLRLSCAASGFTFDEYGMHWVRQAPGKGLEWVAVIGYDGLNKYYADSVKGRFTISRDNSKNTLYLQMNSLRAEDTAVYYCARAGIEYSYAYTDYWGQGTLVTVSS | 17 |
| 27893 Light BiPDL4-2$_4$ | EIVLTQSPGTLSLSPGERATLSCRASNSVVSSYLAWYQQKPGQAPRLLIYGAASRANGIPDRFSGSGSGTDFTLTISRLEPEDFAVYYCVQFGWWPPRTFGGGTKVEIK | 18 |
| 27907 Heavy BiPDL4-3$_4$ | QVQLVESGGGVIQPGRSLRLSCAASGFTFSAYLMHWVRQAPGKGLEWVAAIGYDGMNKYYADSVKGRFTISRDNSKNTLYLQMNSLRAEDTAVYYCARAGIEYSYAYTDYWGQGTLVTVSS | 19 |
| 27907 Light BiPDL4-3$_4$ | EIVLTQSPGTLSLSPGERATLSCRASQFVYSSDLAWYQQKPGQAPRLLIYGASARAAGIPDRFSGSGSGTDFTLTISRLEPEDFAVYYCMQFGWWPPRTFGGGTKVEIK | 20 |
| 27924 Heavy BiPDL4-4$_4$ | QVQLVESGGGVIQPGRSLRLSCAASGFTFSAYLMHWVRQAPGKGLEWVAAIGYDGMNKYYADSVKGRFTISRDNSKNTLYLQMNSLRAEDTAVYYCARAGIEYSYAYTDYWGQGTLVTVSS | 21 |
| 27924 Light BiPDL4-4$_4$ | EIVLTQSPGTLSLSPGERATLSCRASHSVVSSYLAWYQQKPGQAPRLLIYGASSREDGIPDRFSGSGSGTDFTLTISRLEPEDFAVYYCVQFGWWPPRTFGGGTKVEIK | 22 |
| 21680 Heavy BiPDL3-1$_3$ | QVQLQQWGAGLLKPSETLSLTCAVYGGSLSGYPWSWIRQPPGKGLEWIGETDVSGWTDYNPSLKSRVTISVDTSKNQFSLKLSSVTAADTAVYYCARDGRRMGTPSFDIWGQGTMVTVSS | 23 |
| 21680 Light BiPDL3-1$_3$ | DIQLTQSPSSVSASVGDRVTITCRASQGISSWLAWYQQKPGKAPKLLIYAASSLQSGVPSRFSGSGSGTDFTLTISSLQPEDFATYYCQQYVYFPPTFGGGTKVEIK | 24 |
| 20786 Heavy BiPDL2-1$_2$ | QVQLVQSGAEVKKPGSSVKVSCKASGGTFSSWLISWVRQAPGQGLEWMGGIIPILGTARYAQKFQGRVTITADESTSTAYMELSSLRSEDTAVYYCARVYRAASWFDPWGQGTLVTVSS | 25 |
| 20786 Light BiPDL2-1$_2$ | DIQMTQSPSSLSASVGDRVTITCQASQDISNYLNWYQQKPGKAPKLLIYDASNLETGVPSRFSGSGSGTDFTFTISSLQPEDIATYYCQQPFHLITFGGGTKVEIK | 26 |
| 37464 Heavy BiPDL3-1$_4$ | QVQLQQWGAGLLKPSETLSLTCAVYGGSLSGYPWSWIRQPPGKGLEWIGETDVSGWTDYNPSLKSRVTISVDTSKNQFSLKLSSVTAADTAVYYCARDGRRMGTPSFDIWGQGTMVTVSS | 63 |
| 37464 Light BiPDL3-1$_4$ | DIQMTQSPSSVSASVGDRVTITCRASQGINSFLAWYQQKPGKAPKLLIYAASSLNSGVPSRFSGSGSGTDFTLTISSLQPEDFATYYCQKAVYFPPTFGGGTKVEIK | 64 |
| 37465 Heavy BiPDL3-2$_4$ | QVQLQQWGAGLLKPSETLSLTCAVYGGSLSGYPWSWIRQPPGKGLEWIGETDVSGWTDYNPSLKSRVTISVDTSKNQFSLKLSSVTAADTAVYYCARDGRRMGTPSFDIWGQGTMVTVSS | 65 |
| 37465 Light BiPDL3-2$_4$ | DIQMTQSPSSVSASVGDRVTITCRASQGISNFLAWYQQKPGKAPKLLIYAASSLQSGVPSRFSGSGSGTDFTLTISSLQPEDFATYYCQKAVYFPPTFGGGTKVEIK | 66 |
| 37468 Heavy BiPDL3-3$_4$ | QVQLQQWGAGLLKPSETLSLTCAVYGGSLSGYPWSWIRQPPGKGLEWIGETDVSGWTDYNPSLKSRVTISVDTSKNQFSLKLSSVTAADTAVYYCARDGRRMGTPSFDIWGQGTMVTVSS | 67 |
| 37468 Light BiPDL3-3$_4$ | DIQMTQSPSSVSASVGDRVTITCRASQDISSFLAWYQQKPGKAPKLLIYAASSLQDGVPSRFSGSGSGTDFTLTISSLQPEDFATYYCQKSVYFPPTFGGGTKVEIK | 68 |

TABLE 2-continued

PROTEIN SEQUENCES FOR ANTIBODY VARIABLE REGIONS

| Clone | Variable Sequence | SEQ ID NO: |
|---|---|---|
| 37475 Heavy BiPDL3-4$_4$ | QVQLQQWGAGLLKPSETLSLTCAVYGGSLSGYPWSWIRQPPGKGLEW IGETDVSGWTDYNPSLKSRVTISVDTSKNQFSLKLSSVTAADTAVYY CARDGRRMGTPSFDIWGQGTMVTVSS | 69 |
| 37475 Light BiPDL3-4$_4$ | DIQMTQSPSSVSASVGDRVTITCRASQGISTFLAWYQQKPGKAPKLL IYAASALHSGVPSRFSGSGSGTDFTLTISSLQPEDFATYYCQRAVYF PPTFGGGTKVEIK | 70 |
| 37477 Heavy BiPDL3-5$_4$ | QVQLQQWGAGLLKPSETLSLTCAVYGGSLSGYPWSWIRQPPGKGLEW IGETDVSGWTDYNPSLKSRVTISVDTSKNQFSLKLSSVTAADTAVYY CARDGRRMGTPSFDIWGQGTMVTVSS | 71 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 27869 BiPDL4-1$_4$ | FTFDEYGMH (27) | VIGYDGLNKYYADSVKG (28) | ARAGIEYSYAYTDY (29) |
| 27893 BiPDL4-2$_4$ | FTFDEYGMH (30) | VIGYDGLNKYYADSVKG (31) | ARAGIEYSYAYTDY (32) |
| 27907 BiPDL4-3$_4$ | FTFSAYLMH (33) | AIGYDGMNKYYADSVKG (34) | ARAGIEYSYAYTDY (35) |
| 27924 BiPDL4-4$_4$ | FTFSAYLMH (36) | AIGYDGMNKYYADSVKG (37) | ARAGIEYSYAYTDY (38) |
| 21680 BiPDL3-1$_3$ | GSLSGYPWS (39) | ETDVSGWTDYNPSLKS (40) | ARDGRRMGTPSFDI (41) |
| 20786 BiPDL2-1$_2$ | GTFSSWLIS (42) | GIIPILGTARYAQKFQG (43) | ARVYRAASWPDP (44) |
| 37464 BiPDL3-1$_4$ | GSLSGYPWS (72) | ETDVSGWTDYNPSLKS (73) | ARDGRRMGTPSFDI (74) |
| 37465 BiPDL3-2$_4$ | GSLSGYPWS (75) | ETDVSGWTDYNPSLKS (76) | ARDGRRMGTPSFDI (77) |
| 37468 BiPDL3-3$_4$ | GSLSGYPWS (78) | ETDVSGWTDYNPSLKS (79) | ARDGRRMGTPSFDI (80) |
| 37475 BiPDL3-4$_4$ | GSLSGYPWS (81) | ETDVSGWTDYNPSLKS (82) | ARDGRRMGTPSFDI (83) |
| 37477 BiPDL3-5$_4$ | GSLSGYPWS (84) | ETDVSGWTDYNPSLKS (85) | ARDGRRMGTPSFDI (86) |

TABLE 4

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| 27869 BiPDL4-1$_4$ | RASQFVYSSDLA (45) | GASTRKT (46) | LQFGWWPPRT (47) |
| 27893 BiPDL4-2$_4$ | RASNSVVSSYLA (48) | GAASRAN (49) | VQFGWWPPRT (50) |
| 27907 BiPDL4-3$_4$ | RASQFVYSSDLA (51) | GASARAA (52) | MQFGWWPPRT (53) |
| 27924 BiPDL4-4$_4$ | RASHSVVSSYLA (54) | GASSRED (55) | VQFGWWPPRT (56) |
| 21680 BiPDL3-1$_3$ | RASQGISSWLA (57) | AASSLQS (58) | QQYVYFPPT (59) |
| 20786 BiPDL2-1$_2$ | QASQDISNYLN (60) | DASNLET (61) | QQPFHLIT (62) |
| 37464 BiPDL3-1$_4$ | RASQGINSFLA (87) | AASSLNS (88) | QKAVYFPPT (89) |
| 37465 BiPDL3-2$_4$ | RASQGISNFLA (90) | AASSLQS (91) | QKAVYFPPT (92) |
| 37468 BiPDL3-3$_4$ | RASQDISSFLA (93) | AASSLQD (94) | QKSVYFPPT (95) |
| 37475 BiPDL3-4$_4$ | RASQGISTFLA (96) | AASALHS (97) | QRAVYFPPT (98) |
| 37477 BiPDL3-5$_4$ | RASKGISSFLA (99) | AADSIQS (100) | QSAVYFPPT (101) |

TABLE 5

BiPDL NOMENCLATURE

| BiPDL nomenclature | ADI experimental numbering |
|---|---|
| BiPDL1 | 16413 |
| BiPDL2 | 16414 |
| BiPDL2-1$_2$ | 20786 |
| BiPDL3 | 16415 |
| BiPDL3-1$_2$ | 20780 |
| BiPDL3-1$_3$ | 21680 |
| BiPDL4-1$_1$ | 16418 |
| BiPDL4-1$_2$ | 20769 |
| BiPDL4-2$_2$ | 20775 |
| BiPDL4-1$_3$ | 21661 |
| BiPDL4-1$_4$ | 27869 |

TABLE 5-continued

BiPDL NOMENCLATURE

| BiPDL nomenclature | ADI experimental numbering |
|---|---|
| BiPDL4-2$_4$ | 27893 |
| BiPDL4-3$_4$ | 27907 |
| BiPDL4-4$_4$ | 27924 |
| BiPDL3-1$_4$ | 37464 |
| BiPDL3-2$_4$ | 37465 |
| BiPDL3-3$_4$ | 37468 |
| BiPDL3-4$_4$ | 37475 |
| BiPDL3-5$_4$ | 37477 |

TABLE 5

AFFINITY MEASUREMENTS OF ANTIBODY BINDING TO PD-L1 AND PD-L2

| Clone Family | Target | ADI Name | IgG $K_D$ Human PD-L1-Fc (M) Avid | IgG $K_D$ Human PD-L1-HIS (M) Avid | Fab $K_D$ Human PD-L1-Fc (M) Monovalent | IgG $K_D$ Human PD-L2-Fc (M) Avid | IgG $K_D$ Human PD-L2-HIS (M) Monovalent | Fab $K_D$ Human PD-L2-Fc (M) Monovalent |
|---|---|---|---|---|---|---|---|---|
| 52 | PD-L1/L2 | ADI-16415 | 7.29E−09 | P.F. | N.B. | 7.97E−10 | 1.07E−07 | 5.34E−08 |
| 52-g1 | PD-L1/L2 | ADI-20780 | 2.71E−08 | N.D. | N.B. | 8.85E−08 | N.D. | N.B. |
| 52-g2 | PD-L1/L2 | ADI-21680 | 3.28E−09 | N.D. | P.F. | 4.31E−10 | N.D. | 1.60E−08 |
| 53 | PD-L1/L2 | ADI-16418 | 9.84E−10 | 7.69E−10 | 7.83E−08 | 2.42E−09 | P.F. | 1.18E−07 |
| 53-g1 | PD-L1/L2 | ADI-20769 | 6.22E−10 | N.D. | 2.79E−08 | 1.74E−09 | N.D. | 9.84E−08 |
| 53-g1 | PD-L1/L2 | ADI-20775 | 8.42E−09 | N.D. | N.B. | 3.50E−10 | N.D. | 1.11E−08 |
| 53-g2 | PD-L1/L2 | ADI-21661 | 6.36E−10 | N.D. | 5.04E−08 | 3.39E−10 | N.D. | 8.36E−09 |
| 53-g3 | PD-L1/L2 | ADI-27869 | N.D. | 6.92E−10 | 2.26E−09 | N.D. | 7.38E−10 | 4.02E−10 |
| 53-g3 | PD-L1/L2 | ADI-27907 | N.D. | 2.17E−09 | 6.85E−09 | N.D. | 9.32E−10 | 5.60E−10 |

| Clone Family | IgG $K_D$ Cyno PD-L1-Fc (M) Avid | IgG $K_D$ Mouse PD-L1-Fc (M) Avid | IgG $K_D$ Cyno PD-L2-Fc (M) Avid | IgG $K_D$ Mouse PD-L2-Fc (M) Avid | IgG $K_D$ Human PD1-Fc (M) Avid | MSD Fab $K_D$ Human b-PD-L1-His (M) Monovalent | MSD Fab $K_D$ Human b-PD-L2-His (M) Monovalent |
|---|---|---|---|---|---|---|---|
| 52 | P.F. | N.B. | 8.24E−10 | P.F. | N.B. | | |
| 52-g1 | P.F. | N.B. | 4.57E−08 | P.F. | N.B. | | |
| 52-g2 | 2.34E−09 | N.B. | 6.88E−10 | 1.22E−09 | N.B. | | |
| 53 | 1.21E−08 | 9.45E−10 | 6.64E−09 | N.B. | N.B. | | |
| 53-g1 | 6.05E−10 | 4.50E−10 | 3.22E−09 | N.B. | N.B. | | |
| 53-g1 | 7.33E−09 | 4.57E−09 | 8.55E−10 | 1.99E−08 | N.B. | | |
| 53-g2 | 7.10E−10 | 6.29E−10 | 6.18E−10 | P.F. | N.B. | | |
| 53-g3 | 5.08E−10 | 4.00E−10 | 6.40E−10 | 7.88E−09 | N.B. | 1.20E−10 | 1.1E−10 |
| 53-g3 | 4.08E−10 | 5.44E−10 | 7.39E−10 | 5.69E−09 | N.B. | 9.60E−10 | 5.2E−11 |

TABLE 6

AFFINITY MEASUREMENTS OF ANTIBODY BINDING TO PD-L1 AND PD-L2

| BiPDL Name | ForteBio IgG $K_D$ Human PD-L1-His (M) Monovalent | ForteBio Fab $K_D$ Human PD-L1-Fc (M) Monovalent | ForteBio IgG $K_D$ Human PD-L2-His (M) Monovalent | ForteBio Fab $K_D$ Human PD-L2-(M) Monovalent | ForteBio IgG $K_D$ Cyno PD-L1-Fc (M) Avid | ForteBio IgG $K_D$ Cyno PD-L2-Fc (M) Avid | ForteBio IgG $K_D$ mouse PD-L1-Fc (M) Avid | ForteBio IgG $K_D$ mouse PD-L2-Fc (M) Avid | MSD Fab $K_D$ Human b-PD-L1-His (M) Monovalent | MSD Fab $K_D$ Human b-PD-L2-His (M) Monovalent |
|---|---|---|---|---|---|---|---|---|---|---|
| BiPDL4-1$_4$ | 2.26E−09 | 6.92E−10 | 7.38E−10 | 4.02E−10 | 5.08E−10 | 6.40E−10 | 4.00E−10 | 7.88E−09 | 1.20E−10 | 1.1E−10 |
| BiPDL4-2$_4$ | 7.24E−09 | 6.57E−09 | 4.97E−10 | 4.75E−10 | 8.38E−10 | 4.58E−10 | 6.77E−10 | 6.77E−09 | N.D. | 1.2E−10 |
| BiPDL4-3$_4$ | 6.85E−09 | 2.17E−09 | 9.32E−10 | 5.60E−10 | 4.08E−10 | 7.39E−10 | 5.44E−10 | 5.69E−09 | 9.60E−10 | 5.2E−11 |
| BiPDL4-4$_4$ | 7.89E−09 | 6.00E−09 | 8.89E−10 | 4.37E−10 | 5.55E−10 | 4.17E−10 | 7.93E−10 | 4.14E−09 | N.D. | 1.5E−10 |

TABLE 7

ANTIBODY OVERLAP DETERMINATION BY BINNING

| Antibody | PDL1-3$_1$ | PDL1-4$_1$ | PDL1-1$_2$ | BiPDL4-1$_1$ | BiPDL4-1$_2$ | BiPDL4-1$_3$ | BiPDL4-1$_4$ | MedImmune | Tecentriq | Avelumab |
|---|---|---|---|---|---|---|---|---|---|---|
| PDL1-3$_1$ | 0.68% | 9.67% | 2.86% | 3.59% | 0.89% | 1.40% | 0.61% | 1.03% | 0.75% | 2.39% |
| PDL1-4$_1$ | −0.07% | 4.19% | 0.60% | 17.19% | −0.14% | 8.21% | −0.42% | 0.65% | −0.52% | 0.37% |
| PDL1-1$_2$ | 2.03% | 8.01% | 2.24% | 3.31% | 1.69% | 2.19% | 1.62% | 2.38% | 1.86% | 3.14% |
| BiPDL4-1$_1$ | 1.73% | 38.51% | 1.98% | 2.41% | 0.99% | 1.08% | 0.76% | 2.12% | 81.22% | 78.95% |
| BiPDL4-1$_2$ | 3.89% | 15.84% | 5.48% | 7.53% | 1.81% | 2.60% | 2.04% | 4.47% | 83.74% | 83.62% |
| BiPDL4-1$_3$ | 2.68% | 20.71% | 4.31% | 6.52% | 1.25% | 1.97% | 1.06% | 2.85% | 82.45% | 80.19% |
| BiPDL4-1$_4$ | 4.85% | 15.88% | 5.90% | 8.98% | 2.61% | 3.02% | 1.65% | 5.37% | 81.58% | 82.55% |
| MedImmune | 1.31% | 7.75% | 1.69% | 3.37% | 0.72% | 1.23% | 0.95% | 0.81% | 0.60% | 1.98% |
| Tecentriq | 1.12% | 8.57% | 2.28% | 84.41% | 87.62% | 84.48% | 80.19% | 1.88% | 0.33% | 1.88% |
| Avelumab | 0.52% | 7.59% | 1.67% | 86.15% | 85.69% | 84.99% | 81.03% | 1.62% | 0.67% | 1.48% |

TABLE 8

ANTIBODY OVERLAP DETERMINATION BY BINNING

| Antibody | PDL2-2$_1$ | BiPDL4-1$_1$ | BiPDL4-1$_2$ | BiPDL4-1$_3$ | BiPDL4-1$_4$ | PDL2-1$_3$ | PDL2-2$_3$ | MIH18 | 24F.10C12 | PDL2-1$_3$ |
|---|---|---|---|---|---|---|---|---|---|---|
| PDL2-2$_1$ | 3.94% | 61.01% | 60.34% | 59.36% | 61.96% | 1.87% | 2.22% | 57.40% | 1.92% | 0.49% |
| BiPDL4-1$_1$ | 70.16% | 6.14% | 7.10% | 6.56% | 5.65% | 67.19% | 66.57% | 15.10% | 51.91% | 76.14% |
| BiPDL4-1$_2$ | 71.50% | 4.58% | 4.61% | 4.65% | 3.44% | 68.76% | 65.25% | 12.56% | 54.25% | 72.66% |
| BiPDL4-1$_3$ | 73.53% | 4.37% | 5.12% | 5.22% | 4.00% | 69.12% | 64.50% | 15.16% | 60.28% | 76.10% |
| BiPDL4-1$_4$ | 73.14% | 6.90% | 7.31% | 8.06% | 5.52% | 68.78% | 64.87% | 17.08% | 58.89% | 68.66% |
| PDL2-1$_3$ | 6.06% | 68.20% | 65.56% | 66.74% | 70.90% | 5.10% | 5.81% | 65.85% | 7.44% | 5.70% |
| PDL2-2$_3$ | 2.25% | 58.24% | 59.37% | 60.54% | 60.75% | 4.39% | 3.54% | 63.79% | 4.39% | 3.21% |
| MIH18 | 74.65% | 47.93% | 60.62% | 57.01% | 63.38% | 73.65% | 70.26% | 5.73% | 71.43% | 82.48% |
| 24F.10C12 | 5.24% | 50.46% | 57.49% | 56.89% | 62.84% | 7.11% | 5.98% | 63.75% | 4.99% | 6.30% |
| PDL2-1$_3$ | 5.84% | 67.97% | 68.71% | 67.46% | 73.22% | 6.40% | 6.25% | 66.70% | 6.89% | 4.64% |

TABLE 9

ANTIBODY BINDING AND COMPETITION

| ADI Name | Lineage Name | IgG KD Human PD-L1-HIS (M) Monovalent | IgG KD Human PD-L2-HIS (M) Monovalent | IgG K$_D$ Cyno PD-L1-Fc (M) Avid | IgG KD Cyno PD-L2-Fc (M) Avid | IgG KD Mouse PD-L1-Fc (M) Avid | IgG KD Mouse PD-L2-Fc (M) Avid | PD-1 competitor (human PD-L1) | CD80 competitor (human PD-L1) |
|---|---|---|---|---|---|---|---|---|---|
| ADI-37464 | BiPDL3-1$_4$ | 3.93E−09 | 6.84E−10 | 3.71E−10 | 5.43E−10 | 2.34E−09 | 5.33E−10 | Yes | Yes |
| ADI-37465 | BiPDL3-2$_4$ | 1.34E−08 | 8.68E−10 | 3.96E−10 | 6.05E−10 | 2.65E−09 | 5.53E−10 | Yes | Yes |
| ADI-37468 | BiPDL3-3$_4$ | 1.78E−08 | 8.44E−10 | 4.31E−10 | 6.77E−10 | 3.16E−08 | 4.84E−10 | Yes | Yes |
| ADI-37475 | BiPDL3-4$_4$ | 3.02E−08 | 1.45E−09 | 4.55E−10 | 6.03E−10 | 4.20E−08 | 5.52E−10 | Yes | Yes |
| ADI-37477 | BiPDL3-5$_4$ | 1.55E−08 | 2.20E−09 | 4.42E−10 | 6.21E−10 | 2.97E−09 | 6.94E−10 | Yes | Yes |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, NY, 1988.
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Austin et al., *PLoS Pathog* 8, e1002930, 2012.
Baptista et al., *Hum. Pathol.*, 47: 78-84, 2016.
Barrett et al., *Oncotarget*, 6: 26483-26493, 2015.
Boussiotis, *N Engl J Med*, 375: 1767-1778, 2016.
Boyerinas et al., *Cancer Immunol. Res.*, 3: 1148-1157, 2015.
Brahmer et al., *J. Clin. Oncolo.*, 28:3167-3175, 2010.

Brahmer et al., *N. Eng. J. Med*, 366:2455-2465; 2012.
Brehin, et al., *Virology* 371:185-195, 2008.
Brown et al., *J. Immunol. Meth.*, 12; 130(1): 111-121, 1990.
Butte et al., *Immunity*, 27: 111-122, 2007.
Butte et al., *Mol. Immunol.*, 45: 3567-3572, 2008.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
Cheng et al., *J. Biol. Chem.*, 288: 11771-11785, 2013.
Christian et al., *Proc Natl Acad Sci USA*, 110:18662-18667, 2013.
Danilova et al., *Proc. Natl. Acad. Sci. U.S.A*, 113: E7769-E7777, 2016.
De Jager et al., *Semin. Nucl. Med.* 23(2): 165-179, 1993.
Derks et al., *Cancer. Immunol. Res.*, 3: 1123-1129, 2015.
Dholakia et al., *J. Biol. Chem.*, 264, 20638-20642, 1989.
Doolittle and Ben-Zeev, *Methods Mol. Biol.*, 109, 215-237, 1999.
Dong et al., *Hum. Pathol.*, 2016.
Dong et al, *Nat. Medicine*, 8:793-800, 2002.
Estep et al., *Mabs*, 5(2): 270-278, 2013.
Fric et al., *J. Infect. Dis.* 207:319-322, 2013.
Gefter et al., *Somatic Cell Genet.*, 3:231-236, 1977.
Goh et al., *Clin. Immunol.* 149:487-497, 2013.
Green et al., *Blood*, 116: 3268-3277, 2010.
Gulbis and Galand, *Hum. Pathol.* 24(12), 1271-1285, 1993.
Guo et al., *Sci. Transl. Med.* 3:99 ra85, 2001.
Howitt et al., *J.A.M.A. Oncol.*, 2: 518-522, 2016.
Inoue et al., *Oncotarget*, 7: 32113-32128, 2016.
Kam et al., *EMBO Mol. Med.* 4, 330-343, 2012b.
Kam et al., *J. Virol.* 86, 13005-13015, 2012a.
Kam et al., *PLoS One* 9, e95647, 2014.
Khatoon et al., *Ann. of Neurology*, 26, 210-219, 1989.
Kim et al., *Lung Cancer*, 88: 24-33, 2015.
Kim et al., *Eur. J. Cancer*, 51: 2698-2707, 2015.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kyte and Doolittle, *J. Mol. Biol.*, 157(1):105-132, 1982.
Lanciotti & Valadere, *Emerg Infect Dis* 20, 2014.
Latchman et al., *Nat. Immunol.*, 2: 261-268, 2001.
Lee et al., *Nat. Commun.*, 7: 12220, 2016.
Lee et al., *PLoS Pathog.* 7:e1002390, 2011.
Levitt et al., *Vaccine* 4, 157-162, 1986.
Li et al., *J. Biol. Chem.*, 292: 6799-6809, 2017.
Lum et al., *J. Immunol.* 190:6295-6302, 2013.
Mainou et al., *MBio* 4, 2013.
Masrinoul et al., *Virology* 464-465, 111-117, 2014.
Messer et al., *Proc. Natl. Acad. Sci. USA* 111:1939-1944, 2014.
Morrison et al., *Am J Pathol*, 178:32-40, 2011.
Nakamura et al., In: *Enzyme Immunoassays: Heterogeneous and Homogeneous Systems*, Chapter 27, 1987.
Nazareth et al., *J. Immunology*, 178(9): 5552-5562, 2007.
Nie et al., *Cell Mol. Immunol.*, 2017.
Nomi et al., *Clin. Cancer Res.*, 13: 2151-2157, 2007.
Obeid et al., *Oncoimmunology*, 5: e1235107, 2016.
Ohigashi et al., *Clin. Cancer Res.*, 11: 2947-2953, 2005.
O'Shannessy et al., *J. Immun. Meth.*, 99, 153-161, 1987.
Paes et al., *J. Am. Chem. Soc.*, 131:6952-6954, 2009.
Pal et al., *PLoS Pathog* 9, e1003312, 2013.
Persic et al., *Gene* 187:1, 1997
Pinchuk et al., *Gastroenterology*, 135(4): 1228-1237, 2008.
Potter and Haley, *Meth. Enzymol.*, 91, 613-633, 1983.
Remington's Pharmaceutical Sciences, 15th Ed., 3:624-652, 1990.
Roemer et al., *J. Clin. Oncol.*, 2016.
Rozali et al., *Clinical and Developmental Immunology*; 2012: 656340, 2012.
R. C. Team, R Foundation for Statistical Computing, Vienna, Austria, 2014.
Schilte et al., *PLoS Negl. Trop. Dis.* 7:e2137, 2013.
Selvarajah et al., *PLoS Negl. Trop. Dis.* 7:e2423, 2013.
Siegel et al., *J Immunol Methods*, 286(1-2): 141-153, 2004.
Shi et al., *Am. J. Surg. Pathol.*, 38: 1715-1723, 2014.
Shin et al., *Ann. Surg. Oncol.*, 2015.
Shin et al., *Ann. Surg. Oncol.*, 23: 694-702, 2016.
Sissoko et al., *PLoS Negl. Trop. Dis.* 3:e389, 2009.
Smith et al., *MBio* 4, e00873-00813, 2013a.
Sun et al., *Elife* 2:e00435, 2013.
Sun et al., *J. Steroid Biochem.*, 26(1):83-92, 1987.
Sunshine and Taube, *Curr. Opin. Pharmacol.*, 23: 32-38, 2015.
Tang et al., *J. Biol. Chem.*, 271:28324-28330, 1996.
Thompson et al., *Proceedings of the National Academy of Sciences of the U.S.A.*, 101(49):17174-17179, 2004.
Thornburg et al., *J. Clin. Invest.*, 123:4405-4409, 2013.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
Vander Veen et al., *Anim Health Res Rev*, 13:1-9, 2012.
Van Deventer and Wittrup, *Methods Mol. Biol.*, 1131: 151-181, 2014.
Van Roosbroeck et al., *Genes Chromosomes Cancer*, 55: 428-441, 2016.
Voss et al., *Nature*, 468:709-712, 2010.
Wang et al., *World J. Gastroenterol.*, 17: 3322-3329, 2011.
Warter et al., *J. Immunol.*, 186:3258-3264, 2011.
Wawrzynczak & Thorpe, In: *Immunoconjugates, Antibody Conjugates In Radioimaging And Therapy Of Cancer*, Vogel (Ed.), NY, Oxford University Press, 28, 1987.
Xiao et al., *J. Exp. Med.*, 211: 943-959, 2014.
Xu et al., *PEDS* 26.10: 663-70, 2013.
Yearley et al., *Clin. Cancer. Res.*, 23: 3158-3167, 2017.
Yu et al., *Nature* 455:532-536, 2008.

The invention claimed is:

1. An antibody or antigen binding fragment thereof comprising:
   (a) heavy chain CDR1 sequence of SEQ ID NO: 27, heavy chain CDR2 sequence of SEQ ID NO: 28, and heavy chain CDR3 sequence of SEQ ID NO: 29; and light chain CDR1 sequence of SEQ ID NO: 45, light chain CDR2 sequence of SEQ ID NO: 46, and light chain CDR3 sequence of SEQ ID NO: 47;
   (b) heavy chain CDR1 sequence of SEQ ID NO: 30, heavy chain CDR2 sequence of SEQ ID NO: 31 and heavy chain CDR3 sequence of SEQ ID NO: 32 and light chain CDR1 sequence of SEQ ID NO: 48, light chain CDR2 sequence of SEQ ID NO: 49 and light chain CDR3 sequence of SEQ ID NO: 50;
   (c) heavy chain CDR1 sequence of SEQ ID NO: 33, heavy chain CDR2 sequence of SEQ ID NO: 34 and heavy chain CDR3 sequence of SEQ ID NO: 35 and light chain CDR1 sequence of SEQ ID NO: 51, light chain CDR2 sequence of SEQ ID NO: 52 and light chain CDR3 sequence of SEQ ID NO: 53;
   (d) heavy chain CDR1 sequence of SEQ ID NO: 36, heavy chain CDR2 sequence of SEQ ID NO: 37 and heavy chain CDR3 sequence of SEQ ID NO: 38 and light chain CDR1 sequence of SEQ ID NO: 54, light chain CDR2 sequence of SEQ ID NO: 55 and light chain CDR3 sequence of SEQ ID NO: 56;
   (e) heavy chain CDR1 sequence of SEQ ID NO: 39, heavy chain CDR2 sequence of SEQ ID NO: 40 and heavy chain CDR3 sequence of SEQ ID NO: 41 and light chain CDR1 sequence of SEQ ID NO: 57, light chain CDR2 sequence of SEQ ID NO: 58 and light chain CDR3 sequence of SEQ ID NO: 59;
   (f) heavy chain CDR1 sequence of SEQ ID NO: 42, heavy chain CDR2 sequence of SEQ ID NO: 43, and heavy chain CDR3 sequence of SEQ ID NO: 44; and light chain CDR1 sequence of SEQ ID NO: 60, light chain CDR2 sequence of SEQ ID NO: 61 and light chain CDR3 sequence of SEQ ID NO: 62;
(g) heavy chain CDR1 sequence of SEQ ID NO: 72, heavy chain CDR2 sequence of SEQ ID NO: 73 and heavy chain CDR3 sequence of SEQ ID NO: 74 and light chain CDR1 sequence of SEQ ID NO: 87, light chain CDR2 sequence of SEQ ID NO: 88 and light chain CDR3 sequence of SEQ ID NO: 89;
(h) heavy chain CDR1 sequence of SEQ ID NO: 75, heavy chain CDR2 sequence of SEQ ID NO: 76 and heavy chain CDR3 sequence of SEQ ID NO: 77 and light chain CDR1 sequence of SEQ ID NO: 90, light chain CDR2 sequence of SEQ ID NO: 91 and light chain CDR3 sequence of SEQ ID NO: 92;
(i) heavy chain CDR1 sequence of SEQ ID NO: 78, heavy chain CDR2 sequence of SEQ ID NO: 79 and heavy chain CDR3 sequence of SEQ ID NO: 80 and light chain CDR1 sequence of SEQ ID NO: 93, light chain CDR2 sequence of SEQ ID NO: 94 and light chain CDR3 sequence of SEQ ID NO: 95;
(j) heavy chain CDR1 sequence of SEQ ID NO: 81, heavy chain CDR2 sequence of SEQ ID NO: 82 and heavy chain CDR3 sequence of SEQ ID NO: 83 and light chain CDR1 sequence of SEQ ID NO: 96, light chain CDR2 sequence of SEQ ID NO: 97 and light chain CDR3 sequence of SEQ ID NO: 98; or
(k) heavy chain CDR1 sequence of SEQ ID NO: 84, heavy chain CDR2 sequence of SEQ ID NO: 85 and heavy chain CDR3 sequence of SEQ ID NO: 86 and light chain CDR1 sequence of SEQ ID NO: 99, light chain CDR2 sequence of SEQ ID NO: 100 and light chain CDR3 sequence of SEQ ID NO: 101.

2. The antibody or antigen binding fragment thereof of claim 1, wherein said antibody or antibody fragment comprises heavy and light chain variable sequences having at least 85% identity to:
(a) a heavy chain variable region comprising SEQ ID NO: 15 and a light chain variable region comprising SEQ ID NO: 16;
(b) a heavy chain variable region comprising SEQ ID NO: 17 and a light chain variable region comprising SEQ ID NO: 18;
(c) a heavy chain variable region comprising SEQ ID NO: 19 and a light chain variable region comprising SEQ ID NO: 20;
(d) a heavy chain variable region comprising SEQ ID NO: 21 and a light chain variable region comprising SEQ ID NO: 22;
(e) a heavy chain variable region comprising SEQ ID NO: 23 and a light chain variable region comprising SEQ ID NO: 24;
(f) a heavy chain variable region comprising SEQ ID NO: 25 and a light chain variable region comprising SEQ ID NO: 26;
(g) a heavy chain variable region comprising SEQ ID NO: 63 and a light chain variable region comprising SEQ ID NO: 64;
(h) a heavy chain variable region comprising SEQ ID NO: 65 and a light chain variable region comprising SEQ ID NO: 66;
(i) a heavy chain variable region comprising SEQ ID NO: 67 and a light chain variable region comprising SEQ ID NO: 68; or
(j) a heavy chain variable region comprising SEQ ID NO: 69 and a light chain variable region comprising SEQ ID NO: 70.

3. The antibody or antigen binding fragment thereof of claim 1, wherein said antibody or antibody fragment comprises the following sequences:
(a) a heavy chain variable region comprising SEQ ID NO: 15 and a light chain variable region comprising SEQ ID NO: 16;
(b) a heavy chain variable region comprising SEQ ID NO: 17 and a light chain variable region comprising SEQ ID NO: 18;
(c) a heavy chain variable region comprising SEQ ID NO: 19 and a light chain variable region comprising SEQ ID NO: 20;
(d) a heavy chain variable region comprising SEQ ID NO: 21 and a light chain variable region comprising SEQ ID NO: 22;
(e) a heavy chain variable region comprising SEQ ID NO: 23 and a light chain variable region comprising SEQ ID NO: 24;
(f) a heavy chain variable region comprising SEQ ID NO: 25 and a light chain variable region comprising SEQ ID NO: 26;
(g) a heavy chain variable region comprising SEQ ID NO: 63 and a light chain variable region comprising SEQ ID NO: 64;
(h) a heavy chain variable region comprising SEQ ID NO: 65 and a light chain variable region comprising SEQ ID NO: 66;
(i) a heavy chain variable region comprising SEQ ID NO: 67 and a light chain variable region comprising SEQ ID NO: 68; or
(j) a heavy chain variable region comprising SEQ ID NO: 69 and a light chain variable region comprising SEQ ID NO: 70.

4. The antibody or antigen binding fragment thereof of claim 1, wherein the antibody fragment is a recombinant scFv (single chain fragment variable) antibody, Fab fragment, F(ab')$_2$ fragment, or Fv fragment.

5. The antibody or antigen binding fragment thereof of claim 1, wherein said antibody is a chimeric antibody.

6. The antibody or antigen binding fragment thereof of claim 1, wherein said antibody is an IgG.

7. The antibody or fragment of claim 1, wherein said antibody or antigen binding fragment thereof is a human antibody.

8. A pharmaceutical formulation comprising one or more antibodies or antigen binding fragments thereof comprising:
(a) heavy chain CDR1 sequence of SEQ ID NO: 27, heavy chain CDR2 sequence of SEQ ID NO: 28, and heavy chain CDR3 sequence of SEQ ID NO: 29; and light chain CDR1 sequence of SEQ ID NO: 45, light chain CDR2 sequence of SEQ ID NO: 46, and light chain CDR3 sequence of SEQ ID NO: 47;
(b) heavy chain CDR1 sequence of SEQ ID NO: 30, heavy chain CDR2 sequence of SEQ ID NO: 31 and heavy chain CDR3 sequence of SEQ ID NO: 32 and light chain CDR1 sequence of SEQ ID NO: 48, light chain CDR2 sequence of SEQ ID NO: 49 and light chain CDR3 sequence of SEQ ID NO: 50;
(c) heavy chain CDR1 sequence of SEQ ID NO: 33, heavy chain CDR2 sequence of SEQ ID NO: 34 and heavy chain CDR3 sequence of SEQ ID NO: 35 and light chain CDR1 sequence of SEQ ID NO: 51, light chain CDR2 sequence of SEQ ID NO: 52 and light chain CDR3 sequence of SEQ ID NO: 53;
(d) heavy chain CDR1 sequence of SEQ ID NO: 36, heavy chain CDR2 sequence of SEQ ID NO: 37 and heavy chain CDR3 sequence of SEQ ID NO: 38 and light chain CDR1 sequence of SEQ ID NO: 54, light chain CDR2 sequence of SEQ ID NO: 55 and light chain CDR3 sequence of SEQ ID NO: 56;
(e) heavy chain CDR1 sequence of SEQ ID NO: 39, heavy chain CDR2 sequence of SEQ ID NO: 40 and heavy chain CDR3 sequence of SEQ ID NO: 41 and light chain CDR1 sequence of SEQ ID NO: 57, light chain CDR2 sequence of SEQ ID NO: 58 and light chain CDR3 sequence of SEQ ID NO: 59;
(f) heavy chain CDR1 sequence of SEQ ID NO: 42, heavy chain CDR2 sequence of SEQ ID NO: 43, and heavy chain CDR3 sequence of SEQ ID NO: 44; and light chain CDR1 sequence of SEQ ID NO: 60, light chain CDR2 sequence of SEQ ID NO: 61 and light chain CDR3 sequence of SEQ ID NO: 62;
(g) heavy chain CDR1 sequence of SEQ ID NO: 72, heavy chain CDR2 sequence of SEQ ID NO: 73 and heavy chain CDR3 sequence of SEQ ID NO: 74 and light chain CDR1 sequence of SEQ ID NO: 87, light chain CDR2 sequence of SEQ ID NO: 88 and light chain CDR3 sequence of SEQ ID NO: 89;
(h) heavy chain CDR1 sequence of SEQ ID NO: 75, heavy chain CDR2 sequence of SEQ ID NO: 76 and heavy chain CDR3 sequence of SEQ ID NO: 77 and light chain CDR1 sequence of SEQ ID NO: 90, light chain CDR2 sequence of SEQ ID NO: 91 and light chain CDR3 sequence of SEQ ID NO: 92;
(i) heavy chain CDR1 sequence of SEQ ID NO: 78, heavy chain CDR2 sequence of SEQ ID NO: 79 and heavy chain CDR3 sequence of SEQ ID NO: 80 and light chain CDR1 sequence of SEQ ID NO: 93, light chain CDR2 sequence of SEQ ID NO: 94 and light chain CDR3 sequence of SEQ ID NO: 95;
(j) heavy chain CDR1 sequence of SEQ ID NO: 81, heavy chain CDR2 sequence of SEQ ID NO: 82 and heavy chain CDR3 sequence of SEQ ID NO: 83 and light chain CDR1 sequence of SEQ ID NO: 96, light chain CDR2 sequence of SEQ ID NO: 97 and light chain CDR3 sequence of SEQ ID NO: 98; or
(k) heavy chain CDR1 sequence of SEQ ID NO: 84, heavy chain CDR2 sequence of SEQ ID NO: 85 and heavy chain CDR3 sequence of SEQ ID NO: 86 and light chain CDR1 sequence of SEQ ID NO: 99, light chain CDR2 sequence of SEQ ID NO: 100 and light chain CDR3 sequence of SEQ ID NO: 101.

9. A method of detecting a programmed death-ligand 1 (PD-L1) or programmed death-ligand 2 (PD-L2) expressing cell in a subject comprising:
(a) contacting a sample from said subject with an antibody or antigen binding fragment thereof comprising:
(i) heavy chain CDR1 sequence of SEQ ID NO: 27, heavy chain CDR2 sequence of SEQ ID NO: 28, and heavy chain CDR3 sequence of SEQ ID NO: 29; and light chain CDR1 sequence of SEQ ID NO: 45, light chain CDR2 sequence of SEQ ID NO: 46, and light chain CDR3 sequence of SEQ ID NO: 47;
(ii) heavy chain CDR1 sequence of SEQ ID NO: 30, heavy chain CDR2 sequence of SEQ ID NO: 31 and heavy chain CDR3 sequence of SEQ ID NO: 32 and light chain CDR1 sequence of SEQ ID NO: 48, light chain CDR2 sequence of SEQ ID NO: 49 and light chain CDR3 sequence of SEQ ID NO: 50;
(iii) heavy chain CDR1 sequence of SEQ ID NO: 33, heavy chain CDR2 sequence of SEQ ID NO: 34 and heavy chain CDR3 sequence of SEQ ID NO: 35 and light chain CDR1 sequence of SEQ ID NO: 51, light chain CDR2 sequence of SEQ ID NO: 52 and light chain CDR3 sequence of SEQ ID NO: 53;
(iv) heavy chain CDR1 sequence of SEQ ID NO: 36, heavy chain CDR2 sequence of SEQ ID NO: 37 and heavy chain CDR3 sequence of SEQ ID NO: 38 and light chain CDR1 sequence of SEQ ID NO: 54, light chain CDR2 sequence of SEQ ID NO: 55 and light chain CDR3 sequence of SEQ ID NO: 56;
(v) heavy chain CDR1 sequence of SEQ ID NO: 39, heavy chain CDR2 sequence of SEQ ID NO: 40 and heavy chain CDR3 sequence of SEQ ID NO: 41 and light chain CDR1 sequence of SEQ ID NO: 57, light chain CDR2 sequence of SEQ ID NO: 58 and light chain CDR3 sequence of SEQ ID NO: 59;
(vi) heavy chain CDR1 sequence of SEQ ID NO: 42, heavy chain CDR2 sequence of SEQ ID NO: 43, and heavy chain CDR3 sequence of SEQ ID NO: 44; and light chain CDR1 sequence of SEQ ID NO: 60, light chain CDR2 sequence of SEQ ID NO: 61 and light chain CDR3 sequence of SEQ ID NO: 62;
(vii) heavy chain CDR1 sequence of SEQ ID NO: 72, heavy chain CDR2 sequence of SEQ ID NO: 73 and heavy chain CDR3 sequence of SEQ ID NO: 74 and light chain CDR1 sequence of SEQ ID NO: 87, light chain CDR2 sequence of SEQ ID NO: 88 and light chain CDR3 sequence of SEQ ID NO: 89;
(viii) heavy chain CDR1 sequence of SEQ ID NO: 75, heavy chain CDR2 sequence of SEQ ID NO: 76 and heavy chain CDR3 sequence of SEQ ID NO: 77 and light chain CDR1 sequence of SEQ ID NO: 90, light chain CDR2 sequence of SEQ ID NO: 91 and light chain CDR3 sequence of SEQ ID NO: 92;
(ix) heavy chain CDR1 sequence of SEQ ID NO: 78, heavy chain CDR2 sequence of SEQ ID NO: 79 and heavy chain CDR3 sequence of SEQ ID NO: 80 and light chain CDR1 sequence of SEQ ID NO: 93, light chain CDR2 sequence of SEQ ID NO: 94 and light chain CDR3 sequence of SEQ ID NO: 95;
(x) heavy chain CDR1 sequence of SEQ ID NO: 81, heavy chain CDR2 sequence of SEQ ID NO: 82 and heavy chain CDR3 sequence of SEQ ID NO: 83 and light chain CDR1 sequence of SEQ ID NO: 96, light chain CDR2 sequence of SEQ ID NO: 97 and light chain CDR3 sequence of SEQ ID NO: 98; or
(xi) heavy chain CDR1 sequence of SEQ ID NO: 84, heavy chain CDR2 sequence of SEQ ID NO: 85 and heavy chain CDR3 sequence of SEQ ID NO: 86 and light chain CDR1 sequence of SEQ ID NO: 99, light chain CDR2 sequence of SEQ ID NO: 100 and light chain CDR3 sequence of SEQ ID NO: 101; and
(b) detecting a PD-L1 or PD-L2 expressing cell in said sample by binding of said antibody or antibody fragment to a cell in said sample.

10. A hybridoma or engineered cell comprising a nucleic acid encoding an antibody or antigen binding fragment thereof, wherein the antibody or antibody fragment comprises:
(a) heavy chain CDR1 sequence of SEQ ID NO: 27, heavy chain CDR2 sequence of SEQ ID NO: 28, and heavy chain CDR3 sequence of SEQ ID NO: 29; and light chain CDR1 sequence of SEQ ID NO: 45, light chain CDR2 sequence of SEQ ID NO: 46, and light chain CDR3 sequence of SEQ ID NO: 47;
(b) heavy chain CDR1 sequence of SEQ ID NO: 30, heavy chain CDR2 sequence of SEQ ID NO: 31 and heavy chain CDR3 sequence of SEQ ID NO: 32 and light chain CDR1 sequence of SEQ ID NO: 48, light chain CDR2 sequence of SEQ ID NO: 49 and light chain CDR3 sequence of SEQ ID NO: 50;
(c) heavy chain CDR1 sequence of SEQ ID NO: 33, heavy chain CDR2 sequence of SEQ ID NO: 34 and heavy chain CDR3 sequence of SEQ ID NO: 35 and light chain CDR1 sequence of SEQ ID NO: 51, light chain CDR2 sequence of SEQ ID NO: 52 and light chain CDR3 sequence of SEQ ID NO: 53;
(d) heavy chain CDR1 sequence of SEQ ID NO: 36, heavy chain CDR2 sequence of SEQ ID NO: 37 and heavy chain CDR3 sequence of SEQ ID NO: 38 and light chain CDR1 sequence of SEQ ID NO: 54, light chain CDR2 sequence of SEQ ID NO: 55 and light chain CDR3 sequence of SEQ ID NO: 56;
(e) heavy chain CDR1 sequence of SEQ ID NO: 39, heavy chain CDR2 sequence of SEQ ID NO: 40 and heavy chain CDR3 sequence of SEQ ID NO: 41 and light chain CDR1 sequence of SEQ ID NO: 57, light chain CDR2 sequence of SEQ ID NO: 58 and light chain CDR3 sequence of SEQ ID NO: 59;
(f) heavy chain CDR1 sequence of SEQ ID NO: 42, heavy chain CDR2 sequence of SEQ ID NO: 43, and heavy chain CDR3 sequence of SEQ ID NO: 44; and light chain CDR1 sequence of SEQ ID NO: 60, light chain CDR2 sequence of SEQ ID NO: 61 and light chain CDR3 sequence of SEQ ID NO: 62;
(g) heavy chain CDR1 sequence of SEQ ID NO: 72, heavy chain CDR2 sequence of SEQ ID NO: 73 and heavy chain CDR3 sequence of SEQ ID NO: 74 and light chain CDR1 sequence of SEQ ID NO: 87, light chain CDR2 sequence of SEQ ID NO: 88 and light chain CDR3 sequence of SEQ ID NO: 89;
(h) heavy chain CDR1 sequence of SEQ ID NO: 75, heavy chain CDR2 sequence of SEQ ID NO: 76 and heavy chain CDR3 sequence of SEQ ID NO: 77 and light chain CDR1 sequence of SEQ ID NO: 90, light chain CDR2 sequence of SEQ ID NO: 91 and light chain CDR3 sequence of SEQ ID NO: 92;
(i) heavy chain CDR1 sequence of SEQ ID NO: 78, heavy chain CDR2 sequence of SEQ ID NO: 79 and heavy chain CDR3 sequence of SEQ ID NO: 80 and light chain CDR1 sequence of SEQ ID NO: 93, light chain CDR2 sequence of SEQ ID NO: 94 and light chain CDR3 sequence of SEQ ID NO: 95;
(j) heavy chain CDR1 sequence of SEQ ID NO: 81, heavy chain CDR2 sequence of SEQ ID NO: 82 and heavy chain CDR3 sequence of SEQ ID NO: 83 and light chain CDR1 sequence of SEQ ID NO: 96, light chain CDR2 sequence of SEQ ID NO: 97 and light chain CDR3 sequence of SEQ ID NO: 98; or
(k) heavy chain CDR1 sequence of SEQ ID NO: 84, heavy chain CDR2 sequence of SEQ ID NO: 85 and heavy chain CDR3 sequence of SEQ ID NO: 86 and light chain CDR1 sequence of SEQ ID NO: 99, light chain CDR2 sequence of SEQ ID NO: 100 and light chain CDR3 sequence of SEQ ID NO: 101.

11. The antibody or antigen binding fragment thereof of claim 1, wherein said antibody or antibody fragment is encoded by heavy and light chain variable sequences having at least 85% identity to:
(a) a heavy chain variable region comprising SEQ ID NO: 3 and a light chain variable region comprising SEQ ID NO: 4;
(b) a heavy chain variable region comprising SEQ ID NO: 5 and a light chain variable region comprising SEQ ID NO: 6;
(c) a heavy chain variable region comprising SEQ ID NO: 7 and a light chain variable region comprising SEQ ID NO: 8;
(d) a heavy chain variable region comprising SEQ ID NO: 9 and a light chain variable region comprising SEQ ID NO: 10;
(e) a heavy chain variable region comprising SEQ ID NO: 11 and a light chain variable region comprising SEQ ID NO: 12; or
(f) a heavy chain variable region comprising SEQ ID NO: 13 and a light chain variable region comprising SEQ ID NO: 14.

12. The antibody or antigen binding fragment thereof of claim 1, wherein said antibody or antibody fragment is encoded by the following heavy and light chain variable sequences:
(a) a heavy chain variable region comprising SEQ ID NO: 3 and a light chain variable region comprising SEQ ID NO: 4;
(b) a heavy chain variable region comprising SEQ ID NO: 5 and a light chain variable region comprising SEQ ID NO: 6;
(c) a heavy chain variable region comprising SEQ ID NO: 7 and a light chain variable region comprising SEQ ID NO: 8;
(d) a heavy chain variable region comprising SEQ ID NO: 9 and a light chain variable region comprising SEQ ID NO: 10;
(e) a heavy chain variable region comprising SEQ ID NO: 11 and a light chain variable region comprising SEQ ID NO: 12; or
(f) a heavy chain variable region comprising SEQ ID NO: 13 and a light chain variable region comprising SEQ ID NO: 14.

13. The antibody or antigen binding fragment thereof of claim 11, wherein said antibody or antibody fragment is encoded by heavy and light chain variable sequences having at least 90% identity to:
(a) a heavy chain variable region comprising SEQ ID NO: 3 and a light chain variable region comprising SEQ ID NO: 4;
(b) a heavy chain variable region comprising SEQ ID NO: 5 and a light chain variable region comprising SEQ ID NO: 6;
(c) a heavy chain variable region comprising SEQ ID NO: 7 and a light chain variable region comprising SEQ ID NO: 8;
(d) a heavy chain variable region comprising SEQ ID NO: 9 and a light chain variable region comprising SEQ ID NO: 10;
(e) a heavy chain variable region comprising SEQ ID NO: 11 and a light chain variable region comprising SEQ ID NO: 12; or
(f) a heavy chain variable region comprising SEQ ID NO: 13 and a light chain variable region comprising SEQ ID NO: 14.

14. The antibody or antigen binding fragment thereof of claim 11, wherein said antibody or antibody fragment is encoded by heavy and light chain variable sequences having at least 95% identity to:
(a) a heavy chain variable region comprising SEQ ID NO: 3 and a light chain variable region comprising SEQ ID NO: 4;
(b) a heavy chain variable region comprising SEQ ID NO: 5 and a light chain variable region comprising SEQ ID NO: 6;

(c) a heavy chain variable region comprising SEQ ID NO: 7 and a light chain variable region comprising SEQ ID NO: 8;
(d) a heavy chain variable region comprising SEQ ID NO: 9 and a light chain variable region comprising SEQ ID NO: 10;
(e) a heavy chain variable region comprising SEQ ID NO: 11 and a light chain variable region comprising SEQ ID NO: 12; or
(f) a heavy chain variable region comprising SEQ ID NO: 13 and a light chain variable region comprising SEQ ID NO: 14.

15. The antibody or antigen binding fragment thereof of claim 2, wherein said antibody or antibody fragment comprises heavy and light chain variable sequence having at least 90% identity to:
  (a) a heavy chain variable region comprising SEQ ID NO: 15 and a light chain variable region comprising SEQ ID NO: 16;
  (b) a heavy chain variable region comprising SEQ ID NO: 17 and a light chain variable region comprising SEQ ID NO: 18;
  (c) a heavy chain variable region comprising SEQ ID NO: 19 and a light chain variable region comprising SEQ ID NO: 20;
  (d) a heavy chain variable region comprising SEQ ID NO: 21 and a light chain variable region comprising SEQ ID NO: 22;
  (e) a heavy chain variable region comprising SEQ ID NO: 23 and a light chain variable region comprising SEQ ID NO: 24;
  (f) a heavy chain variable region comprising SEQ ID NO: 25 and a light chain variable region comprising SEQ ID NO: 26;
  (g) a heavy chain variable region comprising SEQ ID NO: 63 and a light chain variable region comprising SEQ ID NO: 64;
  (h) a heavy chain variable region comprising SEQ ID NO: 65 and a light chain variable region comprising SEQ ID NO: 66;
  (i) a heavy chain variable region comprising SEQ ID NO: 67 and a light chain variable region comprising SEQ ID NO: 68; or
  (j) a heavy chain variable region comprising SEQ ID NO: 69 and a light chain variable region comprising SEQ ID NO: 70.

16. The antibody or antigen binding fragment thereof of claim 2, wherein said antibody or antibody fragment comprises heavy and light chain variable sequence having at least 95% identity to:
  (a) a heavy chain variable region comprising SEQ ID NO: 15 and a light chain variable region comprising SEQ ID NO: 16;
  (b) a heavy chain variable region comprising SEQ ID NO: 17 and a light chain variable region comprising SEQ ID NO: 18;
  (c) a heavy chain variable region comprising SEQ ID NO: 19 and a light chain variable region comprising SEQ ID NO: 20;
  (d) a heavy chain variable region comprising SEQ ID NO: 21 and a light chain variable region comprising SEQ ID NO: 22;
  (e) a heavy chain variable region comprising SEQ ID NO: 23 and a light chain variable region comprising SEQ ID NO: 24;
  (f) a heavy chain variable region comprising SEQ ID NO: 25 and a light chain variable region comprising SEQ ID NO: 26;
  (g) a heavy chain variable region comprising SEQ ID NO: 63 and a light chain variable region comprising SEQ ID NO: 64;
  (h) a heavy chain variable region comprising SEQ ID NO: 65 and a light chain variable region comprising SEQ ID NO: 66;
  (i) a heavy chain variable region comprising SEQ ID NO: 67 and a light chain variable region comprising SEQ ID NO: 68; or
  (j) a heavy chain variable region comprising SEQ ID NO: 69 and a light chain variable region comprising SEQ ID NO: 70.

* * * * *